(12) United States Patent
Curd et al.

(10) Patent No.: US 8,883,775 B2
(45) Date of Patent: Nov. 11, 2014

(54) TREATMENT OF HYPERPROLIFERATIVE DISEASES WITH VINCA ALKALOID N-OXIDE ANALOGS

(75) Inventors: John G. Curd, Hillsborough, CA (US); John F. W. Keana, Eugene, OR (US); Alshad S. Lalani, Terrytown, NY (US); Paul B. Westberg, San Mateo, CA (US); Bradford Goodwin, San Mateo, CA (US); W. David Henner, Tucson, AZ (US)

(73) Assignee: Cascade Prodrug Inc., Eugene, OR (US)

( * ) Notice: Subject to any disclaimer, the term of this patent is extended or adjusted under 35 U.S.C. 154(b) by 319 days.

(21) Appl. No.: 13/280,974

(22) Filed: Oct. 25, 2011

(65) Prior Publication Data

US 2012/0107230 A1 May 3, 2012

Related U.S. Application Data

(60) Division of application No. 12/111,672, filed on Apr. 29, 2008, now Pat. No. 8,048,872, which is a continuation-in-part of application No. PCT/US2007/004252, filed on Feb. 20, 2007.

(60) Provisional application No. 60/774,204, filed on Feb. 17, 2006.

(51) Int. Cl.
*A61K 31/55* (2006.01)
*A61K 31/435* (2006.01)
*C07D 519/04* (2006.01)

(52) U.S. Cl.
CPC .................................. *C07D 519/04* (2013.01)
USPC ..................................... 514/214.03; 514/283

(58) Field of Classification Search
CPC .................................................... C07D 519/04
See application file for complete search history.

(56) References Cited

U.S. PATENT DOCUMENTS

| 4,303,584 | A | 12/1981 | Pearce |
| 4,307,100 | A | 12/1981 | Langlois et al. |
| 4,347,249 | A | 8/1982 | Potier et al. |
| 5,047,528 | A | 9/1991 | Kutney et al. |
| 6,242,457 | B1 | 6/2001 | Penco et al. |
| RE37,449 | E | 11/2001 | Kutney et al. |
| 6,365,735 | B1 | 4/2002 | Rool |
| 6,555,547 | B1 | 4/2003 | Pamukcu et al. |
| 2005/0222190 | A1 | 10/2005 | Curd et al. |
| 2008/0089935 | A1* | 4/2008 | Bougaret et al. ............. 424/456 |

FOREIGN PATENT DOCUMENTS

| AU | B-72666/94 | 2/1995 |
| EP | 0 010 458 A1 | 4/1980 |
| WO | WO 2005/055939 A2 | 6/2005 |
| WO | WO 2005/055943 A2 | 6/2005 |

OTHER PUBLICATIONS

Barnett. Journal of Medicinal Chemistry, 1978, 21(1), 88-96.*
Neuss. Bulletin de la Societe Chimique de France, 1963, 8-9, 1509-16.*
"Prostate Cancer Prevention", http://www.cancer.gov/cancertopics/pdq/prevention/prostate/Patient, accessed Apr. 9, 2010.*
Jantzen and Robinson. Modern Pharmaceutics, 1996, p. 596.*
LADGIG. Mosby's GenRX, 1998, eighth edition, pp. II-2196-II-2199.*
"NCI Dictionary of Cancer Terms", http://www.cancer.gov/dictionary?cdrid=45301, accessed Jan. 23, 2013.*
Mukhopadhyay. Journal of Natural Products, 1981, 44(5), 611-613.*
Cibotti, M.C. et al., "Monoclonal Antibodies to Bis-Indole Alkaloids of *Catharanthus roseus* and Their Use in Enzyme-Linked Immuno-Sorbent-Assays," *Phytochemistry* 29:2109-2114, Pergamon Press (1990).
El-Sayed, A. et al., "*Catharanthus* Alkaloids, XXXVIII. Confirming Structural Evidence and Antineoplastic Activity of the Bisindole Alkaloids Leurosine-N'$_b$-oxide (Pleurosine), Roseadine and Vindolicine from *Catharanthus roseus*," *J. Nat. Prod.* 46:517-527, American Society of Pharmacognosy (1983).
Hussey, R.L. and Newlon, W.M., "High-Performance Liquid Chromatographic and TLC Determinations of Desacetylvinblastine Amide (Vindesine) and Its Monosulfate Salt," *J. Pharm. Sci.* 67:1319-1320, American Pharmaceutical Association (1978).
Mangeney, P. et al., "5'-Nor Anhydrovinblastine. Prototype of a New Class of Vinblastine Derivatives." *Tetrahedron* 35:2175-2179, Pergamon Press (1979).
Mukhopadhyay, S. and Cordell, G.A., "*Catharanthus* Alkaloids. XXXV. Isolation of Leurosidine N'$_b$-Oxide from *Catharanthus roseus*," *J. Nat. Prod.* 44:611-613, The American Society of Pharmacognosy (1981).
Spearman, M.E. et al., "Disposition of the Monoclonal Antibody-Vinca Alkaloid Conjugate, KS1/4-DAVLB (LY256787), in Fischer 344 Rats and Rhesus Monkeys," *Drug Metab. Dispos.* 15:640-647, The American Society for Pharmacology and Experimental Therapeutics (1987).
Thimmaiah, K.N. and Sethi, V.S., "Structural Investigations of the Products of Vincristine Sulfate Formed after in Vitro Incubation of the Alkaloid in Bile of Dogs," *Microchem. J.* 41:320-326, Academic Press, Inc. (1990).
International Search Report for International Patent Application No. PCT/US2007/004252, U.S. Patent and Trademark Office, Alexandria, Virginia, mailed Jun. 4, 2008.
Bickel, M.H., "The Pharmacology and Biochemistry of N-oxides," *Pharmacol. Rev.* 21:325-355, The Williams & Wilkins Co. (1969).
Brown, J.M. and Wilson, W.R., "Exploiting Tumour Hypoxia in Cancer Treatment," *Nat. Rev. Cancer* 4:437-447, Nature Pub. Group (2004).

(Continued)

*Primary Examiner* — Andrew D Kosar
*Assistant Examiner* — John S Kenyon
(74) *Attorney, Agent, or Firm* — Sterne, Kessler, Goldstein & Fox P.L.L.C.

(57) ABSTRACT

The present invention relates to vinca alkaloid and analog N-oxides having activity for treating hyperproliferative disorders. Further, the invention relates to pharmaceutical compositions and methods of using vinca alkaloid and analog N-oxides, alone or in combination with one or more other active agents or treatments, to treat hyperproliferative disorders.

26 Claims, 30 Drawing Sheets

(56) References Cited

OTHER PUBLICATIONS

Hadfield, J.A. et al., "Tubulin and microtubules as targets for anticancer drugs," *Progress in Cell Cycle Research* 5:309-325, Plenum (2003).

Jehl, F. et al., "Pharmacokinetic and Preliminary Metabolic Fate of Navelbine in Humans as Determined by High Performance Liquid Chromatography," *Cancer Research* 51:2073-2076, American Association for Cancer Research (1991).

Kuehne, M.E. et al., "The Syntheses of 16a'-*homo*-Leurosidine and 16a'-*homo*-Vinblastine. Generation of Atropisomers," *J. Org. Chem.* 66:5317-5328, American Chemical Society (2001).

Maguire, M.H. and Csonka-Khalifah, L., "Vinca alkaloids inhibit conversion of arachidonic acid to thromboxane by human platelet microsomes: comparison with other microtubule-active drugs," *Biochem. Biophys. Acta* 921:426-436, Elsevier Science Publishers B.V. (1987).

Morales-Ríos, M.S. et al., "$^{13}$C NMR Spectroscopy of Indole Derivatives," *Magnetic Resonance in Chemistry* 25:377-396, John Wiley & Sons, Ltd. (1987).

Ragot, S. et al., "Sensitive determination of vinorelbine and its metabolites in human serum using liquid chromatography-electrospray mass spectrometry," *J. Chromatography B* 753:167-178, Elsevier Science B.V. (2001).

Supplementary European search report for European Patent Application No. 07751041.0, European Patent Office, Munich, Germany, mailed Apr. 13, 2010.

Wargin, W.A. and Lucas, V.S., "The Clinical Pharmacokinetics of Vinorelbine (Navelbine)," *Seminars in Oncology* 21:21-27, W. B. Saunders Company (1994).

\* cited by examiner

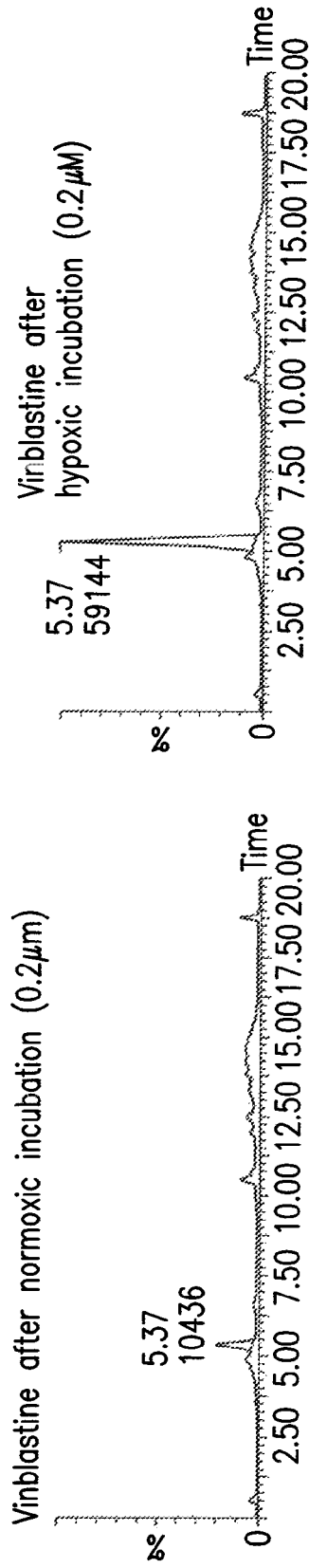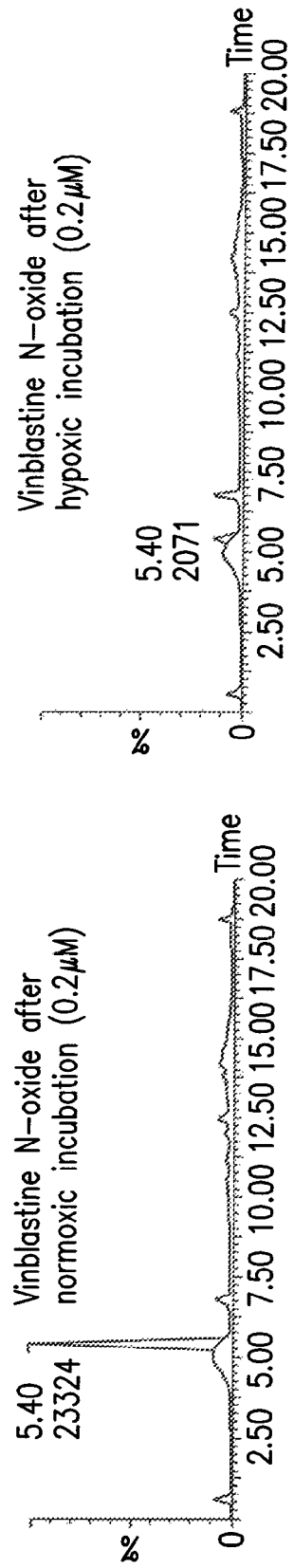
Figure 6A
Figure 6B
Figure 6C
Figure 6D

TREATMENT OF HYPERPROLIFERATIVE DISEASES WITH VINCA ALKALOID N-OXIDE ANALOGS

BACKGROUND OF THE INVENTION

1. Field of the Invention

The present invention relates to vinca alkaloid N-oxides having activity for treating hyperproliferative disorders. Further, the invention relates to pharmaceutical compositions and methods of using vinca alkaloid N-oxides, alone or in combination with one or more other active agents or treatments, to treat hyperproliferative disorders.

2. Related Art

One in every four deaths in the United States is due to cancer, and cancer is the second leading cause of death. U.S. Cancer Statistics Working Group; *United States Cancer Statistics: 2000 Incidence*, Atlanta (GA): Department of Health and Human Services, Centers for Disease Control and Prevention, and National Cancer Institute (2003). The National Cancer Institute reports that almost 10 million Americans have a history of invasive cancer, while the American Cancer Society estimates that in the year 2004, over 1.3 million Americans will receive a diagnosis of invasive cancer with over a half million cases resulting in death. American Cancer. Society, *Cancer Facts & Figures* 2004. These statistics exclude the 1 million cases of basal and squamous cell skin cancers that are expected to be diagnosed in the United States.

Cancers are classified based on the organ and cell tissue from which the cancer originates, including: (i) carcinomas (most common kind of cancer which originates in epithelial tissues, the layers of cells covering the body's surface or lining internal organs and various glands); (ii) leukemias (origination in the blood-forming tissues, including bone marrow, lymph nodes and the spleen); (iii) lymphomas (originates in the cells of the lymph system); (iv) melanomas (originates in the pigment cells located among the epithelial cells of the skin); and (v) sarcomas (originates in the connective tissues of the body, such as bones, muscles and blood vessels). (See Molecular Biology of the Cell: Third Edition, "Cancer," Chapter 24, pp. 1255-1294, B. Alberts et al., (eds.), Garland Publishing, Inc., New York (1994); and Stedman's Pocket Medical Dictionary; Williams and Wilkins, Baltimore (1987)). Within these broad cancer classifications, there are over one hundred cancer subclassifications, such as breast, lung, pancreatic, colon, and prostate cancer, to name a few.

Cancer cells develop as a result of damage to a cell's DNA (i.e., altered DNA sequence or altered expression pattern) from exposure to various chemical agents, radiation, viruses, or when some not-yet-fully-understood internal, cellular signaling event occurs. Most of the time when a cell's DNA becomes damaged, the cell either dies or is able to repair the DNA. However, for cancer cells, the damaged DNA is not repaired and the cell continues to divide, exhibiting modified cell physiology and function.

Neoplasms, or tumors, are masses of cells that result from an aberrant, accelerated rate of growth (i.e., hyperproliferative cell growth). As long as the tumor cells remain confined to a single mass, the tumor is considered to be benign. However, a cancerous tumor has the ability to invade other tissues and is termed malignant. In general, cancer cells are defined by two heritable properties: the cells and their progeny 1) reproduce in defiance of normal restraints, and 2) invade and colonize the territories of other cells.

Cancerous tumors are comprised of a highly complex vasculature and differentiated tissue. A large majority of cancerous tumors have hypoxic components, which are relatively resistant to standard anti-cancer treatment, including radiotherapy and chemotherapy. Brown, *Cancer Res.* 59:5863 (1999); and Kunz, M. et al., *Mol. Cancer.* 2:1 (2003). Thomlinson and Gray presented the first anatomical model of a human tumor that describes a 100 to 150 μm thick hypoxic layer of tissue located between the blood vessels and necrotic tumor tissues.

Research has shown that the hypoxic tissues within a number of cancerous tumors promote the progression of the cancer by an array of complex mechanisms. See, Brown, supra, and Kunz et al., supra. Among these are activation of certain signal transduction pathways and gene regulatory mechanisms, induction of selection processes for gene mutations, tumor cell apoptosis and tumor angiogenesis. Most of these mechanisms contribute to tumor progression. Therefore, tissue hypoxia has been regarded as a central factor for tumor aggressiveness and metastasis. Therapies that target hypoxic tissues within a tumor would certainly provide improved treatments to patients suffering from tumor-related cancers and/or disorders.

In addition to cancer, there exist a number of hyperproliferative diseases and/or disorders that are associated with the onset of hypoxia in a given tissue. For example, Shweiki et al. explains that inadequate oxygen levels often lead to neovascularization in order to compensate for the needs of the hypoxic tissue. Neovascularization is mediated by expression of certain growth factors, such as vascular endothelial growth factor (VEGF). Shweiki et al., *Nature* 359:843 (1992). However, when certain tissues or growth factors are either directly or indirectly upregulated in response to hypoxia without sufficient feedback mechanisms for controlling tissue expression, various diseases and/or disorders may ensue (i.e., by hypoxia-aggravated hyperproliferation). By way of example, hypoxia-aggravated hyperproliferative diseases and/or disorders having over-expressed levels of VEGF include ocular angiogenic diseases, such as age-related macular degeneration and diabetic retinopathy, as well as cirrhosis of the liver. See Frank, *Ophthalmic Res.* 29:341 (1997); Ishibashi et al., *Graefe's Archive Clin. Exp. Ophthamol.* 235:159 (1997); Corpechot et al., *Hepatology* 35:1010 (2002).

Vinca alkaloids are a class of chemotherapeutic agents originally discovered in the Madagascar periwinkle. Currently known vinca alkaloids include vinblastine, vincristine, vindesine and vinorelbine. Vinca alkaloids act by inhibiting mitosis in metaphase. These alkaloids bind to tubulin, thus preventing the cell from making the spindles it needs to be able to move its chromosomes around as it divides. These alkaloids also seem to interfere with cells' ability to synthesize DNA and RNA. They are all administered intravenously in their sulfate form once a week; these solutions are fatal if they are administered incorrectly, and can cause considerable tissue irritation if they leak out of the vein. See U.S. Pat. No. 6,555,547 for further detail.

U.S. Pat. No. 6,365,735 discloses a process for preparing vinca alkaloids of the general formula (I):

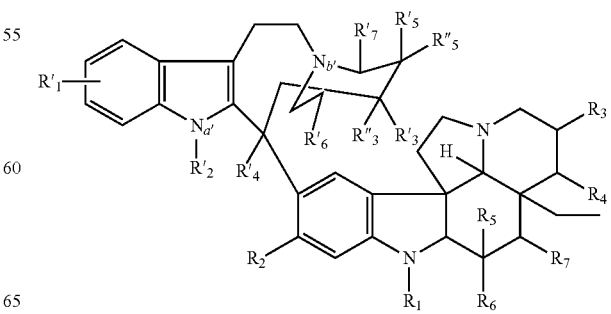

in which:

$R'_1$ represents a hydrogen atom or an alkoxy, acyl, formyl or halogenoacyl group, $R'_2$ represents a hydrogen atom or an alkyl group, $R'_3$ and $R''_3$ are identical or different and each independently represents a hydrogen atom or a hydroxyl or alkanoyloxyl group, or else $R'_3$ and $R''_3$ together form a carbonyl group or else $R'_3$ and $R'_5$ together form an epoxy bridge or a double bond, $R'_4$ represents a hydrogen atom or an alkyloxycarbonyl, hydroxymethyl or alkanoyloxymethyl group, preferably an alkyloxycarbonyl group, $R'_5$ and $R''_5$ are identical or different and each independently represents a hydrogen atom or a hydroxyl, alkanoyloxyl, ethyl or 2-hydroxyethyl group, $R'_6$ represents a hydrogen atom or an ethyl, 2-hydroxyethyl or acetyl group, $R'_7$ represents a hydrogen atom or a cyanide group, $R_1$ represents a hydrogen atom or an alkyl, formyl or acyl group, preferably hydrogen or an alkyl group, $R_2$ represents a hydrogen atom or an alkoxy group, $R_3$ represents a hydrogen atom or a hydroxyl or alkanoyloxyl group, or else $R_3$ and $R_4$ together form an epoxy bridge or a double bond, $R_4$ represents a hydrogen atom or a hydroxyl or alkanoyloxyl group, or else $R_4$ and $R_5$ together form an epoxy bridge, $R_6$ represents an alkyloxycarbonyl, hydrazido, acetamido, hydroxymethyl or alkanoyloxymethyl group, $R_5$ and $R_7$ represent a hydrogen atom or a hydroxyl or alkanoyloxyl group, as well as their addition salts with acids and their quaternary ammonium salts.

Disclosed also are additional classes of vinca alkaloids as well specific vinca alkaloids such as vinblastine, vincristine, anhydrovinblastine and vinorelbine.

BRIEF SUMMARY OF THE INVENTION

The present invention is related to compounds, compositions and methods for treating hyperproliferative disorders, such as cancer and inflammation. One aspect of the invention is drawn to vinca alkaloid N-oxides having Formula I:

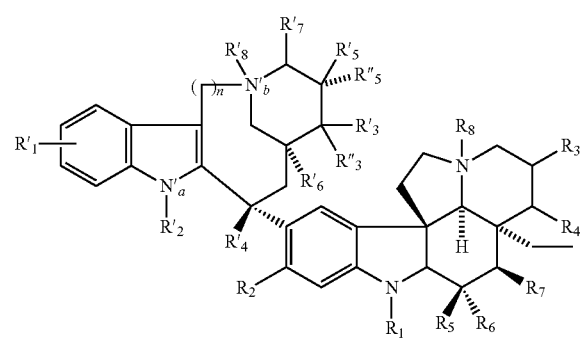

I or a pharmaceutically acceptable salt thereof, wherein:

$R'_1$ represents hydrogen, alkyl, alkoxy, acyl, formyl or halogenoacyl group;

$R'_2$ represents hydrogen or alkyl group;

$R'_3$ and $R''_3$ are identical or different and each independently represents hydrogen, hydroxy or alkanoyloxy group, or else $R'_3$ and $R''_3$ together form a carbonyl group or else $R'_3$ and $R'_5$ together form an epoxy bridge or a double bond;

$R'_4$ represents hydrogen, alkyloxycarbonyl, hydroxymethyl or alkanoyloxymethyl group, preferably an alkyloxycarbonyl group;

$R'_5$ and $R''_5$ are identical or different and each independently represents hydrogen, hydroxy, alkoxycarbonyl, $C_1$-$C_7$ alkyl optionally substituted with 1-3 halogen atoms, alkanoyloxy, or 2-hydroxyethyl group;

$R'_6$ represents hydrogen, ethyl, 2-hydroxyethyl or acetyl group;

$R'_7$ represents hydrogen or cyano;

$R_1$ represents hydrogen, alkyl, formyl or acyl group, preferably hydrogen or an alkyl group, $R_2$ represents hydrogen or alkoxy;

$R_3$ represents hydrogen, hydroxy or alkanoyloxy group, or else $R_3$ and $R_4$ together form an epoxy bridge or a double bond;

$R_4$ represents hydrogen, hydroxy or alkanoyloxy group, or else $R_4$ and $R_5$ together form an epoxy bridge;

$R_6$ represents an alkyloxycarbonyl, hydrazido, acetamido, hydroxymethyl, alkanoyloxymethyl group or —C(=O)-A-NH—P, where -A- is one of —NH—, —NH-alk-COO— or —NH-alk-COONH—, alk is a straight chain or branched $C_1$-$C_7$ alkyl group and —NH—P is a peptide residue, or $R_5$ and $R_6$ together form an oxazolidine-2,4-dione ring;

$R_5$ and $R_7$ represent hydrogen, hydroxy or alkanoyloxy group, as well as their addition salts with acids and their quaternary ammonium salts;

each of $R_8$ and $R'_8$ is O or is absent provided that at least one of $R_8$ and $R'_8$ is O; and n is 1 or 2.

In one embodiment, when n=2 and one of $R'_5$ and $R''_5$ forms a double bond together with $R'_3$ or $R''_3$, then the other is not ethyl.

In one embodiment, the compound having formula I is vinblastine N-oxide, desacetyl vinblastine N-oxide, vinorelbine N-oxide, vincristine N-oxide or vinflunine N-oxide, or a pharmaceutically acceptable salt thereof.

Another aspect of the present invention is related to methods for treating hyperproliferative disorders. In certain aspects of the invention, the hyperproliferative disorder is cancer. In one embodiment, the cancer is a solid tumor. In another embodiment, the cancer is selected from the group consisting of colon cancer, brain cancer, glioma, multiple myeloma, head and neck cancer, hepatocellular cancer, melanoma, ovarian cancer, cervical cancer, renal cancer, and non-small cell lung cancer. In a further embodiment, the cancer is acute and chronic lymphocytic leukemia, acute granulocytic leukemia, adrenal cortex carcinoma, bladder carcinoma, breast carcinoma, cervical carcinoma, cervical hyperplasia, choriocarcinoma, chronic granulocytic leukemia, chronic lymphocytic leukemia, colon carcinoma, endometrial carcinoma, esophageal carcinoma, essential thrombocytosis, genitourinary carcinoma, hairy cell leukemia, head and neck carcinoma, Hodgkin's disease, Kaposi's sarcoma, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid and lymphocytic leukemia, neuroblastoma, non-Hodgkin's lymphoma, osteogenic sarcoma, ovarian carcinoma, pancreatic carcinoma, polycythemia vera, primary brain carcinoma, primary macroglobulinemia, prostatic carcinoma, renal cell carcinoma, rhabdomyos'arcoma, skin cancer, small-cell lung carcinoma, soft-tissue sarcoma, squamous cell carcinoma, stomach carcinoma, testicular carcinoma, thyroid carcinoma, or Wilms' tumor.

In further aspects of the invention the hyperproliferative disorder is any one of age-related macular degeneration, Crohn's disease, cirrhosis, chronic inflammatory-related disorders, proliferative diabetic retinopathy, proliferative vitreoretinopathy, retinopathy of prematurity, granulomatosis, immune hyperproliferation associated with organ or tissue transplantation, an immunoproliferative disease or disorder, e.g., inflammatory bowel disease, psoriasis, rheumatoid arthritis, systemic lupus erythematosus (SLE), vascular hyperproliferation secondary to retinal hypoxia, or vasculitis.

In one embodiment the invention is drawn to methods of treating, ameliorating, or preventing hyperproliferative disease in a subject comprising administering to said subject a therapeutically effective amount of an N-oxide of vinca alkaloid or analog thereof. In another embodiment, the vinca alkaloid analog is selected from the group consisting of vinblastine N-oxide, desacetyl vinblastine N-oxide, vinorelbine N-oxide, vincristine N-oxide and vinflunine N-oxide, or a pharmaceutically acceptable salt thereof.

In certain embodiments, a metronomic dosing regime for an N-oxide of vinca alkaloid or analog thereof comprises administration of the N-oxide at a dose below an established maximum tolerated dose (MTD) for the N-oxide, which upon repeated administration inhibits tumor growth and produces less toxic side effects as compared to administration of the maximum tolerated dose of the N-oxide. While not being bound to a particular mechanism, it is believed that metronomic dosing with an N-oxide of vinca alkaloid or analog thereof may target cells of the vasculature which form the blood vessels of the tumor as opposed to the tumor cells themselves. Accordingly, inhibition of tumor growth may result from the inability of the tumor cells to establish the functional microvasculature critical for tumor growth and dissemination.

An additional aspect of the present invention is a method for treating, ameliorating, or preventing hyperproliferative disorders in an animal comprising administering to the animal a therapeutically effective amount of a compound having Formula I in combination with one or more active agents or treatments. In one embodiment, the one or more active agent or treatment is a chemotherapeutic agent, a radiotherapeutic agent/treatment, an anti-angiogenesis agent, a vascular targeting agent, a hypoxia-inducible factor 1 (HIF1) inhibitor, an Hsp90 inhibitor, a tyrosine kinase inhibitor, a serine/threonine kinase inhibitor, a proteasome inhibitor, an HDAC inibitor, a caspase inducer, a CDK inhibitor, and a proapoptotic molecule. In another embodiment, the one or more active agent or treatment is used, has been used, or is known to be useful for the treatment of the hyperproliferative disorder.

A particular aspect of the present invention is a method for treating hyperproliferative disorders in an animal comprising administering to the animal a pharmaceutically acceptable amount of an N-oxide of vinca alkaloid or analog thereof, in combination with one or more other therapeutic agents, including topoisomerase 1 inhibitors. In other embodiments, topoisomerase 1 inhibitor can be any topoisomerase 1 inhibitor which is used, has been used, or is known to be useful for the treatment of hyperproliferative disorders. Examples of topoisomerase 1 inhibitors include camptothecin and its analogs such as those described in U.S. Pat. No. 6,350,756 (for example, 9-dimethylaminomethyl-10-hydroxycamptothecin (topotecan), 7-ethyl-10[4-(1-piperidino)-1-piperidino]carbonyloxycamptothecin (irinotecan), 9-aminocamptothecin, 10-aminocamptothecin, 10,11-methylenedioxycamptothecin and 7-ethyl-10-hyrdoxycamptothecin (SN-38)). In certain embodiments, the vinca alkaloid analog N-oxide used in the combination therapy is selected from the group consisting of vinblastine N-oxide, desacetyl vinblastine N-oxide, vinorelbine N-oxide, vincristine N-oxide and vinflunine N-oxide, or a pharmaceutically acceptable salt thereof. In other embodiments, the compound of Formula I is administered 1 mg/kg q3d×5 to 500 mg/kg q3d×5. In other embodiments, the compound of Formula I is administered 5 mg/kg q3d×5 to 50 mg/kg q3d×5.

In other embodiments, irinotecan, or a pharmaceutically acceptable salt thereof, is administered 50 mg/m$^2$ to 500 mg/m$^2$ once weekly, once every two weeks or once every three weeks.

In one embodiment, the method of treating, ameliorating, or preventing hyperproliferative disorder in an animal comprises administering to the animal a therapeutically effective amount of vinca alkaloid N-oxide or analog thereof. In particular embodiments, the vinca alkaloid analog N-oxide is selected from the group consisting of vinblastine N-oxide, desacetyl vinblastine N-oxide, vinorelbine N-oxide, vincristine N-oxide and vinflunine N-oxide, or a pharmaceutically acceptable salt thereof, in combination with one or more active agents or treatments, for example, chemotherapeutic agents or radiotherapeutic agents/treatments.

In preferred embodiments of the invention, the one or more chemotherapeutic agents can be any chemotherapeutic agent which is used, has been used, or is known to be useful for the treatment of hyperproliferative disorders.

In preferred embodiments of the invention, the one or more radiotherapeutic agents or treatments can be external-beam radiation therapy, brachytherapy, thermotherapy, radiosurgery, charged-particle radiotherapy, neutron radiotherapy, photodynamic therapy, or radionuclide therapy.

In one embodiment of the invention, the compound having Formula I can be administered prior to, during, and/or beyond administration of the one or more chemotherapeutic agents or radiotherapeutic agents or treatments. In another embodiment of the invention, the method of administering a compound having Formula I in combination with one or more chemotherapeutic agents or radiotherapeutic agents or treatments is repeated more than once.

The combination of a compound having Formula I and one or more chemotherapeutic agents or radiotherapeutic agents or treatments of the present invention will have additive potency or an additive therapeutic effect. The invention also encompasses synergistic combinations where the therapeutic efficacy is greater than additive. Preferably, such combinations will reduce or avoid unwanted or adverse effects. In certain embodiments, the combination therapies encompassed by the invention will provide an improved overall therapy relative to administration of a compound having Formula I or any chemotherapeutic agent or radiotherapeutic agent or treatment alone. In certain embodiments, doses of existing or experimental chemotherapeutic agents or radiotherapeutic agents or treatments will be reduced or administered less frequently which will increase patient compliance, thereby improving therapy and reducing unwanted or adverse effects.

Further, the methods of the invention will be useful not only with previously untreated patients but also will be useful in the treatment of patients partially or completely refractory to current standard and/or experimental cancer therapies, including but not limited to radiotherapies, chemotherapies, and/or surgery. In a preferred embodiment, the invention will provide therapeutic methods for the treatment or amelioration of hyperproliferative disorders that have been shown to be or may be refractory or non-responsive to other therapies.

While not wishing to be bound by any theory, it is believed that some of the N-oxide compounds of the invention will function as prodrugs with greatly diminished cytotoxicity. It is believed that these N-oxide compounds will be activated under hypoxic conditions within the target tissues (i.e., reduced at the nitrogen atom), followed by inhibition of microtube formation in the mitotic spindle resulting in arrest of dividing cells at the metaphase stage, diminishing cells' ability to replicate. Other N-oxide compounds of the invention may have intrinsic cytotoxic activity. Since a number of pathological tissues have significant hypoxic components which promote hyperproliferation, it is believed that this portion of tissue will be preferentially targeted.

Because lower doses of chemotheraputic agents generally pose lower risks of side effects, it would be advantageous if lower doses of the agents can be administered without compromising its efficacy. It is believed that the N-oxide compounds, when used in combination with certain chemotherapeutic agents, will prevent or ameliorate side effects induced by or associated with the chemotheraputic agent by decreasing the effective dose of the agents than would otherwise be possible without the use of the N-oxide compounds.

BRIEF DESCRIPTION OF THE DRAWINGS/FIGURES

Figure 5:
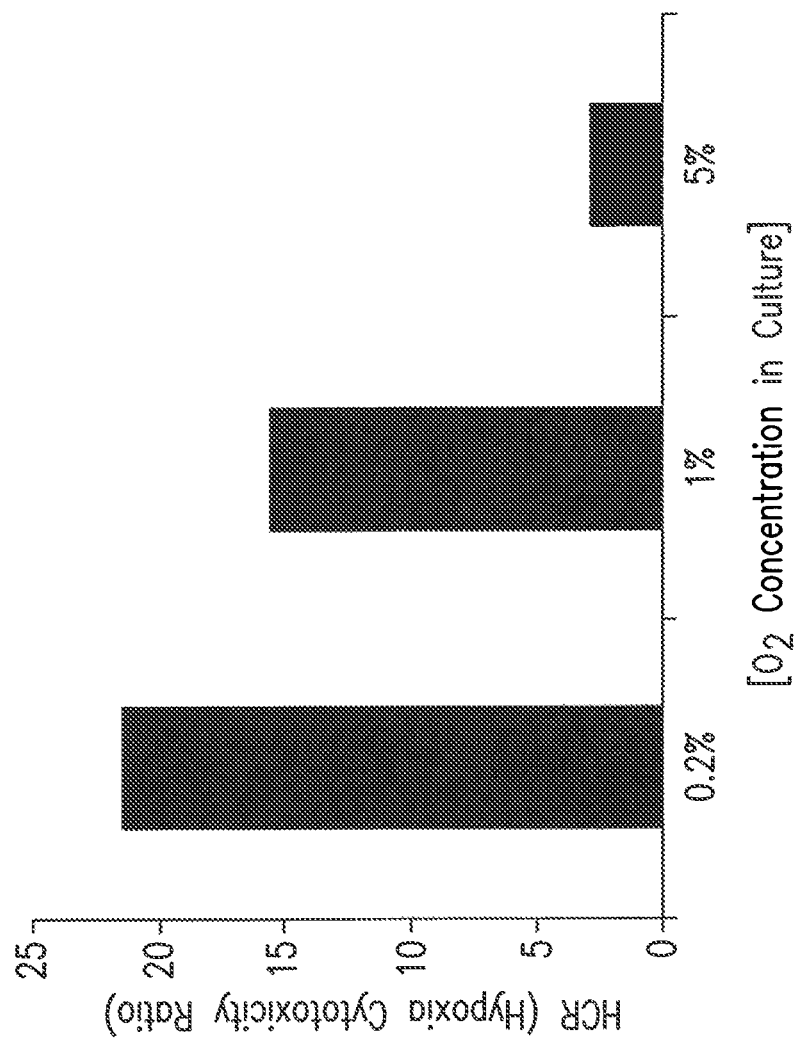

FIG. 5 shows activation of cytotoxicity of Vinblastine N-oxide against H460 lung carcinoma cells is oxygen dependent. The HCR was calculated as the $IC_{50}$ under normoxic conditions/$IC_{50}$ hypoxic conditions FIGS. 6A-6D show chromatograms from LC/MS-MS analysis of the extracellular medium from 200 nM vinblastine N-oxide treated H460 lung adenocarcinoma tumor cells demonstrating that vinblastine N-oxide is converted to vinblastine (parent drug) following hypoxia exposure.

Figure 7A:
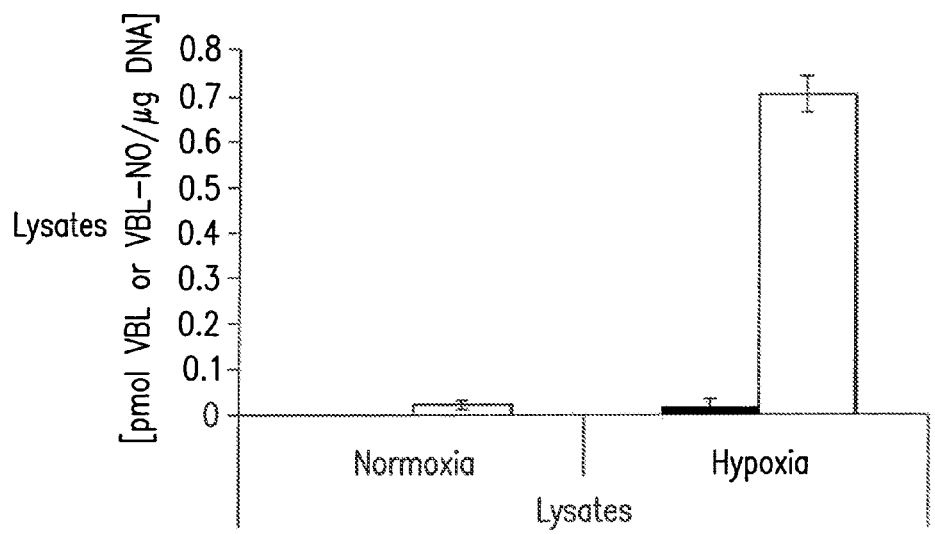
Figure 7B:
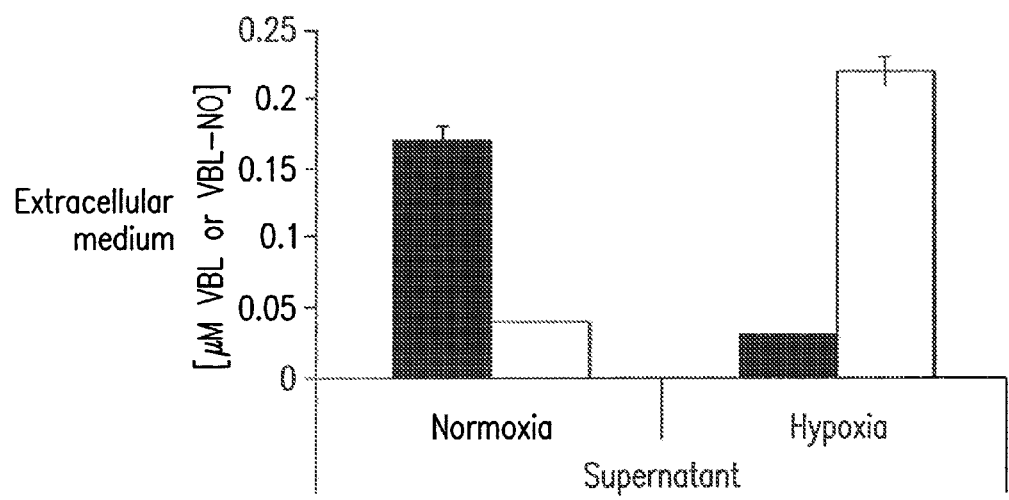

FIGS. 7A and 7B show LC/MS-MS analysis of vinblastine N-oxide (filled bars) or bioreduced vinblastine (unfilled bars) from the lysates (7A) or extracellular medium (7B) of H460 cells treated with 200 nM vinblastine N-oxide exposed to normoxic or hypoxic conditions.

Figure 8A:
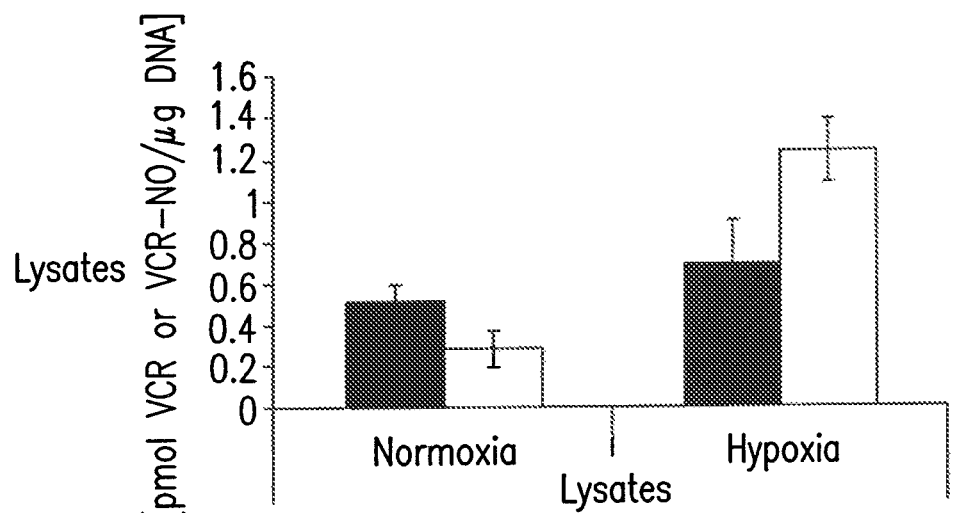
Figure 8B:
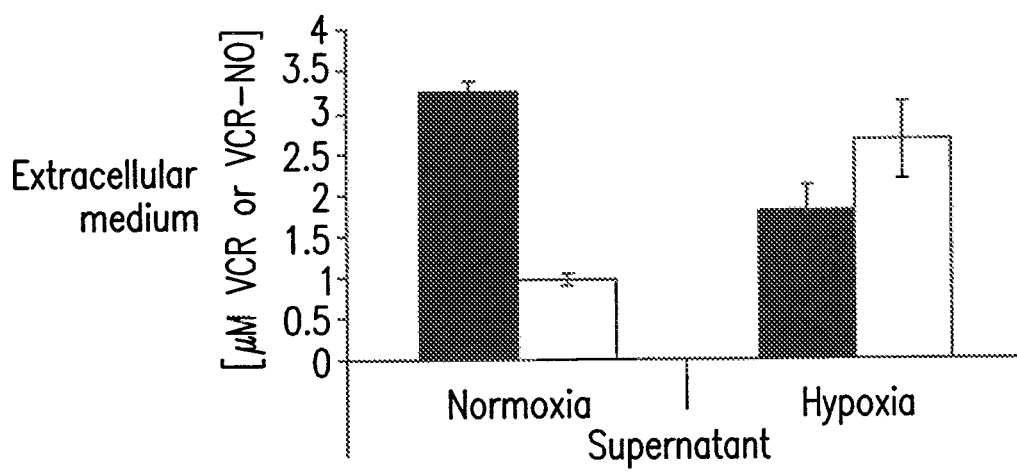

FIGS. 8A and 8B show LC/MS-MS analysis of vincristine N-oxide (filled bars) or bioreduced vincristine (unfilled bars) from the lysates (8A) or extracellular medium (8B) of H460 cells treated with 7 mM vincristine N-oxide exposed to normoxic or hypoxic conditions.

Figure 9:
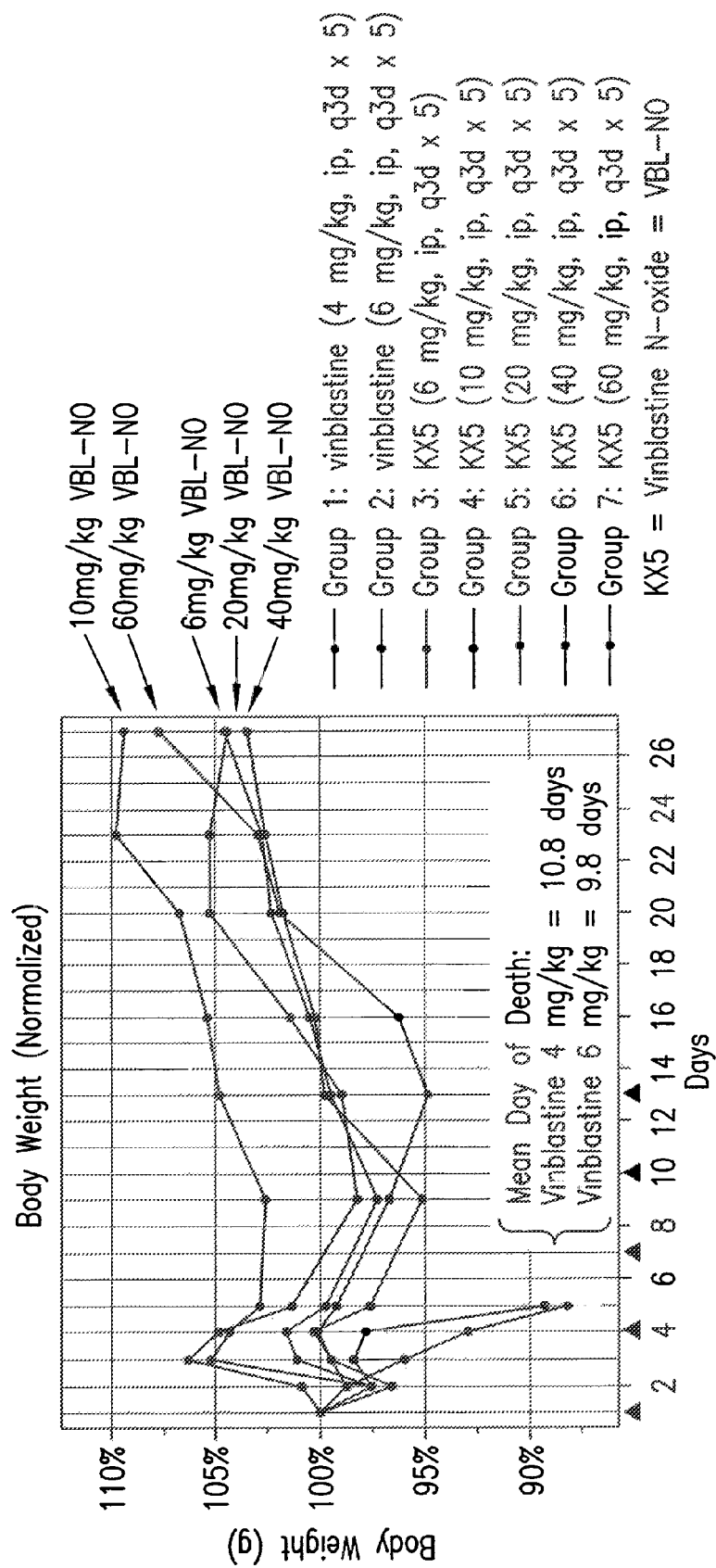

FIG. 9 shows the effects of vinblastine N-oxide analog (VBL-NO) or vinblastine treatment on mean percentage change in body weight loss in immunodeficient mice (n=5 group). All agents were i.p. administered on a q3dx5 schedule at the indicated dosages.

Figure 10:
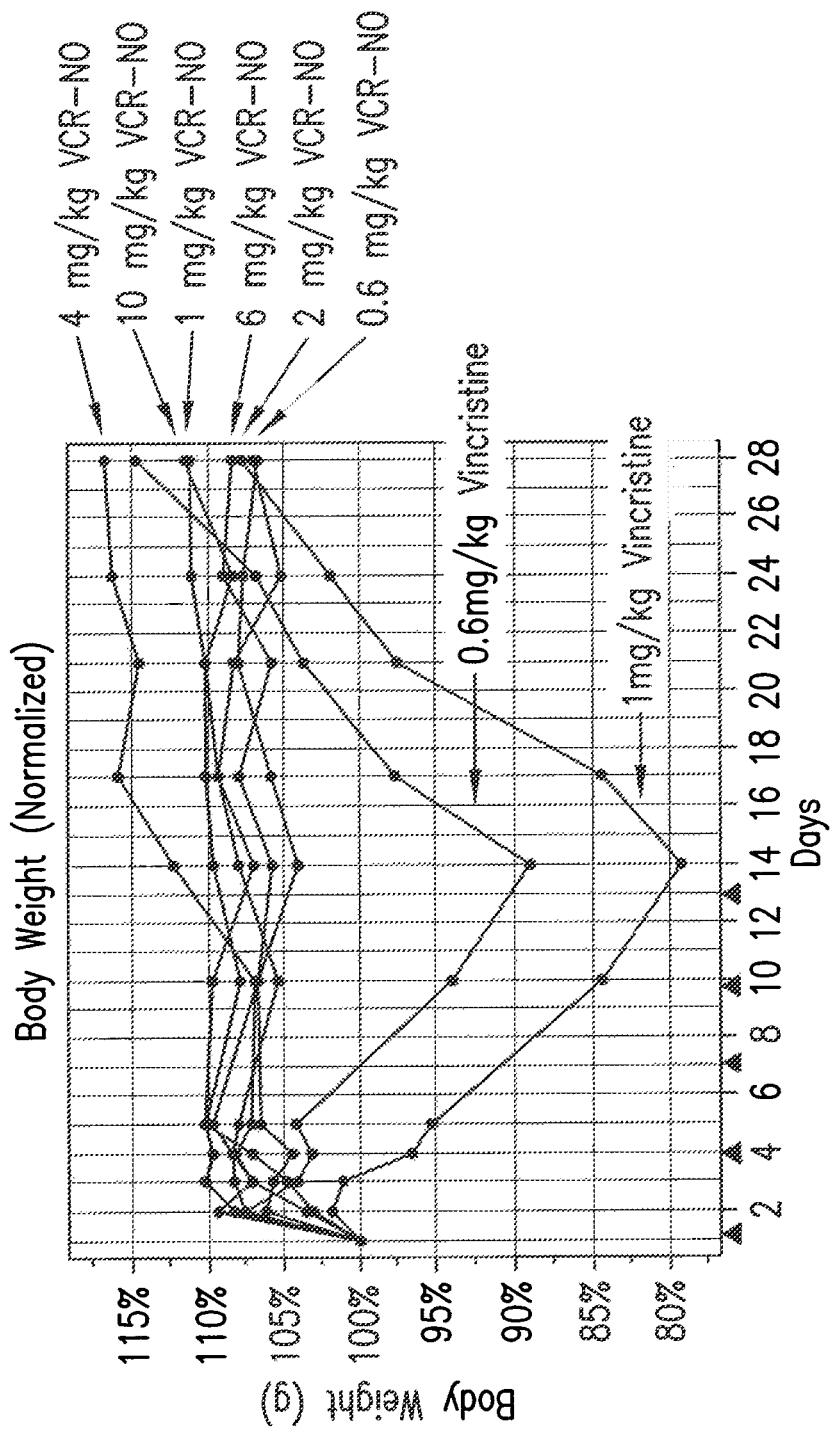

FIG. 10 shows the effects of vincristine N-oxide analog (VCR-NO) or vincristine sulfate treatment on mean percentage change in body weight loss in tumor-bearing immunodeficient mice (n=5 group). All agents were i.v. administered on a q3dx5 schedule at the indicated dosages.

Figure 11:
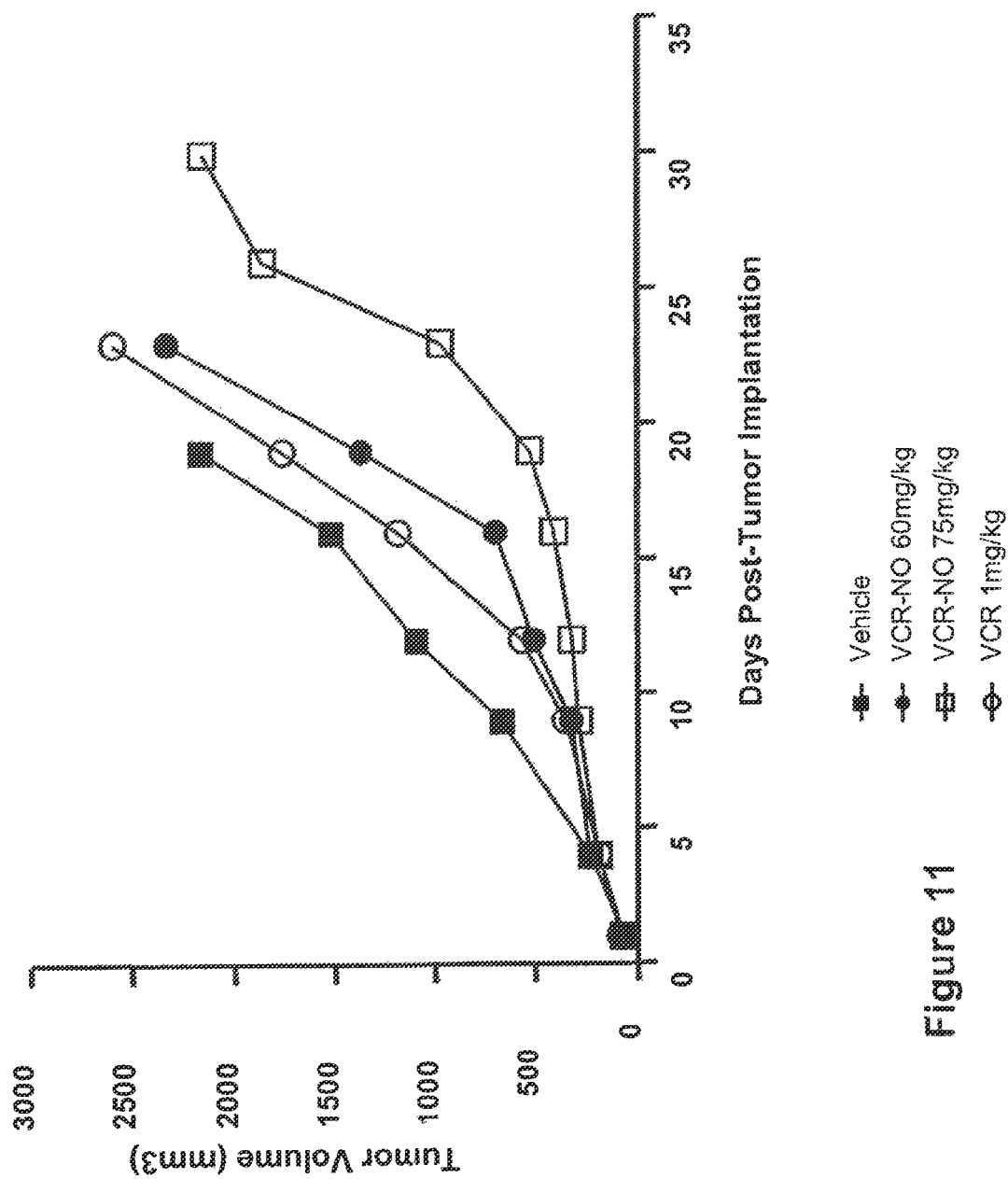
Figure 12:
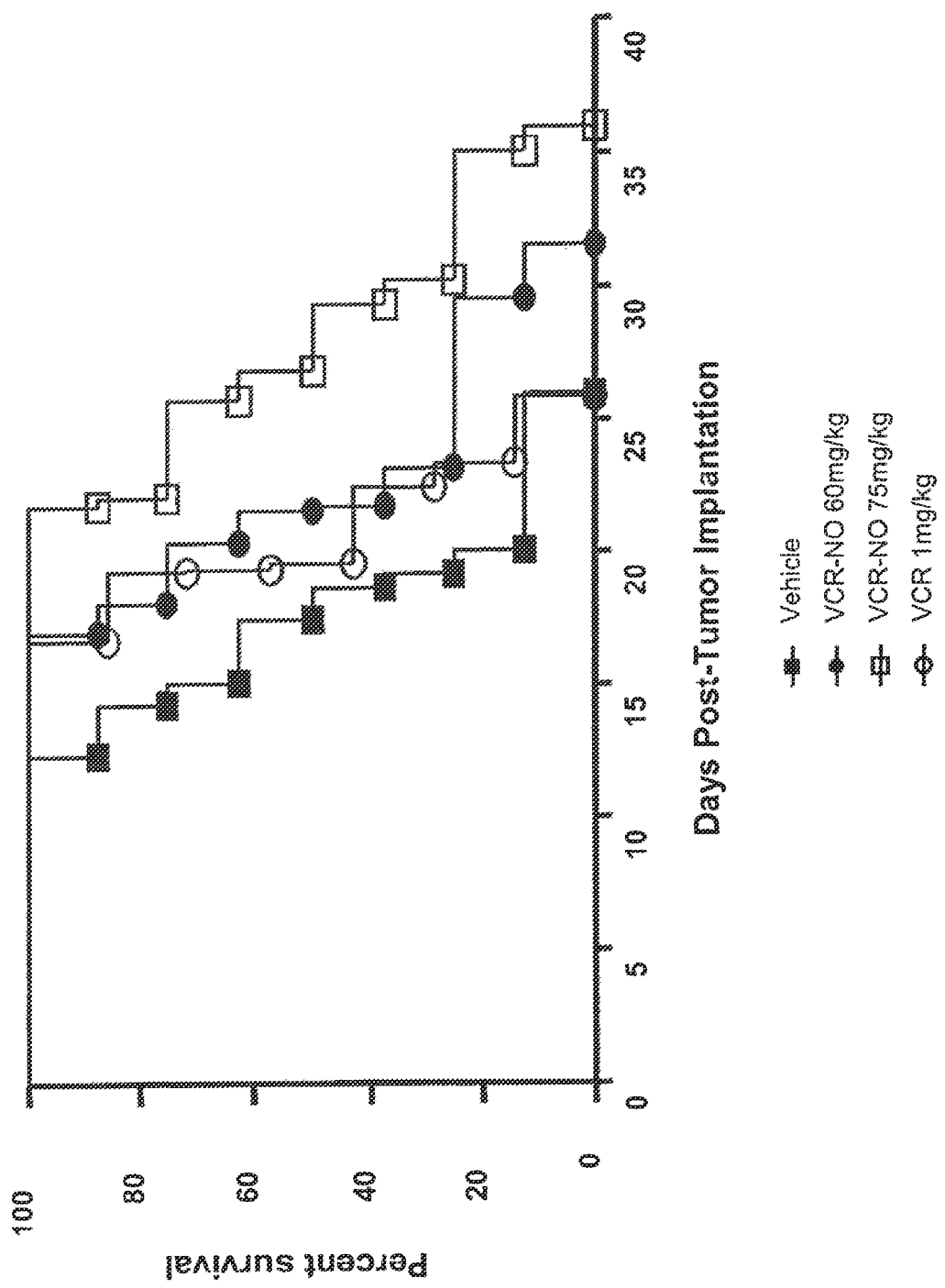

FIG. 11 shows efficacy of vincristine N-oxide analog (VCR-NO) or vincristine (VCR) in the L1210 murine leukemia model (n=8) as determined by Tumor Growth Delay. All agents were i.v. administered on a q3dx5 schedule (d. 1, 4, 7, 10, 13) at the indicated dosages.
Tumor Growth Delay
VCR-NO 60 mg/kg=20% (P<0.05);
VCR-NO 75 mg/kg=49% (P<0.01);
Vincristine 1 mg/kg=8% (NS FIG. 12 shows efficacy of vincristine N-oxide analog (VCR-NO) or vincristine (VCR) in the L1210 murine leukemia model (n=8) as determined by Kaplan Meier Survival analysis. All agents were i.v. administered on a q3dx5 schedule (d. 1, 4, 7, 10, 13) at the indicated dosages.
Median Survival (days):
Vehicle=18.1;
VCR-NO 60 mg/kg=21.7;
VCR-NO 75 mg/kg=28.2;
Vincristine 1 mg/kg=19.6

Figure 13:
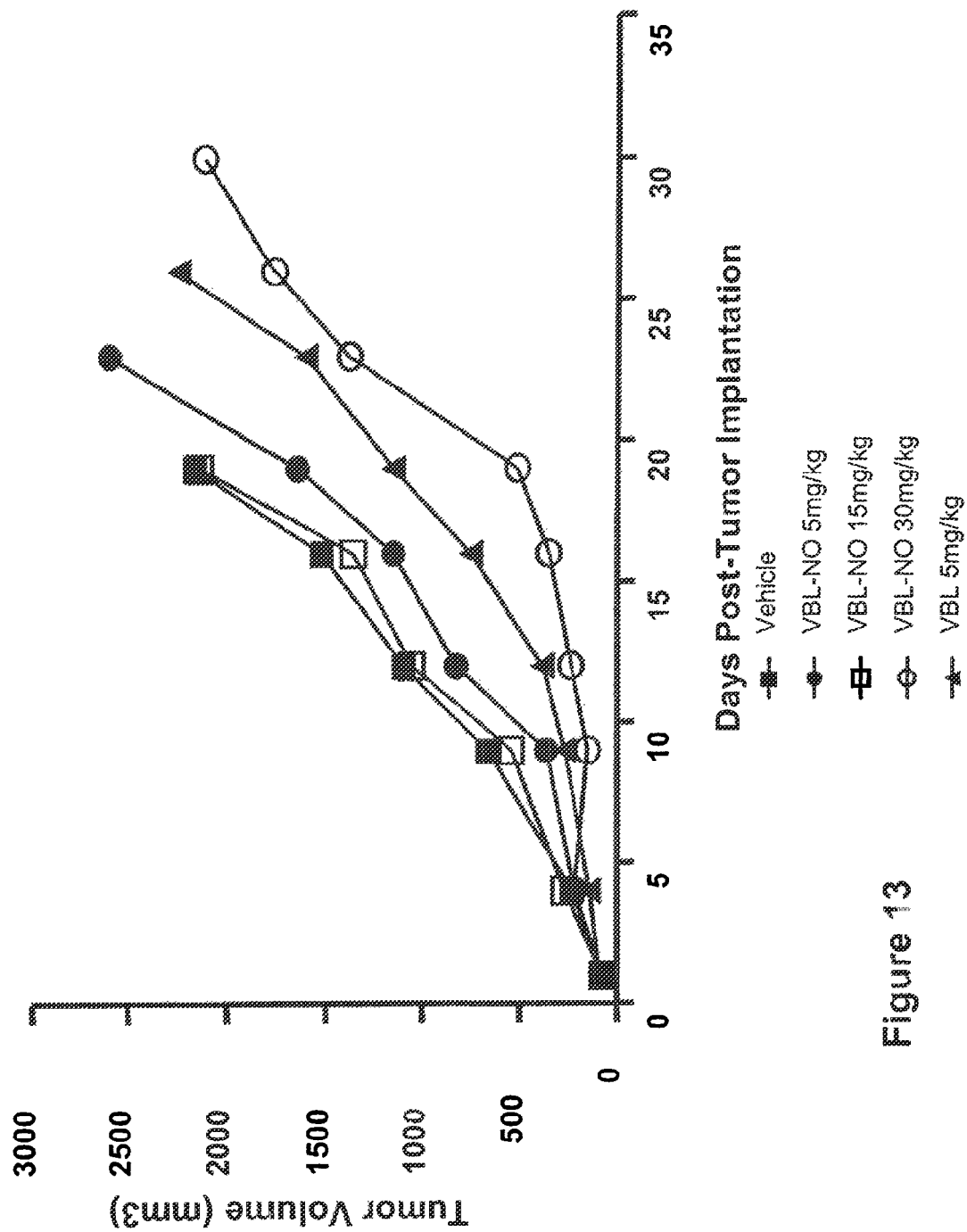

FIG. 13 shows efficacy of vinblastine N-oxide analog (VBL-NO) or vinblastine (VBL) in the L1210 murine leukemia model (n=8) as determined by Tumor Growth Delay. All agents were i.v. administered on a q3dx5 schedule (d. 1, 4, 7, 10, 13) at the indicated dosages.
Tumor Growth Delay:
VBL-NO 5 mg/kg=18% (NS);
VBL-NO 15 mg/kg=0% (NS);
VBL-NO 30 mg/kg=41% (P<0.01);
Vinblastine 5 mg/kg=34% (P<0.05)

Figure 14:
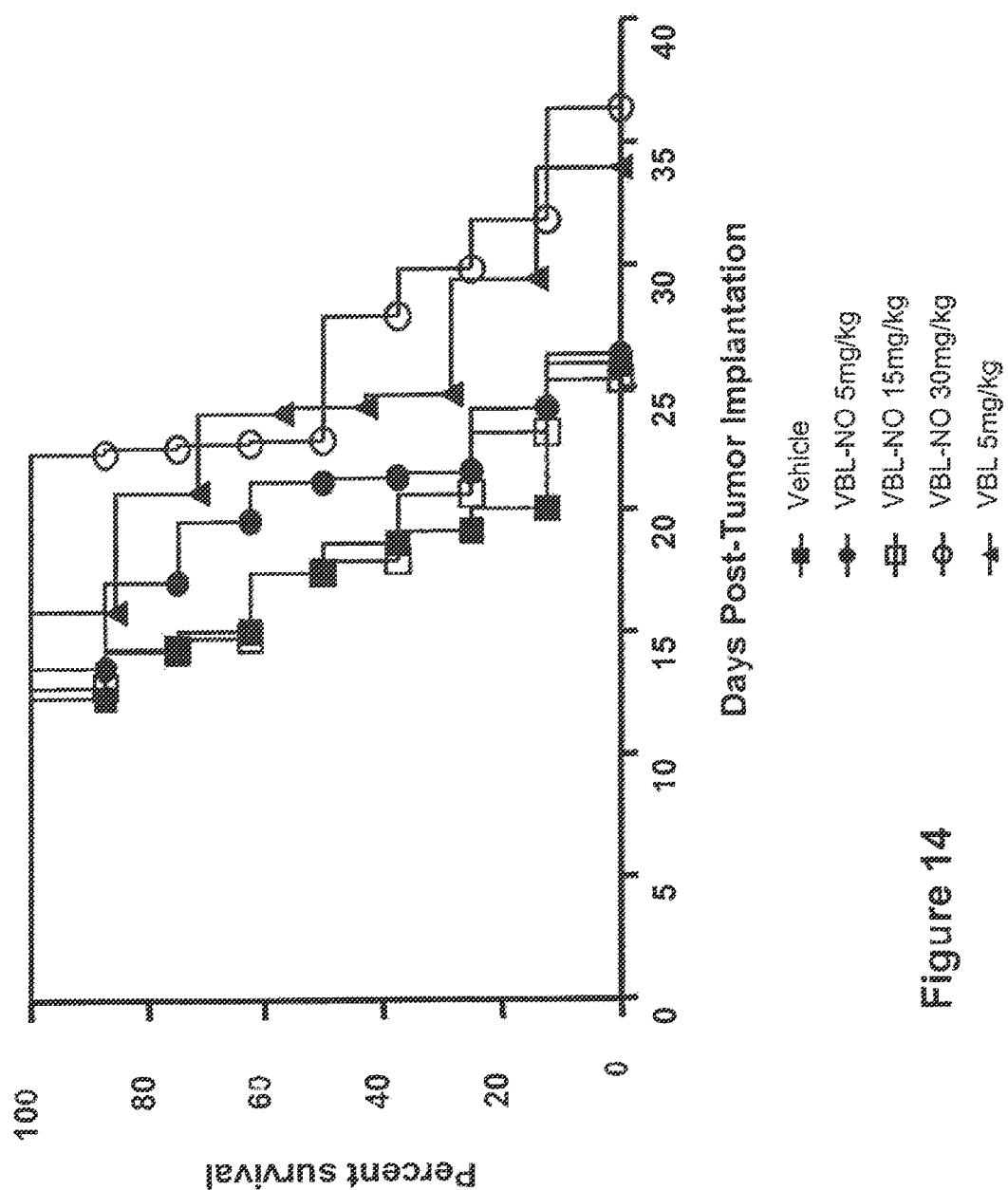

FIG. 14 shows efficacy of vinblastine N-oxide analog (VBL-NO) or vinblastine (VBL) in the L1210 murine leukemia model (n=8) as determined by Kaplan Meier Survival analysis. All agents were i.v. administered on a q3dx5 schedule (d. 1, 4, 7, 10, 13) at the indicated dosages.
Median Survival (days):
Vehicle=18.1;
VBL-NO 5 mg/kg=21.3;
VBL-NO 15 mg/kg=17.8;
VBL-NO 30 mg/kg=25.5;
Vinblastine 5 mg/kg=24.3

Figure 15:
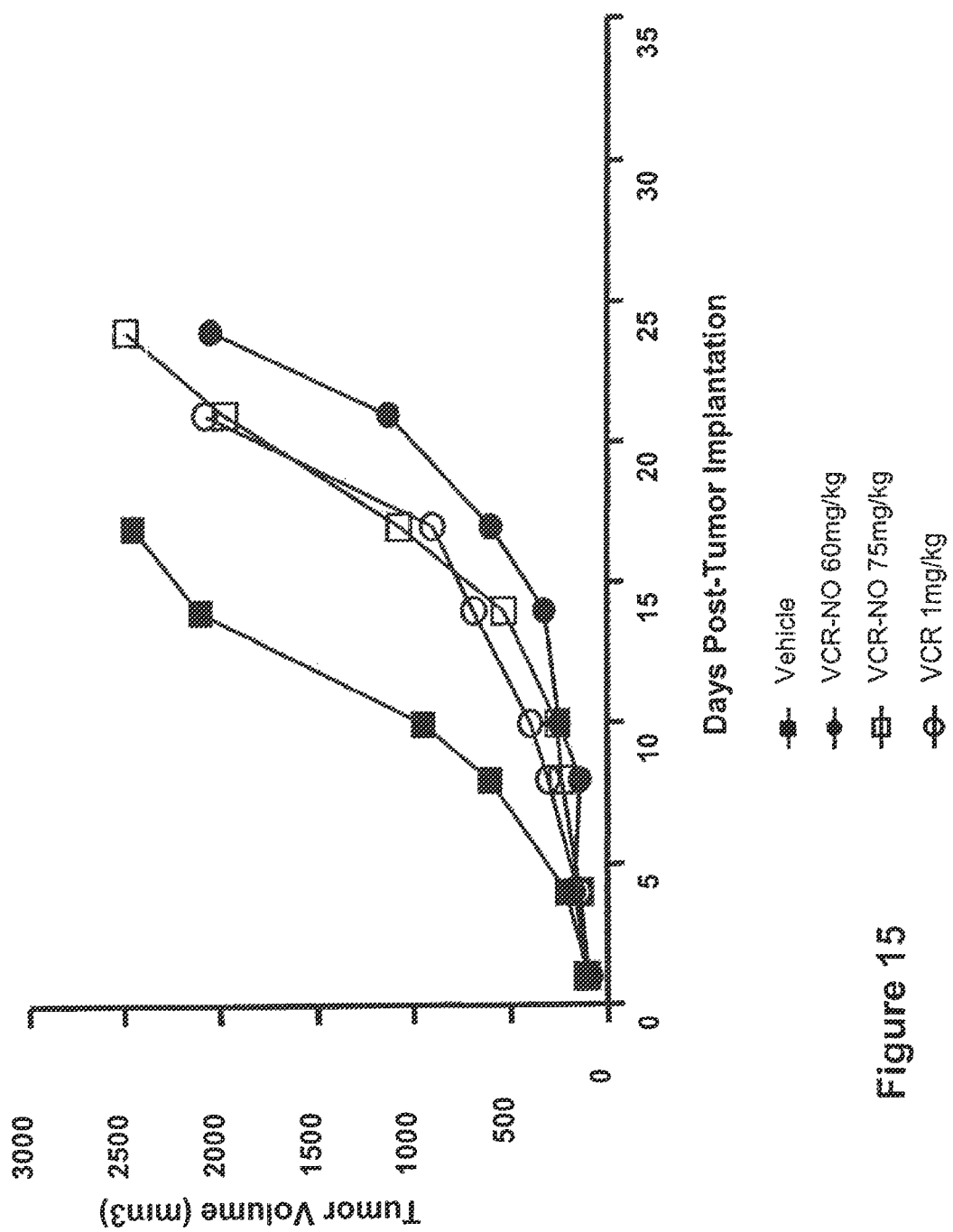

FIG. 15 shows efficacy of vincristine N-oxide analog (VCR-NO) or vincristine (VCR) in the P388 murine leukemia model (n=8) as determined by Tumor Growth Delay. All agents were i.v. administered on a q3dx5 schedule (d. 1, 4, 7, 10, 13) at the indicated dosages.
Tumor Growth Delay:
VCR-NO 60 mg/kg=76% (P<0.001);
VCR-NO 75 mg/kg=54% (P<0.001);
Vincristine 1 mg/kg=54% (P<0.001)

Figure 16:
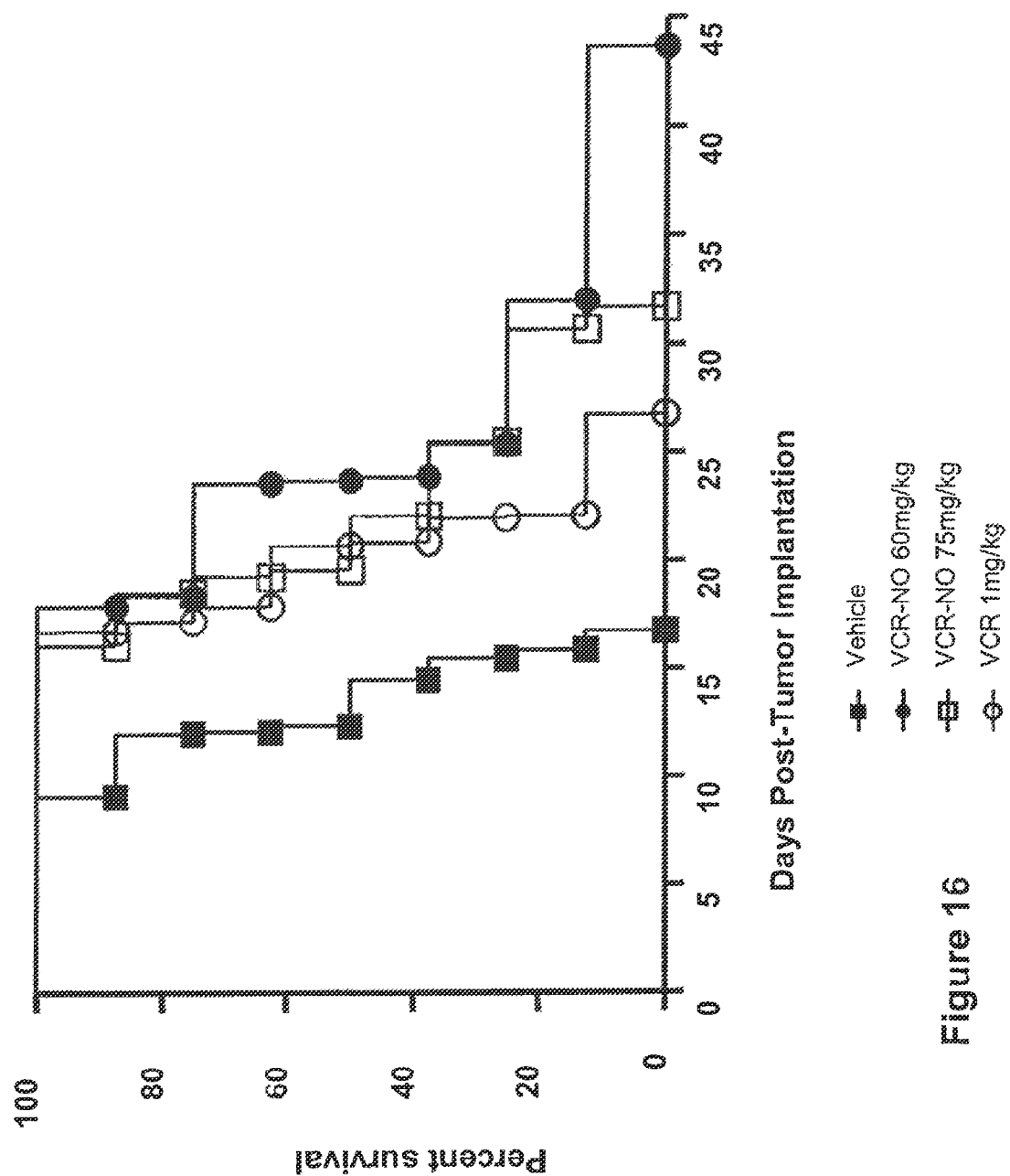

FIG. 16 shows efficacy of vincristine N-oxide analog (VCR-NO) or vincristine (VCR) in the P388 murine leukemia model (n=8) as determined by Kaplan Meier Survival analysis. All agents were i.v. administered on a q3dx5 schedule (d. 1, 4, 7, 10, 13) at the indicated dosages.
Median Survival (days):
Vehicle=13.5;
VCR-NO 60 mg/kg=23.8;
VCR-NO 75 mg/kg=20.9;
Vincristine 1 mg/kg=20.8

Figure 17:
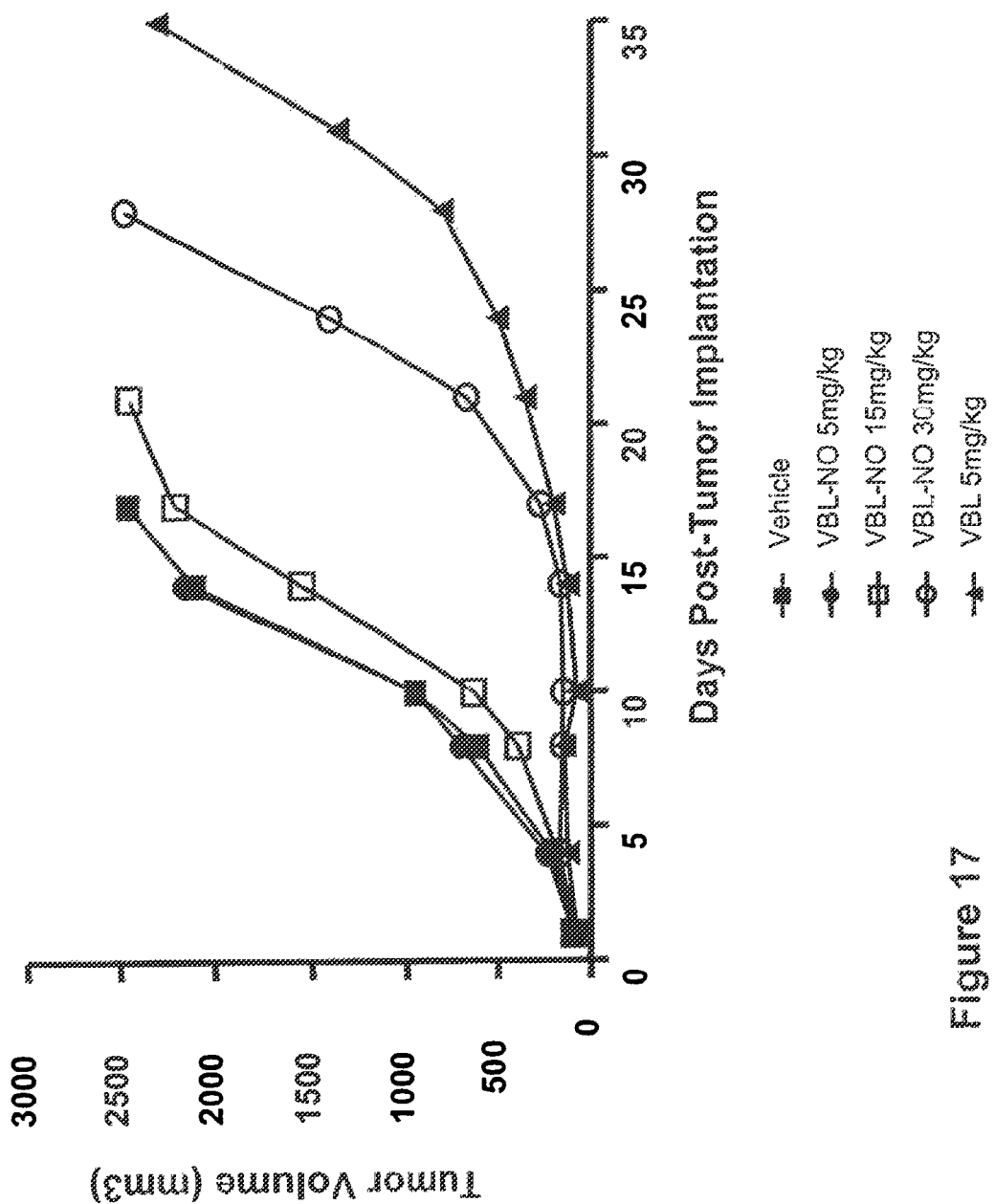

FIG. 17 shows efficacy of vinblastine N-oxide analog (VBL-NO) or vinblastine (VBL) in the P388 murine leukemia model (n=8) as determined by Tumor Growth Delay. All agents were i.v. administered on a q3dx5 schedule (d. 1, 4, 7, 10, 13) at the indicated dosages.
Tumor Growth Delay:
VBL-NO 5 mg/kg=0% (NS);
VBL-NO 15 mg/kg=24% (P<0.05);
VBL-NO 30 mg/kg=92% (P<0.001);
Vinblastine 5 mg/kg=149% (P<0.001)

Figure 18:
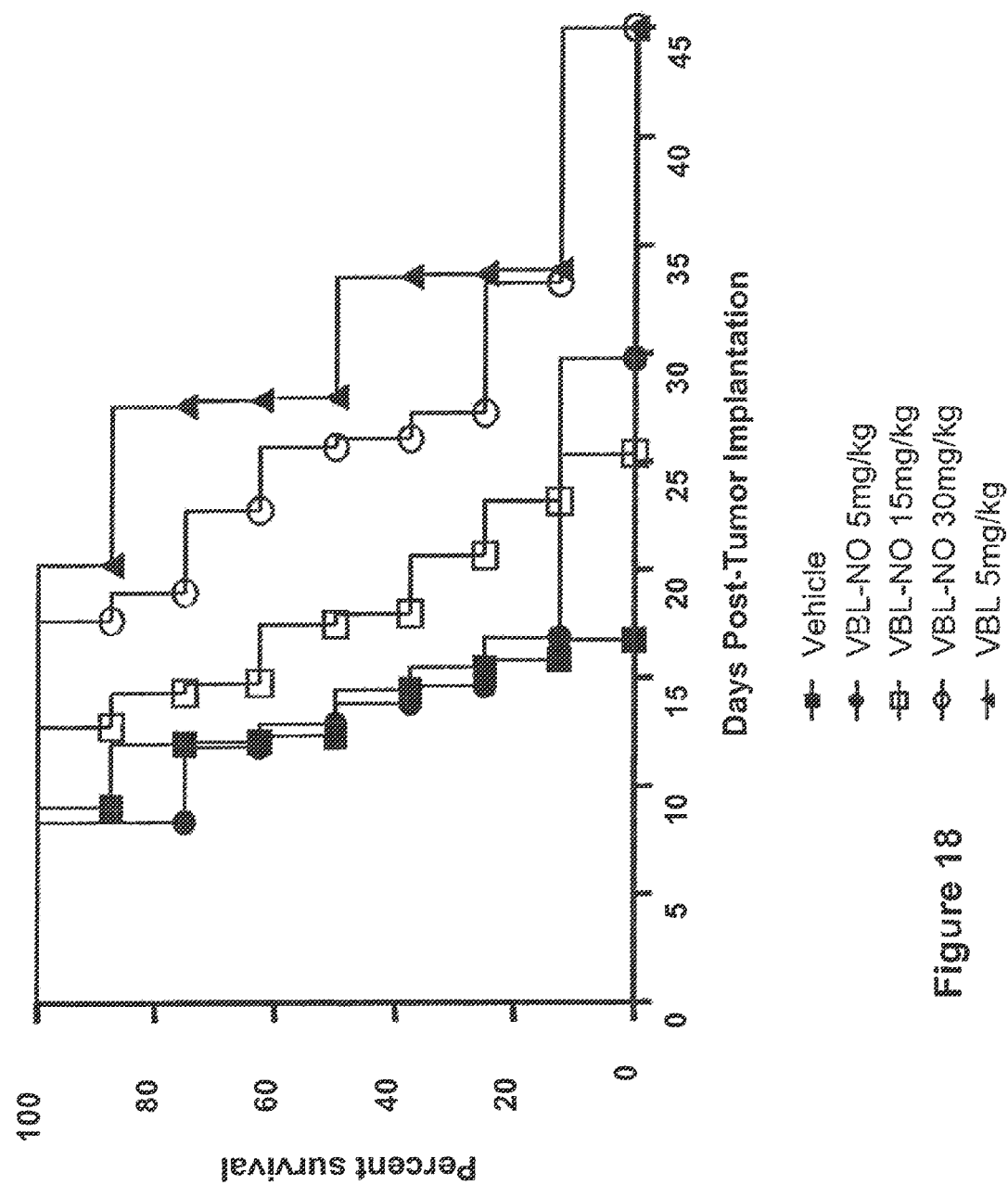

FIG. 18 shows efficacy of vinblastine N-oxide analog (VBL-NO) or vinblastine (VBL) in the P388 murine leukemia model (n=8) as determined by Kaplan Meier Survival analysis. All agents were i.v. administered on a q3d×5 schedule (d. 1, 4, 7, 10, 13) at the indicated dosages.
Median Survival (days):
Vehicle=13.5;
VBL-NO 5 mg/kg=13.4;
VBL-NO 15 mg/kg=17.8;
VBL-NO 30 mg/kg=25.9;
Vinblastine 5 mg/kg=30.8

Figure 19:
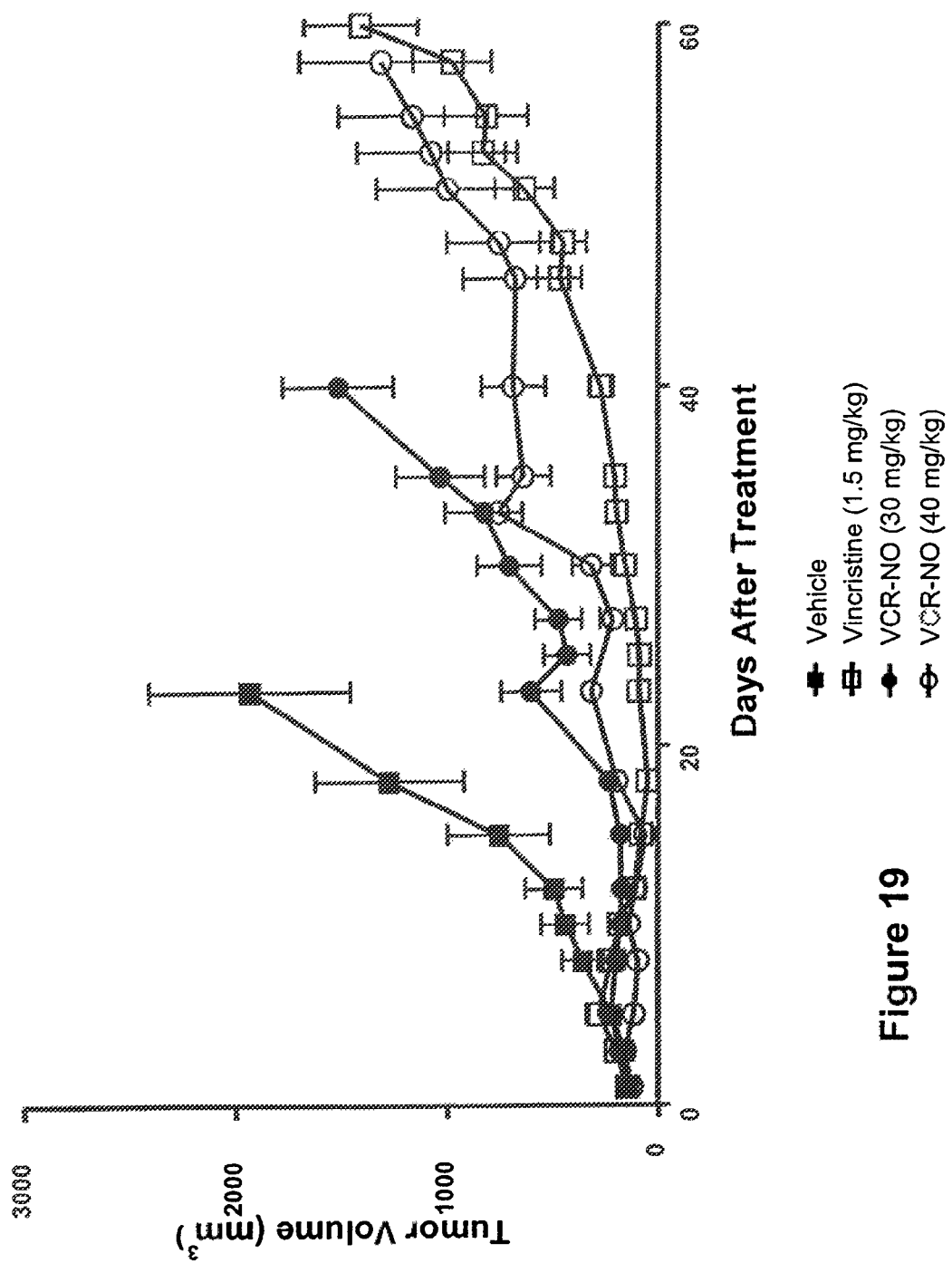

FIG. 19 shows efficacy of vincristine N-oxide analog (VCR-NO) or vincristine (VCR) in the K562 myelogenous leukemia xenograft model in nude mice (n=10) as determined by Tumor Growth Inhibition. All agents were i.v. administered on a q3d×5 schedule (d. 1, 4, 7, 10, 13) at the indicated dosages.
Tumor Growth Inhibition:
VCR-NO 30 mg/kg=69% ($P<0.01$);
VCR-NO 40 mg/kg=84% ($P<0.01$);
Vincristine 1.5 mg/kg=95% ($P<0.01$)

Figure 20:
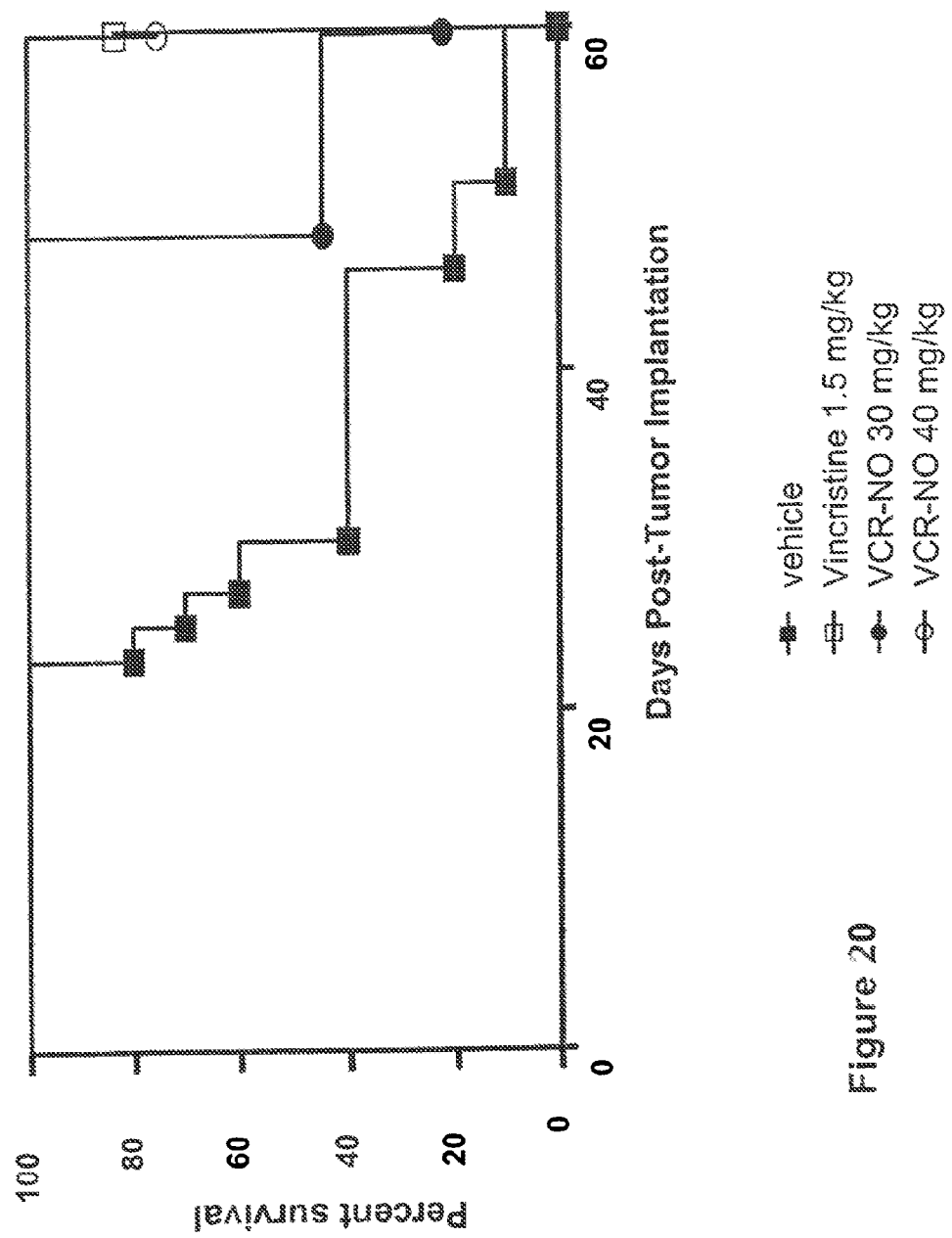

FIG. 20 shows efficacy of vincristine N-oxide analog (VCR-NO) or vincristine (VCR) in the K562 myelogenous leukemia xenograft model in nude mice (n=10) as determined by Kaplan Meier Survival analysis. All agents were i.v. administered on a q3d×5 schedule (d. 1, 4, 7, 10, 13) at the indicated dosages.
Median Survival (days):
Vehicle=30;
VCR-NO 30 mg/kg=48;
VCR-NO 40 mg/kg=60;
Vincristine 1.5 mg/kg=60

Figure 21:
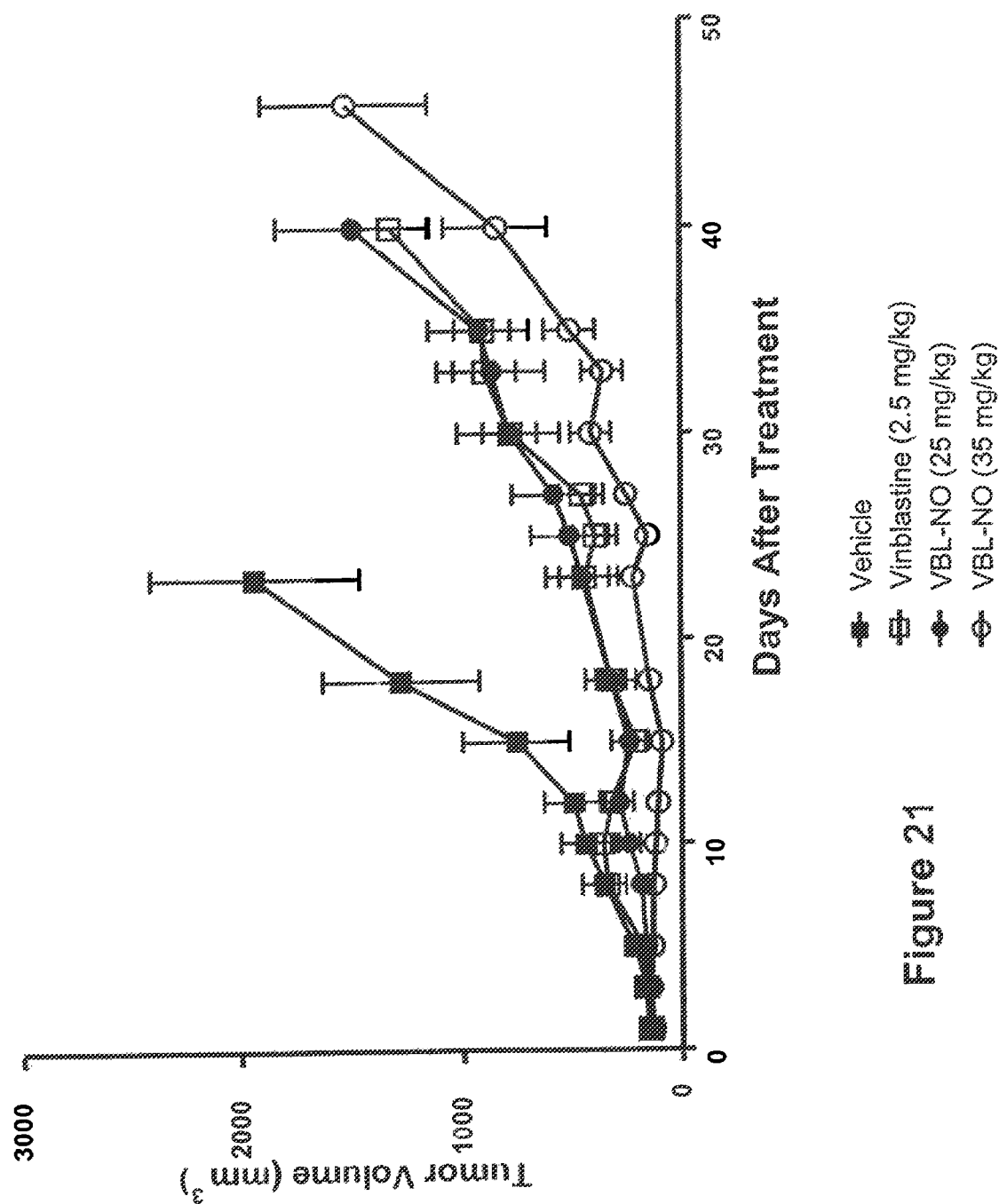

FIG. 21 shows efficacy of vinblastine N-oxide analog (VBL-NO) or vinblastine (VBL) in the K562 myelogenous leukemia xenograft model in nude mice (n=10) as determined by Tumor Growth Inhibition. All agents were i.v. administered on a q3d×5 schedule (d. 1, 4, 7, 10, 13) at the indicated dosages.
Tumor Growth Inhibition:
VBL-NO 25 mg/kg=77% ($P<0.01$);
VBL-NO 35 mg/kg=89% ($P<0.01$);
Vinblastine 2.5 mg/kg=77% ($P<0.01$)

Figure 22:
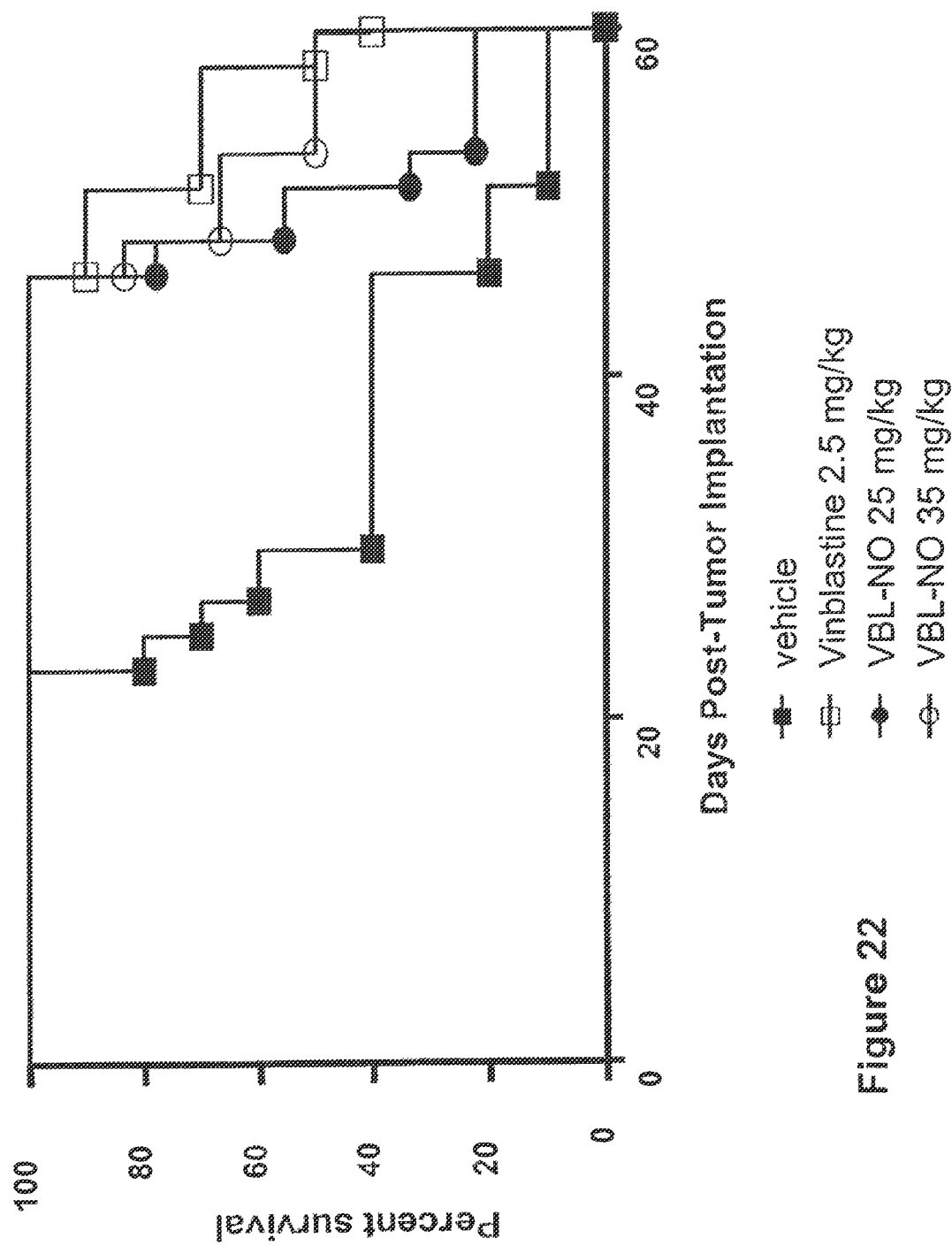

FIG. 22 shows efficacy of vinblastine N-oxide analog (VBL-NO) or vinblastine (VBL) in the K562 myelogenous leukemia xenograft model in nude mice (n=10) as determined by Kaplan Meier Survival analysis. All agents were i.v. administered on a q3d×5 schedule (d. 1, 4, 7, 10, 13) at the indicated dosages.
Median Survival (days):
Vehicle=30;
VBL-NO 25 mg/kg=51;
VBL-NO 35 mg/kg=57;
Vinblastine 2.5 mg/kg=60

Figure 23:
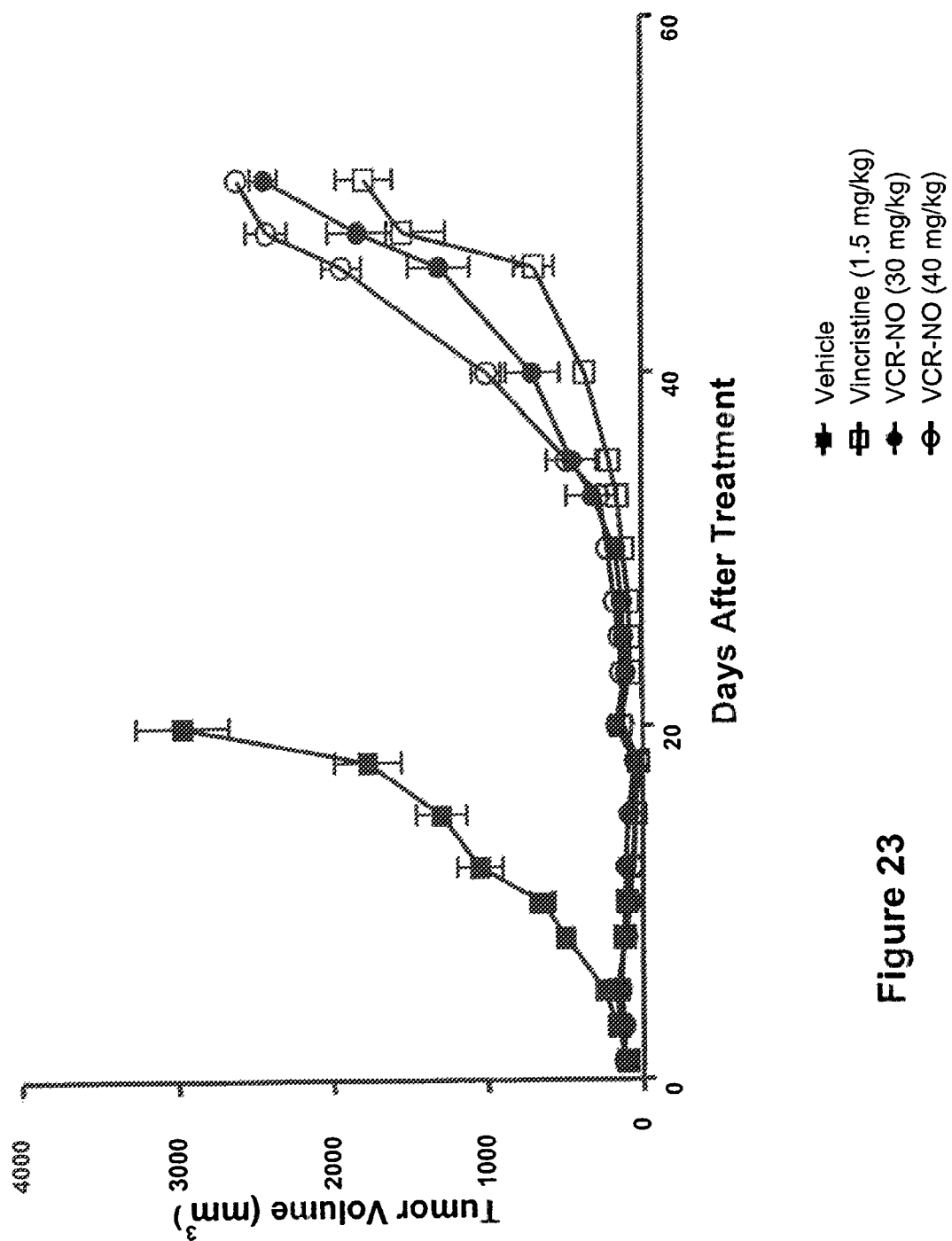
Figure 24:
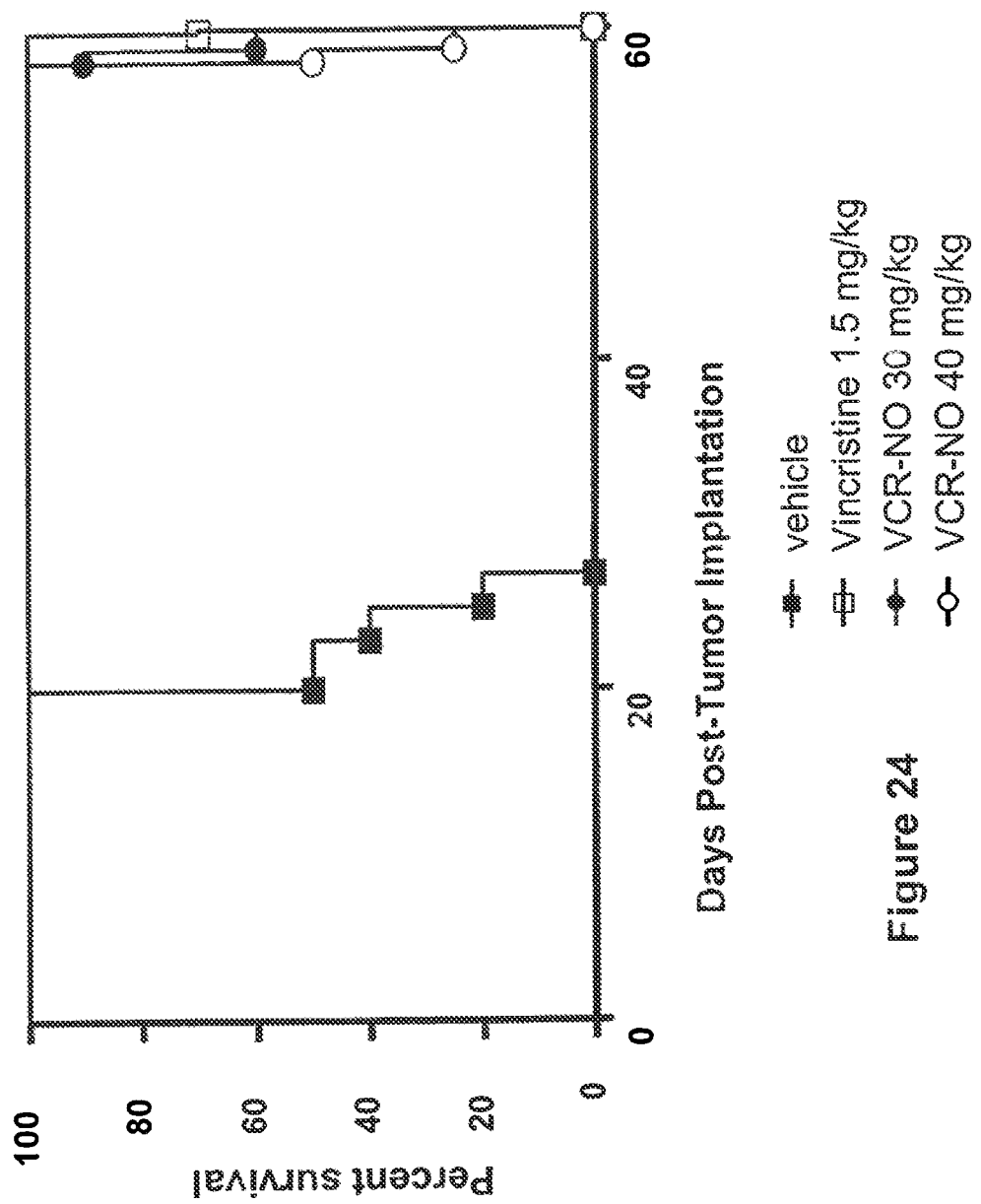

FIG. 23 shows efficacy of vincristine N-oxide analog (VCR-NO) or vincristine (VCR) in the HL60 promyelocytic leukemia xenograft model in nude mice (n=10) as determined by Tumor Growth Inhibition. All agents were i.v. administered on a q3d×5 schedule (d. 1, 4, 7, 10, 13) at the indicated dosages.
Tumor Growth Inhibition:
VCR-NO 30 mg/kg=94% ($P<0.01$);
VCR-NO 40 mg/kg=96% ($P<0.01$);
Vincristine 1.5 mg/kg=95% ($P<0.01$ FIG. 24 shows efficacy of vincristine N-oxide analog (VCR-NO) or vincristine (VCR) in the HL60 promyelocytic leukemia xenograft model in nude mice (n=10) as determined by Kaplan Meier Survival analysis. All agents were i.v. administered on a q3d×5 schedule (d. 1, 4, 7, 10, 13) at the indicated dosages.
Median Survival (days):
Vehicle=21.5;
VCR-NO 30 mg/kg=60;
VCR-NO 40 mg/kg=58;
Vincristine 1.5 mg/kg=60

Figure 25:
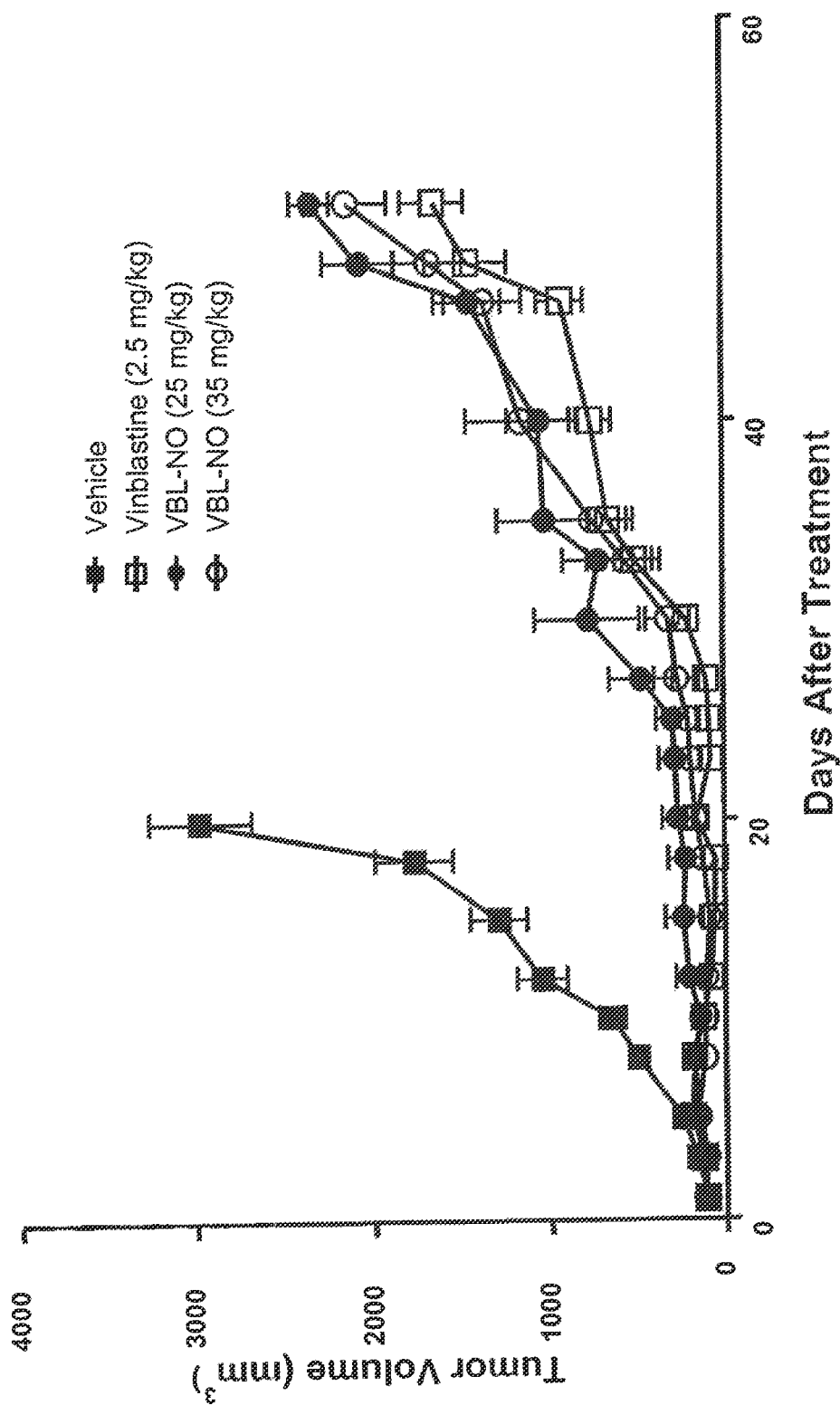

FIG. 25 shows efficacy of vinblastine N-oxide analog (VBL-NO) or vinblastine (VBL) in the HL60 promyelocytic leukemia xenograft model in nude mice (n=10) as determined by Kaplan Meier Survival analysis. All agents were i.v. administered on a q3d×5 schedule (d. 1, 4, 7, 10, 13) at the indicated dosages.
Tumor Growth Inhibition:
VBL-NO 25 mg/kg=91% ($P<0.01$);
VBL-NO 35 mg/kg=94% ($P<0.01$);
Vinblastine 2.5 mg/kg=95% ($P<0.01$)

Figure 26:
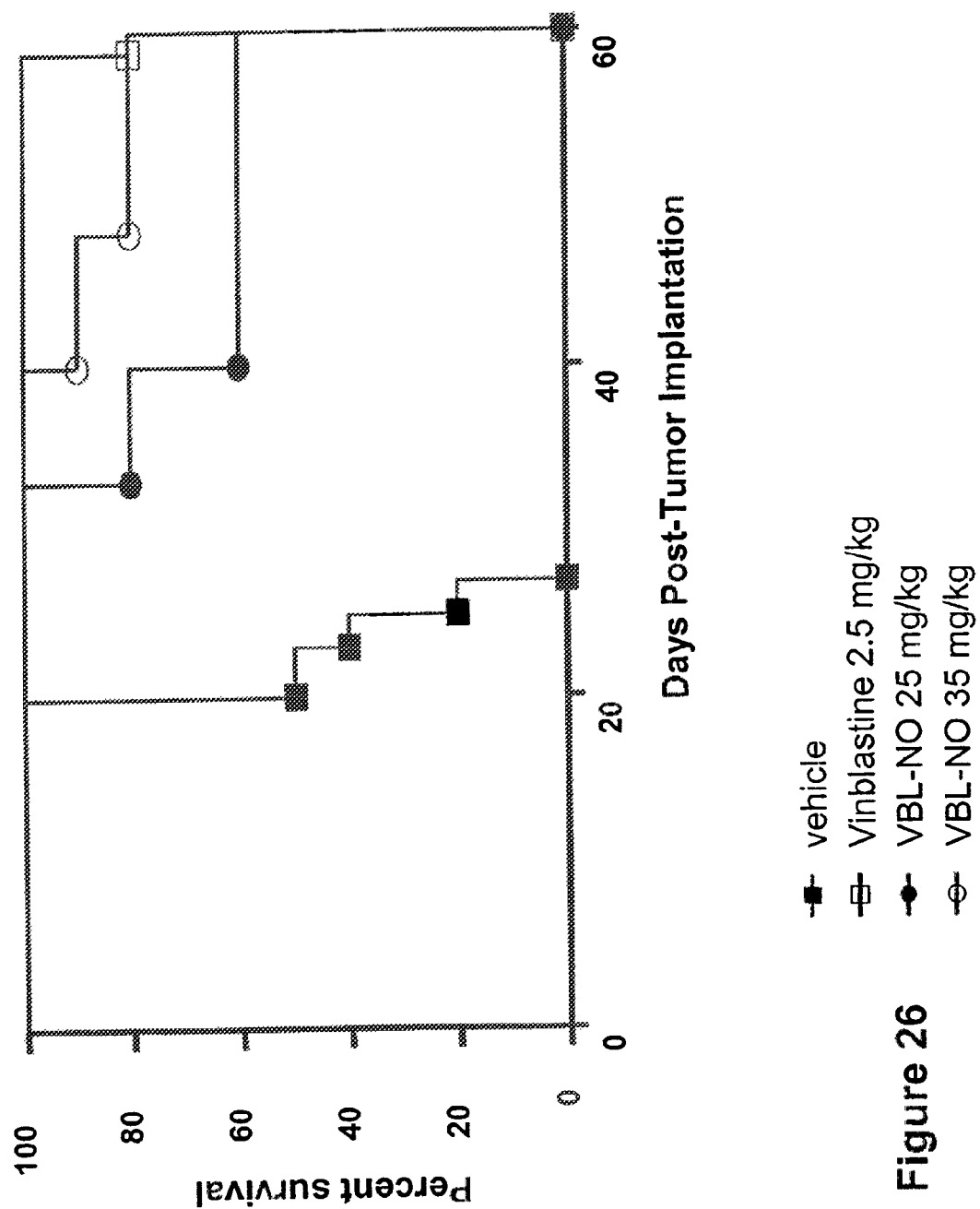

FIG. 26 shows efficacy of vinblastine N-oxide analog (VBL-NO) or vinblastine (VBL) in the HL60 promyelocytic leukemia xenograft model in nude mice (n=10) as determined by Kaplan Meier Survival analysis. All agents were i.v. administered on a q3d×5 schedule (d. 1, 4, 7, 10, 13) at the indicated dosages.
Median Survival (days):
Vehicle=21.5;
VBL-NO 25 mg/kg=60;
VBL-NO 35 mg/kg=60;
Vinblastine 2.5 mg/kg=60

Figure 27:
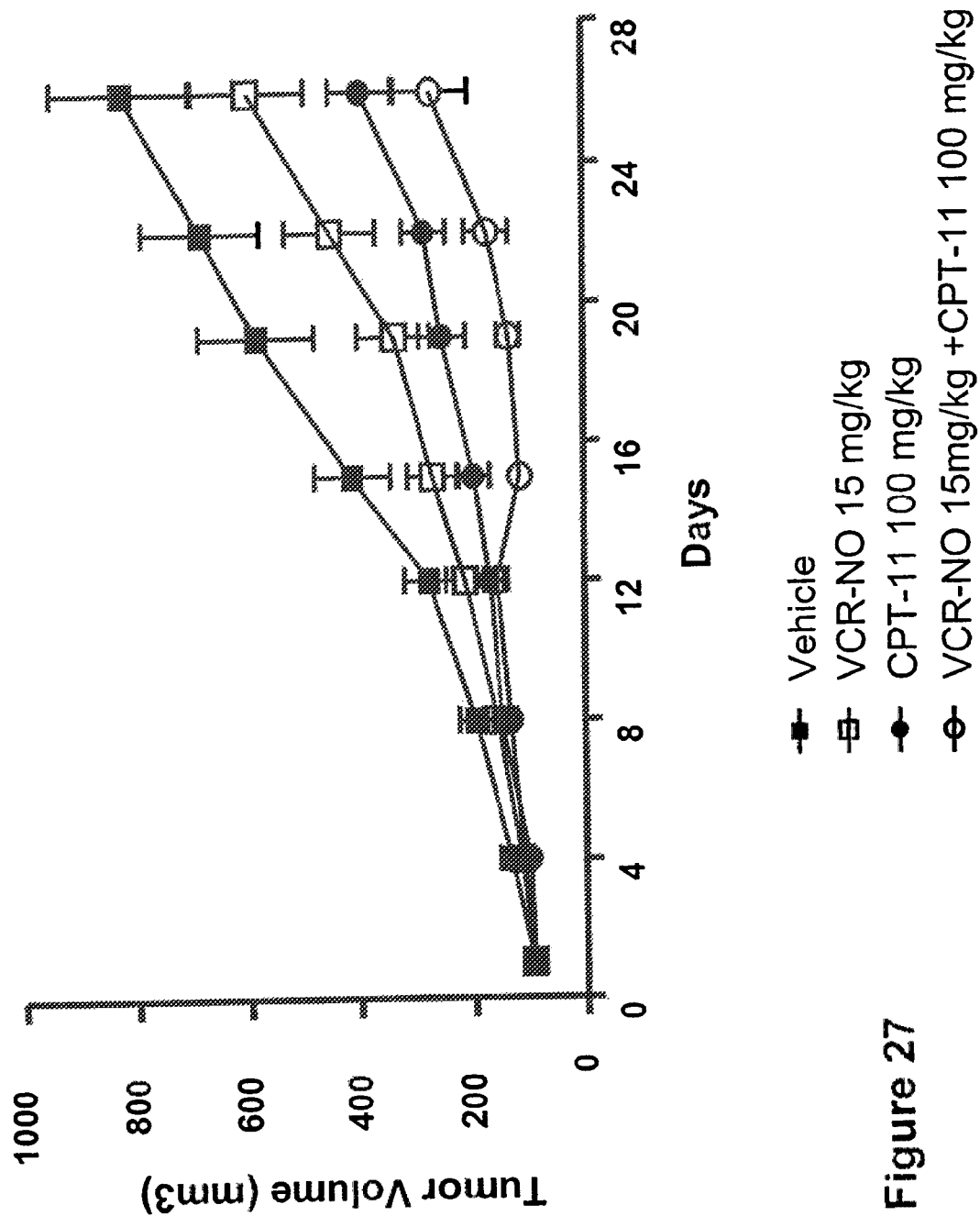

FIG. 27 shows efficacy of vincristine N-oxide analog (VCR-NO) as single agent or in combination with CPT-11 in the HT29 colon xenograft model in nude mice model (n=10) as determined by Tumor Growth Delay. VCR-NO was i.v. administered on a q3d×5 schedule (d. 1, 4, 7, 10, 13) at 15 mg/kg. CPT-11 was i.p. administered at 100 mg/kg on a q week×3 schedule.
Tumor Growth Delay:
VCR-NO 15 mg/kg=52%;
CPT-11 100 mg/kg=52%;
VCR-NO 25 mg/kg+CPT-11 100 mg/kg=111%

Figure 28:
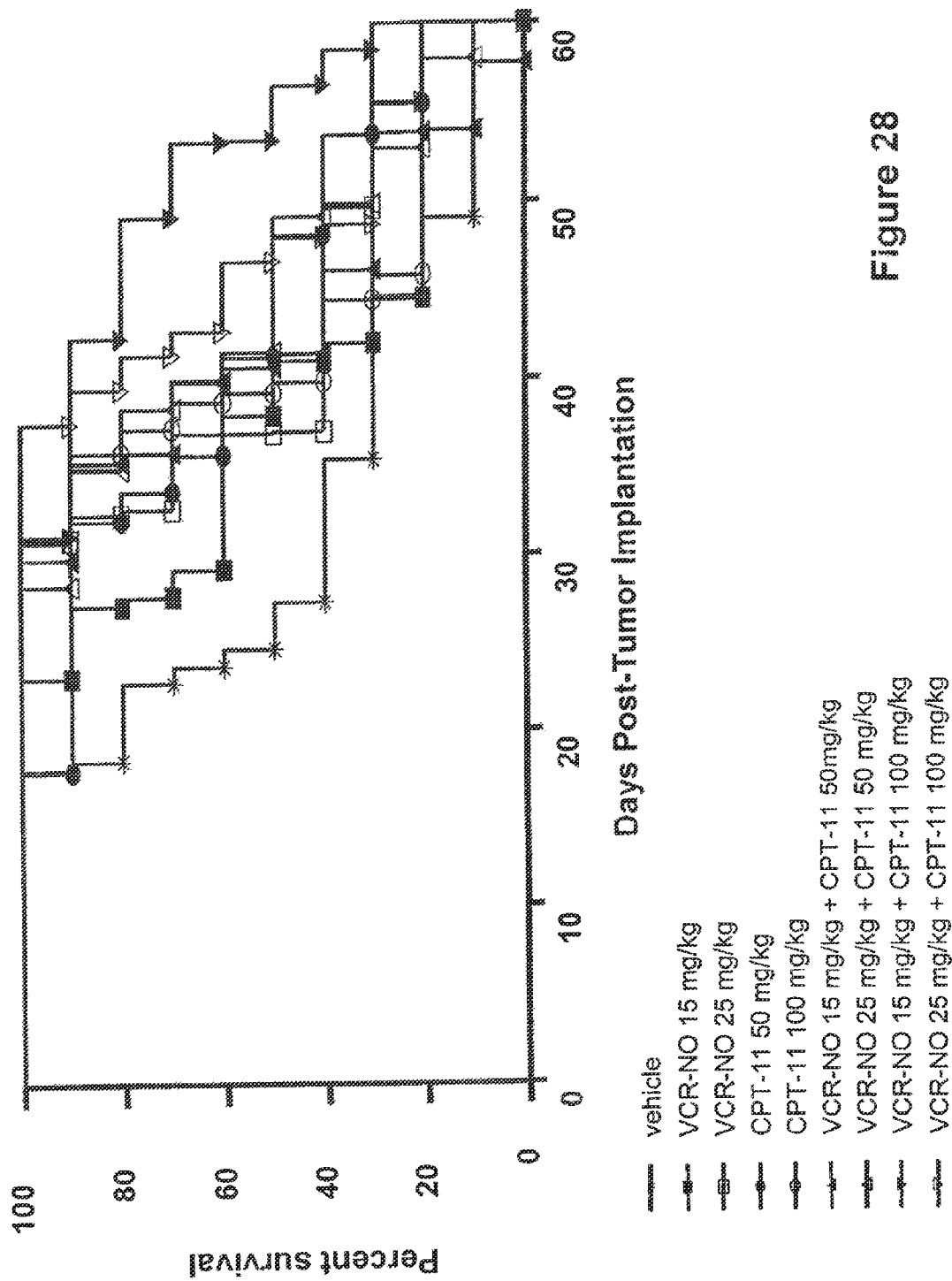

FIG. 28 shows efficacy of vincristine N-oxide analog (VCR-NO) as single agent or in combination with CPT-11 in the HT29 colon xenograft model in nude mice model (n=10) as determined by Kaplan Meier Survival analysis. VCR-NO was i.v. administered on a q3d×5 schedule (d. 1, 4, 7, 10, 13). CPT-11 was i.p. administered on a q week×3 schedule at the indicated dosages.
Median Survival (days):
Vehicle=26.0
VCR-NO 15 mg/kg=39.6
VCR-NO 25 mg/kg=37.1
CPT-11 50 mg/kg=44.7
CPT-11 100 mg/kg=39.6
VCR-NO 15 mg/kg+CPT-11 50 mg/kg=41.5
VCR-NO 25 mg/kg+CPT-11 50 mg/kg=45.4
VCR-NO 15 mg/kg+CPT-11 100 mg/kg=55.0
VCR-NO 25 mg/kg+CPT-11 100 mg/kg=47.4

Figure 29:
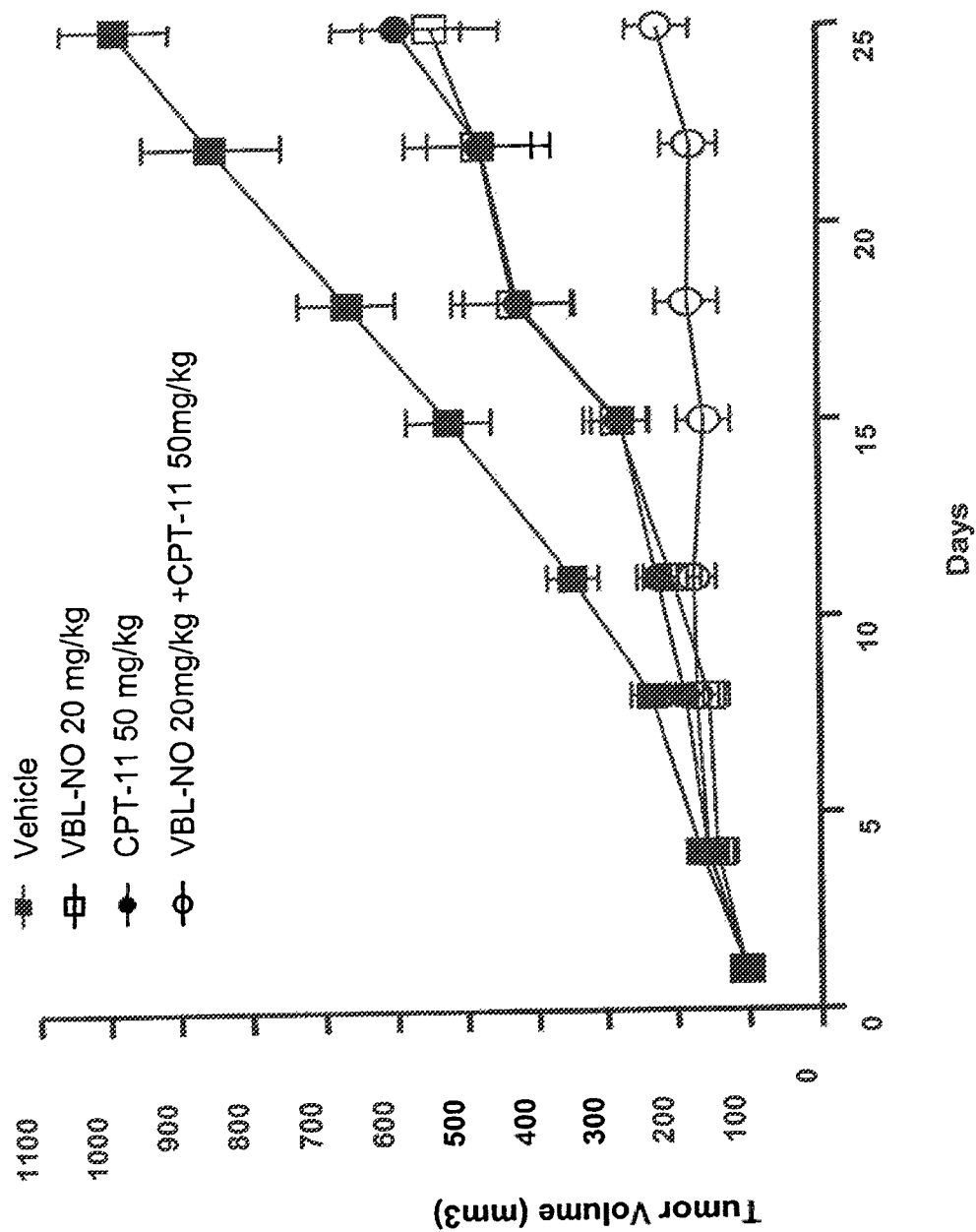

FIG. 29 shows efficacy of vinblastine N-oxide analog (VBL-NO) as single agent or in combination with CPT-11 in the HT29 colon xenograft model in nude mice model (n=10) as determined by Tumor Growth Delay. VBL-NO was i.v. administered on a q3d×5 schedule (d. 1, 4, 7, 10, 13) at 20 mg/kg. CPT-11 was i.p. administered at 50 mg/kg on a q week×3 schedule.

Tumor Growth Delay:
VBL-NO 20 mg/kg=46%
CPT-11 50 mg/kg=34%
VBL-NO 20 mg/kg+CPT-11 50 mg/kg=83%

Figure 30:
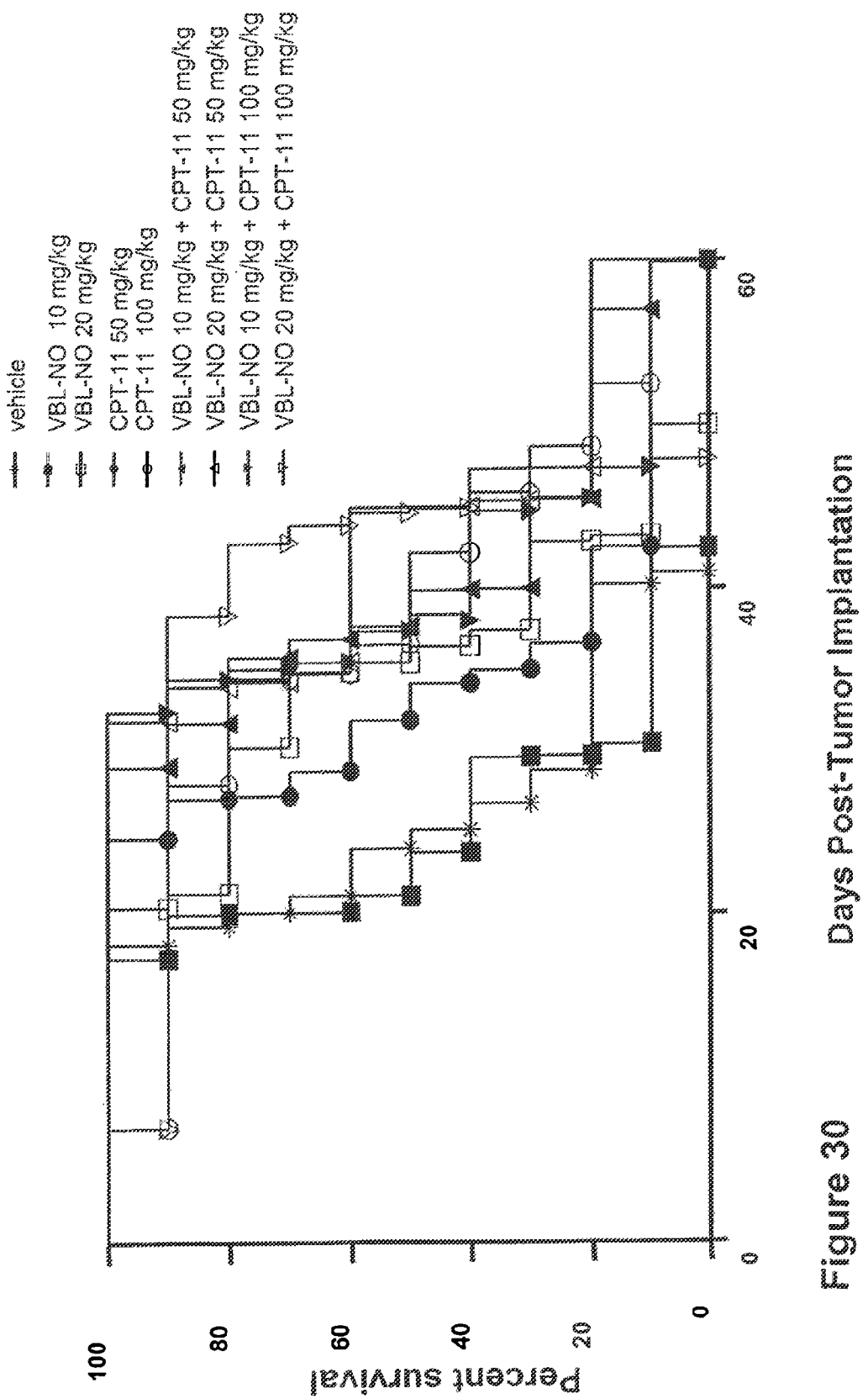

FIG. 30 shows efficacy of vinblastine N-oxide analog (VBL-NO) as single agent or in combination with CPT-11 in the HT29 colon xenograft model in nude mice model (n=10) as determined by Kaplan Meier Survival analysis. VBL-NO was i.v. administered on a q3dx5 schedule (d. 1, 4, 7, 10, 13). CPT-11 was i.p. administered on a q weekx3 schedule at the indicated dosages.

Median Survival (days):
Vehicle=24.7
VBL-NO 10 mg/kg=22.5
VBL-NO 20 mg/kg=36.1
CPT-11 50 mg/kg=33.1
CPT-11 100 mg/kg=39.5
VBL-NO 10 mg/kg+CPT-11 50 mg/kg=38.9
VBL-NO 20 mg/kg+CPT-11 50 mg/kg=45.1
VBL-NO 10 mg/kg+CPT-11 100 mg/kg=38.0
VBL-NO 20 mg/kg+CPT-11 100 mg/kg=44.8

DETAILED DESCRIPTION OF THE INVENTION

One aspect of the invention is drawn to vinca alkaloid N-oxides having Formula I:

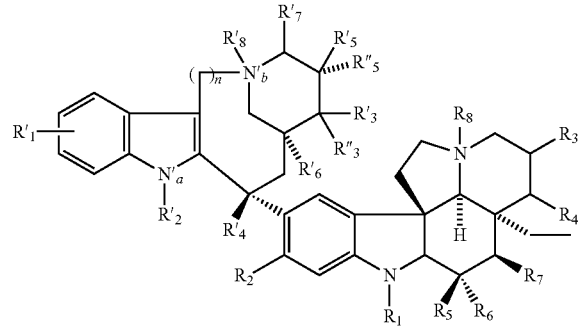

I wherein $R_1$-$R_8$, $R'_1$-$R'_8$, $R''_3$, $R''_5$, and n are as defined above, or a pharmaceutically acceptable salt thereof.

According to another aspect of the invention, a therapeutically effective amount of a compound having Formula I, or a pharmaceutically acceptable salt thereof, and at least one other active agent is provided in the form of a pharmaceutical composition having at least one pharmaceutically acceptable carrier. In certain instances, the at least one other active agent is a chemotherapeutic agent (including an active vitamin D compound). Compounds having Formula I may be formulated in a single formulation with the other active agent(s), or formulated independently.

According to one aspect of the invention, methods for treating, ameliorating, or preventing hyperproliferative disorders are provided, wherein a therapeutically effective amount of a compound having Formula I, or a pharmaceutically acceptable salt thereof, is administered to an animal in need thereof. In certain aspects of the invention, the hyperproliferative disorder is cancer.

A further aspect of the invention relates to methods for treating, ameliorating, or preventing a hyperproliferative disorder comprising administering a therapeutically effective amount of a compound having Formula I, or a pharmaceutically acceptable salt thereof, in combination with at least one other active agent or treatment to a patient in need thereof. In certain embodiments, combinations of a compound having Formula I with a chemotherapeutic agent are administered. In one embodiment, the chemotherapeutic agent is selected from gemcitabine and irinotecan.

Hyperproliferative disorders which can be treated with the compounds having Formula I include any hypoxia-aggravated hyperproliferative disease and/or disorder, such as any number of cancers. Generally, such cancers include, without limitation, cancers of the bladder, brain, breast, cervix, colon, endometrium, esophagus, head and neck, kidney, larynx, liver, lung, oral cavity, ovaries, pancreas, prostate, skin, stomach, and testis. Certain of these cancers may be more specifically referred to as acute and chronic lymphocytic leukemia, acute granulocytic leukemia, adrenal cortex carcinoma, bladder carcinoma, breast carcinoma, cervical, carcinoma, cervical hyperplasia, choriocarcinoma, chronic granulocytic leukemia, chronic lymphocytic leukemia, colon carcinoma, endometrial carcinoma, esophageal carcinoma, essential thrombocytosis, genitourinary carcinoma, hairy cell leukemia, head and neck carcinoma, Hodgkin's disease, Kaposi's sarcoma, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid and lymphocytic leukemia, neuroblastoma, non-Hodgkin's lymphoma, osteogenic sarcoma, ovarian carcinoma, pancreatic carcinoma, polycythemia vera, primary brain carcinoma, primary macroglobulinemia, prostatic carcinoma, renal cell carcinoma, rhabdomyosarcoma, skin cancer, small-cell lung carcinoma, soft-tissue sarcoma, squamous cell carcinoma, stomach carcinoma, testicular carcinoma, thyroid carcinoma, and Wilms' tumor. In one embodiment, the cancer is a solid tumor. In another embodiment, the cancer is selected from the group consisting of colon cancer, brain cancer, glioma, multiple myeloma, head and neck cancer hepatocellular cancer, melanoma, ovarian cancer, cervical cancer, renal cancer, and non-small cell lung cancer.

Animals which may be treated according to the present invention include all animals which may benefit from administration of compounds having Formula I. Such animals include humans, pets such as dogs and cats, and veterinary animals such as cows, pigs, sheep, goats and the like.

The term "alkyl" as used herein refers to an unsaturated acyclic hydrocarbon radical. The term "lower alkyl" refers to acyclic hydrocarbon radicals containing from about 2 to about 10 carbon atoms, preferably from about 2 to about 8 carbon atoms and more preferably 1 to about 6 carbon atoms. Examples of suitable alkyl radicals include methyl, ethyl, propyl, butyl, isobutyl, pentyl, 2-methylbutyl, 3-methylbutyl, hexyl, heptyl, and octyl, and the like.

The term "alkoxy" means a straight, branched or cyclic hydrocarbon configuration and combinations thereof, including from 1 to 20 carbon atoms, preferably from 1 to 8 carbon atoms, more preferably from 1 to about 4 carbon atoms, and an oxygen atom at the point of attachment. Suitable alkoxy groups include methoxy, ethoxy, n-propoxy, isopropoxy, n-butoxy, iso-butoxy, sec-butoxy, tert-butoxy, cyclopropyloxy, cyclohexyloxy, and the like. "Lower alkoxy" refers to alkoxy groups having from 1 to 4 carbon atoms.

The term "acyl" or "alkanoyl means an alkyl group attached to a carbonyl group.

The term "halogenoacyl" means an acyl group substituted with one or more halogen groups (e.g. F, Cl, Br and I groups), including trifluoroacetyl, pentafluoropropionyl and the like.

The term "non-N-oxide" as used herein refers to an amine compound that is not oxidized at the nitrogen atom. As an example, vinblastine is the non-N-oxide form of vinblastine N-oxide.

The term "pharmaceutical composition" as used herein, is to be understood as defining compositions of which the individual components or ingredients are themselves pharmaceutically acceptable, e.g., where oral administration is foreseen, acceptable for oral use; where topical administration is foreseen, topically acceptable; and where intravenous administration is foreseen, intravenously acceptable.

As used herein, the term "therapeutically effective amount" refers to that amount of the therapeutic agent sufficient to result in amelioration of one or more symptoms of a disorder, or prevent advancement of a disorder, or cause regression of the disorder. For example, with respect to the treatment of cancer, a therapeutically effective amount preferably refers to the amount of a therapeutic agent that decreases the rate of tumor growth, decreases tumor mass, decreases the number of metastases, increases time to tumor progression, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

Compounds having Formula I can be provided as pharmaceutically acceptable salts. Examples of pharmaceutically acceptable salts (i.e., addition salts) include inorganic and organic acid addition salts such as hydrochloride, hydrobromide, phosphate, sulphate, citrate, lactate, tartrate, maleate, fumarate, mandelate, benzoate and oxalate; and inorganic and organic base addition salts with bases such as sodium hydroxy, Tris(hydroxymethyl)aminomethane (TRIS, tromethane) and N-methyl-glucamine. Although the salts typically have similar physiological properties compared to the free base, certain acid addition salts may demonstrate preferred physicochemical properties, e.g., enhanced solubility, improved stability. Certain salts exhibit less hygroscopicity. Some salts may be more easily crystallized than others. Other salts form free flowing powders. For example, in one embodiment, vinblastine N-oxide dihydrochloride forms a stable clear solution at about 20 mg/mL in de-ionized water and in 5% dextrose/water solutions. One particular pharmaceutically acceptable salt is derived from maleic acid, the salt being either a hydrogen maleate or a dimaleate salt. Another particular pharmaceutically acceptable salt is hydrochloride salts. In one embodiment, the salt is vinblastine N-oxide dihydrochloride. In another embodiment, the salt is vincristine N-oxide dihydrochloride.

Certain of the compounds of the present invention may exist as stereoisomers including optical isomers as well as the individual enantiomers that may be separated according to methods that are well known to those of ordinary skill in the art. Optical purity or enantiomeric excess (ee) may range from 0%-100%. The invention includes all stereoisomers and both the racemic mixtures of such stereoisomers as well as the individual enantiomers that may be separated according to methods that are well known to those of ordinary skill in the art. Certain of the compounds of the present invention may also exist as diasteroisomers wherein one or more substituents on the vinca alkaloid analog contain one or more chiral centers.

In certain embodiments, the N-oxide formation creates a new chiral center with the formation of individual enantiomers (e.g., in a stereoselective N-oxidation of an achiral vinca alkaloid or analog), mixture of enantiomers (e.g., in a non-stereoselective oxidation of an achiral vinca alkaloid or analog), individual diasteroisomers (e.g., in a stereoselective N-oxidation of an enantiomerically pure vinca alkaloid or analog), or mixtures of diasteroisomers (e.g., in a non-stereoselective N-oxidation of an enantiomeric mixture of a vinca alkaloid or analog). Thus, the invention includes all N-oxide mixtures of enantiomers and diasteroisomers as well as individual diasteroisomers and enantiomers that may be prepared using stereoselective reactions or separated according to methods that are well known to those of ordinary skill in the art.

In certain embodiments of the invention, compounds having Formula I are administered in combination with one or more other active agents (e.g., chemotherapeutic agents) or treatments. By way of non-limiting example, a patient may be treated for a hyperproliferative disorder, such as cancer, by the administration of a therapeutically effective amount of a compound having Formula I in combination with radiotherapy agent/treatment or the administration of a chemotherapeutic agent.

In other embodiments, compounds of the invention are administered in combination with agents, such as anti-angiogenic agents, that block inhibit or modulate tumor neovascularization. In preferred embodiments, anti-angiogenesis agents can be any anti-angiogenesis agent which is used, has been used, or is known to be useful for the treatment of hyperproliferative disorders. Examples of anti-angiogenesis agents include bevacizumab (Avastin™), VEGF-TRAP, anti-VEGF-receptor antibodies, angiostatin, endostatin, batimastat, captopril, cartilage derived inhibitor, genistein, interleukin 12, lavendustin, medroxypregesterone acetate, recombinant human platelet factor 4, tecogalan, thrombospondin, TNP-470, VEGF antagonists, anti-VEGF monoclonal antibody, soluble VEGF-receptor chimaeric protein, antisense oligonucleotides, antisense oligodexoynucleotides, siRNAs, anti-VEGF aptamers, pigment epithelium derived factor, a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, pentosan polysulfate, a cyclooxygenase inhibitor, carboxyamidotriazole, combretastatin A-4, squalamine, 6-O-chloroacetyl-carbonyl)-fumagillol, thalidomide, troponin-1, indolinethiones, pyridopyrimidines, quinazolines, phenyl-pyrrolo-pyrimidines, trastuzumab, calcium influx inhibitor (CAI), neomycin, squalamine, marimastat, prinomastat (AG-3340), metastat (COL-3) and cinnoline derivatives. Additional anti-angiogenic compounds that may be administered in combination with the compounds of the present invention are described in U.S. Pat. Nos. 5,192,744, 5,426,100, 5,733,876, 5,840,692, 5,854,205, 5,990,280, 5,994,292, 6,342,219, 6,342,221, 6,346,510, 6,479,512, 6,719,540, 6,797,488, 6,849,599, 6,869,952, 6,887,874, 6,958,340 and 6,979,682.

In certain embodiments, the compounds of the present invention are administered in combination with a vascular targeting agent (also known as vascular damaging agents). In one embodiment, the vascular targeting agent is for the treatment of malignant or non-malignant vascular proliferative disorders. In other embodiments, vascular targeting agents can be any vascular targeting agent which is used, has been used, or is known to be useful for the treatment of hyperproliferative disorders. Examples of vascular targeting agents that may be administered in combination with the compounds of the present invention include DMXAA 5,6-dimethylxanthenone-4-acetic acid, ZD6126, (5S)-5-(acetylamino)-9,10,11-trimethoxy-6,7-dihydro-5H-dibenzo[a,c]cyclohepten-3-yl dihydrogen phosphate, also known as N-acetylcolchinol-O-phosphate (see, for example, U.S. Pat. No. 6,906,048); functionalized stilbene derivatives such as combretastatin A4 and its prodrugs (see, e.g., U.S. Pat. Nos. 6,919,324 and 6,773,702); dioleoyltrimethyl-ammonium propane (DOTAP), N-[1-(2,3-dioleoyloxy)-propyl]-N,N,N-trimethylammonium chloride (DOTMA), dimethyldioctadecylammonium bromide (DDAB), 1,2-dimyristyloxypropyl-3-dimethylhydroxyethyl (DMRIE), dioleoyl-3-dimethylammonium propane (DODAP), N,N-dioleyl-N,N-dimethylammonium chloride (DODAC), or N-(1-(2,3-dioleyloxy)propyl)-N-(2-(sperminecarboxamido)ethyl)-N,N-dimethyl ammonium trifluoroacetate (DOSPA), or any other natural or synthetic cationic lipids, including, for example, dioleoylphosphatidyl-choline (DOPC), dipalmitoylphosphatidylcholine (DPPC), disteroylphosphatidylcholine (DSPC), dimyristoylphosphatidylcholine (DMPC), or 1,2-sn-dioleoylphosphatidylcholine (DOPE), or any other natural or synthetic electrostatically neutral lipids (see, for example, U.S. Pat. No. 6,680,068); vascular targeting agents which incorporate benzo[b]thiophene, indole, and benzofuran molecular skeletons such as those described in U.S. Pat. No. 6,593,374.

In other embodiments, the compounds of the present invention are administered in combination with a hypoxia-inducible factor 1 (HIF1) inhibitor. In one embodiment, the HIF1 inhibitor is for the treatment of malignant or non-malignant vascular proliferative disorders. In other embodiments, HIF1 inhibitors can be any HIF1 inhibitor which is used, has been used, or is known to be useful for the treatment of hyperproliferative disorders. Examples of HIF1 inhibitors suitable for use in combination with compounds of the present invention include topotecan, P13 kinase inhibitors; LY294002; rapamycin; histone deacetylase inhibitors such as [(E)-(1S,4S,10S,21R)-7-[(Z)-ethylidene]-4,21-diisopropyl-2-oxa-12,13-dithia-5,8,20,23-tetraazabicyclo-[8,7,6]-tricos-16-ene-3,6,9,19,22-pentanone (FR901228, depsipeptide); heat shock protein 90 (Hsp90) inhibitors such as geldanamycin, 17-allylamino-geldanamycin (17-AAG), and other geldanamycin analogs, and radicicol and radicicol derivatives such as KF58333; genistein; indanone; staurosporin; protein kinase-1 (MEK-1) inhibitors such as PD98059 (2'-amino-3'-methoxyflavone); PX-12 (1-methylpropyl 2-imidazolyl disulfide); pleurotin PX478; quinoxaline 1,4-dioxides; sodium butyrate (NaB); sodium nitropurruside (SNP) and other NO donors; microtubule inhibitors such as novobiocin, panzem (2-methoxyestradiol or 2-ME2), vincristines, taxanes, epothilones, discodermolide, and derivatives of any of the foregoing; coumarins; barbituric and thiobarbituric acid analogs; camptothecins; and YC-1. See U.S. Pat. No. 6,979,675.

In certain embodiments, the compounds of the present invention are administered in combination with an Hsp90 inhibitor. In one embodiment, the Hsp90 inhibitor is for the treatment of malignant or non-malignant vascular proliferative disorders. In other embodiments, Hsp90 inhibitors can be any Hsp90 inhibitor which is used, has been used, or is known to be useful for the treatment of hyperproliferative disorders. Examples of Hsp90 inhibitors that may be combined with the compounds of the present invention include geldanamycin, 17-allylamino-17-demethoxygeldanamycin, geldanamycin derivatives such as those described in U.S. Pat. No. 6,890,917, dexamethasone and benzoquinone ansamycins such as those described in U.S. Pat. No. 6,872,715. Additional Hsp90 inhibitors are disclosed in U.S. Pat. Nos. 6,613,780, 6,281,229 and 6,903,116.

In other embodiments, the compounds of the present invention are administered in combination with an inhibitor of tyrosine and/or serine/threonine kinases and tyrosine kinase receptors involved in cellular signaling. These include tyrosine kinase inhibitors of Src, Abl, Platelet Derived Growth Factor Receptors, Vascular Endothelial Growth Factor Receptors, c-Met, Fibroblast Growth Factor receptors, Epidermal Growth Factor Receptors, Insulin Growth Factor Receptors, mTOR, Flt-3, CSF-1 Receptor, AKT, Polo kinases, Aurora Kinases, STAT-3, P1-3 Kinase, Ras, Raf and Mitogen Activated Kinases, MEK, ERK. Examples of tyrosine kinase and serine/threonine kinase inhibitors include (but not limited to): AMG706, ZA6474, BAY 43-9006, Dasatinib, CEP-701, XL647, XL999, Lapatinb, MLN518/CT53518, PKC412, ST1571, AMN107, AEE 788, OSI-930, OSI-817, SU11248, AG-03736, GW-786034m, CEP-7055.

In other embodiments, the compounds of the present invention are administered in combination with HDAC inhibitors. Examples include (but not limited to) SAHA, MS-275, MGCD0103, LBH589, PXD101, FK228.

In other embodiments, the compounds of the present invention are administered in combination with proteasome inhibitors such as Velcade.

In other embodiments, the compounds of the present invention are administered in combination with pro-apoptotic agents such as TRAIL, anti-DR4/DR5 (TRA8) antibodies, IAP, Survivin or small molecules that stimulate caspase activation.

In other embodiments, the compounds of the present invention are administered in combination with inhibitors of cell cycle regulators such as CDK inhibitors.

"In combination" refers to the use of more than one treatment. The use of the term "in combination" does not restrict the order in which treatments are administered to a subject being treated for a hyperproliferative disorder. A first treatment can be administered prior to, concurrently with, after, or within any cycling regimen involving the administration of a second treatment to a subject with a hyperproliferative disorder. For example, the first treatment can be administered 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before a treatment; or the first treatment can be administered 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after a second treatment. Such treatments include, for example, the administration of compounds having Formula I in combination with one or more chemotherapeutic agents or radiotherapeutic agents/treatments.

The term "chemotherapeutic agent," as used herein, is intended to refer to any chemotherapeutic agent known to those of skill in the art to be effective for the treatment, prevention or amelioration of hyperproliferative disorders such as cancer. Chemotherapeutic agents include, but are not limited to, small molecules, synthetic drugs, peptides, polypeptides, proteins, nucleic acids (e.g., DNA and RNA polynucleotides including, but not limited to, antisense nucleotide sequences, triple helices and nucleotide sequences encoding biologically active proteins, polypeptides or peptides), antibodies, synthetic or natural inorganic molecules, mimetic agents, and synthetic or natural organic molecules. Any agent which is known to be useful, or which has been used or is currently being used for the treatment or amelioration of a hyperproliferative disorder can be used in combination with a compound having Formula I. See, e.g., Hardman et al., eds., 2002, Goodman & Gilman's The Pharmacological Basis Of Therapeutics 10th Ed, Mc-Graw-Hill, New York, N.Y. for information regarding therapeutic agents which have been or are currently being used for the treatment or amelioration of a hyperproliferative disorder.

Particular chemotherapeutic agents useful in the methods and compositions of the invention include alkylating agents, antimetabolites, anti-mitotic agents, epipodophyllotoxins, antibiotics, hormones and hormone antagonists, enzymes, platinum coordination complexes, anthracenediones, substituted ureas, methylhydrazine derivatives, imidazotetrazine derivatives, cytoprotective agents, DNA topoisomerase inhibitors, biological response modifiers, retinoids, therapeutic antibodies, differentiating agents, immunomodulatory agents, angiogenesis inhibitors and anti-angiogenic agents.

Certain chemotherapeutic agents include, but are not limited to, abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, Elliott's B solution, epirubicin, epoetin alfa, estramustine, etoposide, exemestane, filgrastim, floxuridine, fludarabine, fluorouracil, fulvestrant, gemcitabine, gemtuzumab ozogamicin, gefitinib, goserelin, hydroxyurea, ibritumomab tiuxetan, idarubicin, ifosfamide, imatinib, interferon alfa-2a, interferon alfa-2b, irinotecan, letrozole, leucovorin, levamisole, lomustine, meclorethamine, megestrol, melphalan, mercaptopurine, mesna, methotrexate, methoxsalen, methylprednisolone, mitomycin C, mitotane, mitoxantrone, nandrolone, nofetumomab, oblimersen, oprelvekin, oxaliplatin, paclitaxel, pamidronate, pegademase, pegaspargase, pegfilgrastim, pemetrexed, pentostatin, pipobroman, plicamycin, polifeprosan, porfimer, procarbazine, quinacrine, rasburicase, rituximab, sargramostim, streptozocin, talc, tamoxifen, tarceva, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate. In certain embodiments, chemotherapeutic agents are selected from gemcitabine and irinotecan.

Chemotherapeutic agents may be administered at doses that are recognized by those of skill in the art to be effective for the treatment of the hyperproliferative disorder. In certain embodiments, chemotherapeutic agents may be administered at doses lower than those used in the art due to the additive or synergistic effect of the compounds having Formula I.

Accordingly, the present invention relates to a method for preventing or ameliorating side effects induced by or associated with chemotherapy by using lower effective doses of the chemotherapeutic agents than would otherwise be possible without the use of the compounds of Formula I. In particular, the method relates to amelioration, prevention of side effects induced by or associated with the chemotherapy of a variety of cancers including, but not limited to, brain cancer, breast cancer, gastrointestinal cancers comprising colon, colorectal, esophageal, gastric, hepatocellular, pancreatic and rectal cancers, genitourinary cancers comprising bladder, prostate, renal cell and testicular cancers, gynecologic cancers comprising cervical, endometrial, ovarian and uterine cancers, head and neck cancer, leukemias comprising acute lymphoblastic, acute myelogenous, acute promyelocytic, chronic lymphocytic, chronic myelogenous, and hairy cell leukemias, non-small-cell and small-cell lung cancers, Hodgkin's and non-Hodgkin's lymphomas, melanoma, multiple myeloma and sarcoma.

Therapeutic agents useful in the methods and compositions of the invention include active vitamin D compound or mimics thereof, antineoplastic agents (e.g., actinomycin D, vincristine, vinorelbine, topoisomerase 1 inhibitors (camptothecin and analogs such as irinotecan, SN-38, topotecan, 9-aminocamptothecin, 10-aminocamptothecin, 10,11-methylenedioxycamptothecin), azacitidine (5-azacytidine, 5AzaC), thalidomide vinblastine, methotrexate, azathioprine, fluorouracil, doxorubicin, mitomycin, taxanes (docetaxel, paclitaxel)), angiogenic inhibitors (e.g., VEGF-TRAP, angiostatin, endostatin, aptamer antogonist of VEGF, batimastat, captopril, cartilage derived inhibitor, genistein, interleukin 12, lavendustin, medroxypregesterone acetate, recombinant human platelet factor 4, tecogalan, thrombospondin and TNP-470), serine/threonine kinase inhibitors, tyrosine kinase inhibitors, HDAC inhibitors, Proteasome inhibitors, CDK inhibitors, HSP inhibitors, vasodilators (e.g., nitrates, calcium channel blockers), anticoagulants (e.g., heparin), anti-platelet agents (e.g., aspirin, blockers of IIb/IIIa receptors, clopidogrel), anti-thrombins (e.g., hirudin, iloprost), immunosuppressants (e.g., sirolimus, tranilast, dexamethasone, tacrolimus, everolimus, A24), collagen synthetase inhibitors (e.g., halofuginone, propyl hydroxylase, C-proteinase inhibitor, metalloproteinase inhibitor), anti-inflammatories (e.g., corticosteroids, non-steroidal anti-inflammatory drugs), 17β-estradiol, angiotensin converting enzyme inhibitors, colchicine, fibroblast growth factor antagonists, histamine antagonists, lovastatin, nitroprusside, phosphodiesterase inhibitors, prostaglandin inhibitors, suramin, serotonin blockers, thioprotease inhibitors, platelet-derived growth factor antagonists, nitric oxide, and angiopeptin. In one embodiment, the therapeutic agent is a taxane, e.g., paclitaxel or docetaxel.

Administration of some topoisomerase 1 inhibitors to patients in need of such treatment is known to cause serious adverse events. For example, various serious adverse events are known to be associated with the administration of CAMPTOSAR® to patients, including early and late stage diarrhea. See CAMPTOSAR® Product Label, Pfizer, Inc.

In three open-label studies, CAMPTOSAR® was administered in repeated 6-week cycles consisting of a 90-minute intravenous infusion once weekly for 4 weeks, followed by a 2-week rest period. Starting doses of CAMPTOSAR® for these trials were 100, 125, or 150 mg/m$^2$ but the 150 mg/m$^2$ dose was poorly tolerated due to unacceptably high rates of grade 4 late diarrhea and febrile neutropenia.

In a multicenter study that enrolled 166 patients from 30 institutions evaluating CAMPTOSAR® as second-line treatment for recurrent or progressive metastatic colorectal cancer (referred to as Study 3 in the CAMPTOSAR® product label), the initial dose was 125 mg/m$^2$ but was reduced to 100 mg/m$^2$ because the toxicity seen in the 125 mg/m$^2$ dose was perceived to be greater than those seen in previous studies.

Data from an open-label, single-agent, single arm, multicenter, clinical study involving a total of 132 patients is cited as supporting a once every-3-week dosage schedule of irinotecan in the treatment of patients with metastatic cancer of the colon or rectum that recurred or progressed following treatment with 5-FU. Patients received a starting dose of 350 mg/m² given by 30-minute intravenous infusion once every 3 weeks. Among the 132 previously treated patients in this trial, the intent-to-treat response rate was 12.1% (95% CI, 7.0% to 18.1%).

According to the product label, injection of CAMPTOSAR can induce both early and late forms of diarrhea that appear to be mediated by different mechanisms. Early diarrhea (occurring during or shortly after infusion of CAMPTOSAR) is cholinergic in nature. It is usually transient and only infrequently is severe. It may be accompanied by symptoms of rhinitis, increased salivation, miosis, lacrimation, diaphoresis, flushing, and intestinal hyperperistalsis that can cause abdominal cramping. Late diarrhea (generally occurring more than 24 hours after administration of CAMPTOSAR) can be prolonged, may lead to dehydration and electrolyte imbalance, and can be life threatening. Patients with severe diarrhea should be carefully monitored and given fluid and electrolyte replacement if they become dehydrated. National Cancer Institute (NCI) grade 3 diarrhea is defined as an increase of 7 to 9 stools daily, or incontinence, or severe cramping and NCI grade 4 diarrhea is defined as an increase of bloody stool, or need for parenteral support. If grade 3 or 4 late diarrhea occurs, administration of CAMPTOSAR should be delayed until the patient recovers and subsequent doses should be decreased. Myelosuppression. Deaths due to sepsis following severe myelosuppression have been reported in patients treated with CAMPTOSAR. The CAMPTOSAR product label recommends temporarily omission of the therapy if neutropenic fever occurs or if the absolute neutrophil count drops below 1,000/mm³. The label further instructs that even after the patient recovers to an absolute neutrophil count >1,500/mm³, subsequent doses of CAMPTOSAR should be reduced depending upon the level of myelosuppression observed.

Since lower doses of drugs generally pose lower risks of these side effects, it would be advantageous if lower doses of irinotecan can be administered without compromising its efficacy. One possible solution is to administer irinotecan in combination with a vinca alkaloid N-oxide. In certain embodiments of the present invention, a vinca alkaloid N-oxide (e.g., vincristine N-oxide) is administered to a subject in combination with topoisomerase 1 inhibitor (e.g., a camptothecin analog such as irinotecan) such that a synergistic anti-hyperproliferative effect is produced. A "synergistic anti-hyperproliferative effect" refers to a greater-than-additive anti-hyperproliferative effect which is produced by a combination of two drugs, and which exceeds that which would otherwise result from individual administration of either drug alone. Administration of certain doses of a vinca alkaloid N-oxide in combination with certain doses of a topoisomerase 1 inhibitor (e.g., irinotecan) unexpectedly resulted in an enhanced anti-hyperproliferative effect by providing greater efficacy than would otherwise result from use of either of the two agents alone. For example, in vivo administration of certain doses of vincristine N-oxide or vinblastine N-oxide with certain doses irinotecan produced enhanced anti-hyperproliferative effect beyond that which would be expected from the individual components (as measured by, for example, increased tumor growth delay). Moreover, in vivo administration of certain doses of irinotecan in combination with a vinca alkaloid N-oxide produced antihypreproliferative effect greater than that produced by twice the dose of irinotecan alone. Therefore, lower doses of one or both of the two agents may be used in treating hyperproliferative disorders, resulting in increased therapeutic efficacy, and/or decreased side-effects such as grade 4 late diarrhea and febrile neutropenia.

Other chemotherapeutic agents are also known to cause some unwanted side effects. Some of these side effects may be mild and treatable (such as dizziness, nausea, and some vomiting and/or diarrhea) while others are severe, life-threatening or even lethal. Among the more serious side effects are pulmonary toxicities that may lead to grades III-IV pneumonia, acute respiratory distress syndrome, or pulmonary fibrosis. Several cytotoxic drugs, including taxanes, bleomycin, methotrexate, busulfan, and the nitrosoureas may cause interstitial pneumonitis, alveolitis and pulmonary fibrosis. Administration of multiple cytotoxic drugs and pre-existing lung disease may potentiate pulmonary toxicity. Gucalap, R. and Dutcher, J. "Oncologic emergencies," in Harrison's Principles of internal medicine, Vol. 1, Fauci, A. S. et al., eds., 14$^{th}$ ed., McGraw-Hill, New York, N.Y., pp. 627-634 (1998).

Acute or subacute pneumonia generally affects the cells that line the alveoli, which are small sacs in the lungs that are responsible for exchanging oxygen from the air with carbon dioxide in the blood. Inflammation of these sensitive structures makes gas (oxygen and carbon dioxide) exchange less efficient, reducing the amount of oxygen that is absorbed from the air and delivered to the body. Various drugs used for the chemotherapy of cancer can damage lung tissues resulting in pneumonia. For example, 15% of patients suffering from head and neck cancer and treated with paclitaxel, a taxane similar to docetaxel (175 mg/m² over 3 hours on day 1), ifosfamide (1000 mg/m² over 2 hours on days 1-3), cisplatin (60 mg/m² IV day 1, repeated every 3-4 weeks), and mesna (600 mg/m² on days 1-3 in two divided doses, 400 mg/m² IV before ifosfamide and 200 mg/m² IV 4 hours after ifosfamide) required hospitalization due to pneumonia. Shin, D. M. et al., J. Clin. Oncol. 16: 1325-30 (1998). Also, 7% of acute myelogenous patients treated with gemtuzumab (9 mg/m² IV over 2 hours, two doses with 14 days between the doses) suffered from grade III or IV pneumonia. Product package insert for Mylotarg™, Wyeth-Ayerst Pharmaceuticals, Inc. Moreover, 7% of patients with myeloid blast crisis treated with once a day oral dose of either 400 mg or 600 mg imatinib mesylate (Gleevec®) developed grade III or IV pneumonia. Product package insert for Gleevac®, Novartis Pharmaceutical Corporation. In two single-arm open-label studies of fludarabine phosphate (Fludara®) in patients with refractory chronic lymphocytic leukemia, 16% of patients receiving 22-40 mg/m² daily Fludara® injections for five days every 28 days and 22% of patients receiving 15-25 mg/m² daily Fludara® injection for five days every 28 days developed pneumonia. Product insert for Fludara®, Berlex Laboratories, Richmond, Calif. Also, one of 44 cervical cancer patients treated with paclitaxel (135 mg/m² IV over 24 hours day 1), followed by cisplatin (75 mg/m² IV day 2, repeat every 21 days) developed grade III or IV pneumonia. Rose, P. G. et al., J. Clin. Oncol., 17: 2678-80 (1999). Other cancer drugs that have been implicated to cause pneumonia with grade III or IV toxicity include alemtuzmab (Campath®). Indeed, the product package insert of Campath® indicates that prophylaxis directed against *Pneumocystis carinii* pneumonia used in connection with Campath® treatment decreases, but does not eliminate, the occurrence of this infection.

Another example of pulmonary toxicity induced by or associated with chemotherapy is pulmonary fibrosis. Pulmonary fibrosis is the development of fibrous scar tissue in the lungs. Lung tissue is normally very elastic and expands as one breathes in order to provide a larger space for air. As scar tissue builds up in the lung, in some cases as a result of acute inflammation, the air sacs of the lungs become gradually replaced by fibrotic tissue. When the scar forms, the tissue becomes thicker causing an irreversible loss of the tissue's ability to transfer oxygen into the bloodstream. Various drugs used for the chemotherapy of cancer cause pulmonary fibrosis. Bleomycin (BLM) is known to induce pulmonary complications. Indeed, 7 of 148 testicular cancer patients treated with bleomycin (30 units IV, weekly), etoposide (100 mg/m$^2$/d IV days 1-5) and cisplatin (20 mg/m$^2$/d IV days 1-5), repeat cycle every 3 weeks for four 3-week periods, experienced grade III-IV respiratory toxicity with 3 patient deaths due to pulmonary toxicity. Nichols, J. R., et al. *J. Clin. Oncol.* 16: 1287-93 (1998).

Acute Respiratory Distress Syndrome ("ARDS") is a life-threatening condition in which inflammation of the lungs and accumulation of fluid in the air sacs (alveoli) leads to low blood oxygen levels. ARDS can be caused by any major lung inflammation or injury. Some common causes include pneumonia, septic shock, trauma, aspiration of vomit, chemical inhalation and chemotherapy. When a patient is suffering from ARDS, blood concentration of oxygen can remain dangerously low in spite of supplemental oxygen delivered by a mechanical ventilator through an endotracheal tube and many will succumb to ARDS. Typically patients require care in an intensive care unit. Symptoms usually develop within 24 to 48 hours of the original injury or illness.

Various drugs used for the chemotherapy of cancer damage the lung resulting in severe respiratory toxicities that can lead to ARDS. For example, 6 of 151 testicular cancer patients treated with cisplatin (20 mg/m$^2$/d IV, days 1-5), etoposide (75 mg/m$^2$/d IV, days 1-5), ifosfamide (1.2 g/m$^2$, days 1-5) and mesna (120 mg/m$^2$ IV before ifosfamide on day 1, followed by 1.2 g/m$^2$ on days 1-5), repeat cycle every 3 weeks for four 3-week periods, developed grade III-IV respiratory toxicity. Nichols, J. R., et al., *J. Clin. Oncol.* 16: 1287-93 (1998). Also, 2 out of 40 patients with bladder cancer treated with gemcitabine 1200 mg/m$^2$ IV (administered weekly times three on a 4-week cycle) experienced grade III-IV respiratory toxicity. Stadler, W. M., et al., *J. Clin. Oncol.* 15: 3394-98 (1997). Moreover, 18% of Non-Hodgkin's lymphoma patients treated with cyclophosphamide (600, 750 or 1000 mg/m$^2$ W day 1) and fludarabine (20 mg/m$^2$/d IV over 30 minutes, days 1-5), repeat cycle for 3 or 4 weeks, developed grade III or IV pulmonary toxicity including a case of documented *pneumocystis carinii* pneumonia, leading to discontinuation of treatment for 11% of patients (3 of 27 patients) because of pulmonary toxicity. Hochster, H. S. et al., *J. Clin. Oncol.* 18(5): 897-94 (2000). In addition, 7% of patients with newly diagnosed advanced Hodgkin's disease and treated with doxorubicin (25 mg/m$^2$ IV days 1, 15), bleomycin (10 mg/m$^2$ IV days 1, 15), vinblastine (6 mg/m$^2$ IV days 1, 15) and dacarbazine (375 mg/m$^2$ IV days 1, 15) developed grade III or IV pulmonary toxicity with a mortality rate of 3% due to pulmonary toxicity. Canellos, G. P. et al., *N. Engl. J. Med.* 327(21): 1478-84 (1992). Twenty percent of acute promyelocytic leukemia patients treated with all-trans-retinoic acid developed severe (7%), life-threatening (11%) or lethal (2%) grade III or IV pulmonary toxicity. Tallman, M. S. et al., *N. Eng. J. Med.,* 337(15): 1021-8 (1997).

Moreover, neutropenia is often associated with cancer chemotherapy. See, for example, Canellos, G. P. et al., *N. Engl. J. Med.* 327(21): 1478-84 (1992); Stadler, W. M., et al., *J. Clin. Oncol.* 15: 3394-98 (1997); Rose, P. G. et al., *J. Clin. Oncol.,* 17: 2678-80 (1999). Neutropenia is an abnormally low level of neutrophils in the blood and a large body of clinical data indicates that susceptibility to infectious diseases increase sharply when neurophil levels fall below 1000 cells/µL. Holland, S. M. and Gallin, J. I. "Disorders of Granulocytes and Monocytes," in Harrison's Principles of internal medicine, Vol. 1, Fauci, A. S. et al., eds., 14$^{th}$ ed., McGraw-Hill, New York, N.Y., pp. 351-359 (1998). Moreover, control of endogenous microbial flora becomes impaired when the absolute neutrophil count falls below 500 cell/µL.

Table 1 lists additional toxicity data reported in the scientific literature for various chemotherapeutic agents used to treat various cancers.

| Drug Dose and Target | Leukopenia/ Neutropenia Toxicity | Other Grade III-IV Toxicities |
|---|---|---|
| BRAIN CANCER | | |
| BCNU (carmustine) | Leukopenia | Thrombocytopenia 21% |
| 200 mg/m$^2$ IV daily | Grade III 4% | Nausea/Vomiting 5% |
| Repeat cycle every 6-8 weeks | Grade IV 1% | |
| Procarbazine 60 mg/m$^2$/d PO days 8-21 | Leukopenia | Thrombocytopenia 26% |
| Lomustine 110 mg/m$^2$ PO day 1 only | Grade III 15% | Nausea/Vomiting 11% |
| Vincristine 1.4 mg/m$^2$ IV on days 8 and 29 | Grade IV 8% | Neuropathy 8% |
| Repeat cycle every 6-8 weeks | | |
| Temozolomide 150 mg/m$^2$/d PO days 1-5* | Neutropenia 2% | Fever 2% |
| Repeat cycle every 28 days | Leukopenia 2% | Thrombocytopenia 6% |
| *For patients who have previously received | | Nausea 10% |
| any chemotherapy. Dose for chemotherapynaive | | Vomiting 6% |
| patients was 200 mg/m$^2$/d. | | Headache 6% |
| | | Asthenia 6% |
| | | Fatigue 5% |
| | | Anemia Grade III-IV 1% |
| BREAST CANCER | | |
| Doxorubicin 60 mg/m$^2$ IV day 1 | Grade III 5% | Neutropenic Sepsis 3% |
| Cyclophosphamide 600 mg/m$^2$ IV day 1 | Grade IV 2% | Neutropenic Infection 3% |
| Repeat cycle every 21 days | | Vomiting 13% |
| | | Nausea 9% |
| | | Diarrhea <1% |
| | | Stomatitis 1% |
| | | Phlebitis 1% |
| | | Cardiac <1% |

| Drug Dose and Target | Leukopenia/ Neutropenia Toxicity | Other Grade III-IV Toxicities |
|---|---|---|
| Cyclophosphamide 500 mg/m$^2$ IV day 1<br>Doxorubicin 50 mg/m$^2$ IV day 1<br>5-Fluorouracil 500 mg/m$^2$ IV day 1<br>Repeat cycle every 21 days. | Leukopenia<br>Grade III 56%<br>Grade IV 25% | Gastrointestinal 20%<br>Stomatitis 2%<br>Alopecia 55%<br>Cardiac 1%<br>Thrombocytopenia 8%<br>Anemia Grade III-IV 9% |
| Capecitabine 1250 mg/m$^2$ PO twice daily days 1-14.<br>Repeat cycle every 21 days. | Grade III-IV 3% | Thrombocytopenia 4%<br>Hand-Foot Syndrome 10%<br>Diarrhea 14%<br>Nausea 4%<br>Vomiting 4%<br>Fatigue 7%<br>Stomatitis 3%<br>Dehydration 4%<br>Anemia Grade III-IV 4% |
| Cyclophosphamide 500 mg/m$^2$ IV day 1<br>Epirubicin 100 mg/m$^2$ IV day 1<br>5-Fluorouracil 500 mg/m$^2$ IV day 1<br>Repeat cycle every 28 days | Grade III-IV 86% | Neutropenic Infection (Grade IV) or<br>Neutropenic Fever 8%<br>Thrombocytopenia 6%<br>Nausea/Vomiting 30%<br>Mucositis 10%<br>Alopecia 72%<br>Cardiac Toxicity* 11%<br>*>15% drop from baseline<br>or >10% drop below low level of normal<br>Anemia Grade III-IV 7% |
| Docetaxel 100 mg/m$^2$ IV over 1 hr every 21 days | Grade III-IV 93% | Neutropenic Fever 9%<br>Neutropenic Infection (Grade III-IV) 11%<br>Thrombocytopenia 4%<br>Nausea 5%<br>Vomiting 3%<br>Stomatitis 9%<br>Diarrhea 8%<br>Skin Toxicity 4%<br>Asthenia 16%<br>Neurosensory 5%<br>Severe Fluid Retention 8% |
| Docetaxel 75 mg/m$^2$ IV day 1<br>Capecitabine 1250 mg/m$^2$ PO twice daily days 1-14<br>Repeat cycle every 3 weeks | Neutropenia<br>Grade III 19%<br>Grade IV 44% | Hyperbilirubinemia 8.8%<br>Diarrhea 14%<br>Stomatitis 17%<br>Hand-Foot Syndrome 24%<br>Nausea 6%<br>Fatigue/Asthenia 7% |
| Doxorubicin 50 mg/m$^2$ IV day 1<br>Docetaxel 75 mg/m$^2$ IV day 1<br>Repeat cycle every 21 days | Grade III-IV 97% | Febrile Neutropenia 33%<br>Neutropenic Infection (Grade III-IV) 8%<br>Allergy 1%<br>Nausea 6%<br>Vomiting 6%<br>Stomatitis 9%<br>Diarrhea 8%<br>Asthenia 9%<br>Edema 1%<br>Nail Changes 1%<br>Cardiac 6% |
| Doxorubicin 50 mg/m$^2$ IV day 1, followed 24 hours later by<br>Paclitaxel 220 mg/m$^2$ IV over 3 hours day 2.<br>Repeat cycle every 21 days. | Neutropenia<br>Grade III 27%<br>Grade IV 62% | Infection (Grade III) 2%<br>Fever 8%<br>Thrombocytopenia (Grade IV) 2%<br>Arthralgia/Myalgia (Grade III) 10%<br>Peripheral Neuropathy (Grade III) 12%<br>Nausea/Vomiting (Grade III) 8%<br>Diarrhea (Grade III) 2%<br>Stomatitis (Grade III) 1%<br>Anemia Grade III-IV 9% |

-continued

| Drug Dose and Target | Leukopenia/ Neutropenia Toxicity | Other Grade III-IV Toxicities |
|---|---|---|
| Paclitaxel 135 mg/m$^2$ IV over 3 hrs, day 1<br>Vinorelbine 30 mg/m$^2$ IV days 1, 8<br>Repeat cycle every 28 days | Grade III 22%<br>Grade IV 71% | Neutropenic Fever 18%<br>(Most common with increased LFTs)<br>Thrombocytopenia 4%<br>Constipation 2%<br>Nausea/Vomiting 2%<br>Alopecia 86%<br>Phlebitis 12%<br>Anemia Grade III-IV 12% |
| Paclitaxel 135 mg/m$^2$ IV over 3 hrs, day 1<br>Vinorelbine 30 mg/m$^2$ IV days 1, 8<br>Repeat cycle every 28 days | Grade III 22%<br>Grade IV 71% | Neutropenic Fever 18%<br>(Most common with increased LFTs)<br>Thrombocytopenia 4%<br>Constipation 2%<br>Nausea/Vomiting 2%<br>Alopecia 86%<br>Phlebitis 12%<br>Anemia Grade III-IV 12% |
| Trastuzumab 4 mg/kg load IV followed by 2 mg/kg IV weekly, followed by Vinorelbine 25 mg/m$^2$ IV weekly<br>Assessment done at 8-week intervals | Grade III-IV 30% | Headache 3%<br>Pancreatitis 3% |
| Vinorelbine 30 mg/m$^2$ IV weekly | Grade III-IV 72% | Neutropenic Infection <1%<br>Thrombocytopenia 1%<br>Nausea/Vomiting <1%<br>Alopecia 1%<br>Stomatitis <1%<br>Neuropathy 1%<br>Constipation 3%<br>Anemia Grade III-IV 5% |
| GASTROINTESTINAL: COLON CANCER | | |
| Capecitabine 1250 mg/m$^2$ PO twice daily days 1-14<br>Repeat cycle every 3 weeks | Leukopenia<br>Grade III 0.3%<br>Neutropenia<br>Grade III 1.3%<br>Grade IV 1.3% | Thrombocytopenia 1%<br>Diarrhea 15.4%<br>Hand-Foot Syndrome 18.1%<br>Hyperbilirubinemia 17.3%<br>Stomatitis 3%<br>Hyperglycemia 8.7%<br>Anemia Grade III-IV 1.3% |
| 5-Fluorouracil 750 mg/m$^2$/d IV continuous infusion, days 1-7<br>Repeat cycle every 21 days | Grade III-IV 0% | Diarrhea* 22%<br>Stomatitis* 31%<br>Hand-Foot Syndrome* 14%<br>*Grade II-IV toxicity |
| Leucovorin 20 mg/m$^2$/d IV days 1-5<br>5-Fluorouracil 425 mg/m$^2$/d IV following leucovorin, days 1-5<br>Repeat cycle at 4 weeks, 8 weeks, then every 5 weeks thereafter | Leukopenia<br>Grade III-IV 21% | Nausea* 10%<br>Vomiting* 9%<br>Diarrhea* 14%<br>Stomatitis* 26%<br>Alopecia 34%<br>*Toxicity ungraded, but listed as severe |
| Irinotecan 350 mg/m$^2$ IV over 30 minutes<br>Repeat cycle every 21 days | Pretreated pts<br>Grade III-IV 47%<br>Naïve pts<br>Grade III-IV 48% | Neutropenic Fever 14%<br>Documented Infection 5%<br>Pre-treated patients (n = 165)<br>Thrombocytopenia 3%<br>Delayed Diarrhea 39%<br>Nausea/Vomiting 22%<br>Alopecia 53%<br>Anemia Grade III-IV 10%<br>Naïve pts (n = 48)<br>Thrombocytopenia 2%<br>Delayed Diarrhea 35%<br>Nausea/Vomiting 13%<br>Alopecia 54%<br>Anemia Grade III-IV 8% |

| Drug Dose and Target | Leukopenia/ Neutropenia Toxicity | Other Grade III-IV Toxicities |
|---|---|---|
| Irinotecan 180 mg/m$^2$ IV day 1<br>5-Fluorouracil 400 mg/m$^2$ IV, followed by<br>600 mg/m$^2$ IV infusion over 22 hours<br>plus leucovorin 200 mg/m$^2$<br>on days 1 and 2<br>Repeat cycle every 2 weeks | Grade III-IV 29% | Neutropenic Fever<br>Without Infection 9%<br>Neutropenic Infection 2%<br>Diarrhea 44%<br>Nausea 7%<br>Vomiting 11%<br>Asthenia 7%<br>Anorexia 7%<br>Abdominal Pain 6%<br>Cholinergic Syndrome 2%<br>Pain 2%<br>Weight Loss 2%<br>Anemia Grade III-IV 6% |
| Irinotecan 125 mg/m$^2$ IV over 90 minutes<br>days 1, 8, 15, 22, followed by<br>Leucovorin 20 mg/m$^2$ IV<br>days 1, 8, 15, 22, followed by<br>5-Fluorouracil 500 mg/m$^2$ IV<br>days 1, 8, 15, 22<br>Repeat cycle every 6 weeks | Neutropenia<br>Grade III 29.8%<br>Grade IV 24% | Neutropenic Fever 7.1%<br>Neutropenic<br>Infection 1.8%<br>Diarrhea 22.7%<br>Vomiting 9.7%<br>Mucositis (Grade III) 2.2% |

GASTROINTESTINAL: COLORECTAL CANCER

| Irinotecan 125 mg/m$^2$ IV over 90 minutes<br>days 1, 8, 15, 22, followed by<br>Leucovorin 20 mg/m$^2$ IV<br>days 1, 8, 15, 22, followed by<br>5-Fluorouracil 500 mg/m$^2$ IV<br>days 1, 8, 15, 22<br>Repeat cycle every 6 weeks | Neutropenia<br>Grade III 29.8%<br>Grade IV 24% | Neutropenic Fever 7.1%<br>Neutropenic<br>Infection 1.8%<br>Diarrhea 22.7%<br>Vomiting 9.7%<br>Mucositis (Grade III) 2.2% |

GASTROINTESTINAL: ESOPHAGEAL CANCER

| Cisplatin 100 mg/m$^2$ IV day 1<br>5-Fluorouracil 1000 mg/m$^2$/d IV continuous infusion, days 1-5<br>Repeat cycle every 21 days | Leukopenia<br>Grade III-IV 14% | Febrile Neutropenia<br>Leading to Septicemia and Death 5%<br>Nausea/Vomiting (Grade III) 27%<br>Thrombocytopenia 14%<br>Diarrhea (Grade III) 2%<br>Mucositis (Grade III) 4%<br>Vascular Thrombosis (Grade III) 9% |

GASTROINTESTINAL: GASTRIC CANCER

| Etoposide 120 mg/m$^2$ IV days 4, 5, 6<br>Doxorubicin 20 mg/m$^2$ IV days 1, 7<br>Cisplatin 40 mg/m$^2$ IV days 2, 8<br>Repeat cycle every 21-28 days | Leukopenia 30% | Neutropenic Sepsis 1%<br>Thrombocytopenia 9%<br>Mucositis 10%<br>Alopecia<br>(Grade II-IV) 100% |
| Leucovorin 300 mg/m$^2$/d IV over 10 minutes, followed by<br>Etoposide 120 mg/m$^2$/d IV over 50 minutes, followed by<br>5-Fluorouracil 500 mg/m$^2$/d IV over 10 minutes<br>All agents are given on days 1-3<br>Repeat cycle every 21-28 days | Leukopenia<br>Grade III 16%<br>Grade IV 4% | Neutropenic Infection 2%<br>Thrombocytopenia 4%<br>Diarrhea 7%<br>Alopecia 65%<br>Stomatitis<br>(Grade II-IV) 10% |
| 5-Fluorouracil 600 mg/m$^2$ IV days 1, 8, 29, 36<br>Doxorubicin 30 mg/m$^2$ IV days 1, 29<br>Mitomycin 10 mg/m$^2$ IV day 1<br>Repeat cycle every 8 weeks | Leukopenia 3% | Neutropenic Infection 20%<br>Infection (any)* 20%<br>Nausea/Vomiting* 58%<br>Thrombocytopenia 5%<br>Mucositis* 10%<br>Diarrhea* 28%<br>Alopecia* 57%<br>*Grade II-IV toxicity or unspecified<br>Anemia Grade III-IV 3% |

| Drug Dose and Target | Leukopenia/ Neutropenia Toxicity | Other Grade III-IV Toxicities |
|---|---|---|
| Methotrexate 1500 mg/m$^2$ IV day 1<br>5-Fluorouracil 1500 mg/m$^2$ IV starting 1 hour after methotrexate, day 1<br>Leucovorin 15 mg/m$^2$ PO q6h starting 24 hours after methotrexate dose, for 48 hours<br>Doxorubicin 30 mg/m$^2$ IV day 15<br>Repeat cycle every 28 days | | Neutropenic Sepsis 2%<br>Nausea/Vomiting 8%<br>Mucositis 10%<br>Diarrhea* 26%<br>Alopecia 24%<br>*Unspecified grade of toxicity |
| GASTROINTESTINAL: LIVER (HEPATOCELLULAR) CANCER | | |
| Gemcitabine 1250 mg/m$^2$ IV over 30 minutes days 1, 8, 15<br>Repeat cycle every 28 days | Leukopenia Grade III 10.7% | Infection (Grade III) 3.6%<br>Thrombocytopenia 10.7%<br>Hepatotoxicity (Grade III) 14.3%<br>Skin Rash (Grade III) 3.6%<br>Anemia Grade III 14.3% |
| GASTROINTESTINAL: PANCREATIC CANCER | | |
| 5-Fluorouracil 600 mg/m$^2$ IV days 1, 8, 29, 36<br>Doxorubicin 30 mg/m$^2$ IV days 1, 29<br>Mitomycin 10 mg/m$^2$ IV day 1<br>Repeat cycle every 72 days | Leukopenia Grade III 16%<br>Grade IV 6% | Thrombocytopenia 30%<br>Hepatic 1%<br>Renal 2%<br>Nausea/Vomiting 11%<br>Cardiac 2% |
| Gemcitabine 1000 mg/m$^2$ IV over 30 minutes once weekly for 7 weeks, followed by a 1-week rest period<br>Subsequent cycles once weekly for 3 consecutive weeks out of every 4 weeks | Grade III 19%<br>Grade IV 7% | Thrombocytopenia 10%<br>Increased Bilirubin 41%<br>Nausea/Vomiting 13%<br>Diarrhea 2%<br>Constipation 3%<br>Pain 2%<br>State of Consciousness 2%<br>Anemia Grade III-IV 10% |
| GASTROINTESTINAL: RECTAL CANCER | | |
| Leucovorin 500 mg/m$^2$ IV over 2 hours, 1 hour prior to 5-fluorouracil, every week × 6 weeks, then 2 weeks off<br>5-Fluorouracil 500 mg/m$^2$ IV bolus every week × 6 weeks, then 2 weeks off<br>5-Fluorouracil 400 mg/m$^2$ IV bolus daily on days 1-3 and the last 3 days of radiation therapy<br>Duration of each cycle: 10 weeks<br>5-Fluorouracil/leucovorin for a total of 6 cycles<br>Radiation therapy initiated between 3 and 5 weeks following completion of cycle 1 | Leukopenia <4 × 10³/mm³ 65%<br>Leukopenia <2 × 10³/mm³ 3% | Infection (any) 14% (systemic +/or sepsis) 3%<br>Fever (any) 9% (>40° C. or hypotension) 1%<br>Thrombocytopenia <100K 4%<br>Nausea/Vomiting (any) 59% (severe or with hospitalization) 4%<br>Diarrhea (≥3 stools/day) 61% (≥7 stools/day) 31%<br>Stomatitis (any) 21%<br>Dermatitis (any) 25% (severe) 3% |
| GENITOURINARY: BLADDER CANCER | | |
| Cisplatin 30 mg/m$^2$ IV days 1, 8, 15, 22, 29, 36, 43, 50<br>Docetaxel 40 mg/m$^2$ IV days 4, 11, 18, 25, 32, 39, 46, 53 | Grade III-IV 8% | Neutropenic Fever 8%<br>Nausea/Vomiting 8%<br>Diarrhea 35%<br>Abdominal Pain 35%<br>Urinary Frequency 19%<br>Dysuria 14%<br>Severe Cystitis 8%<br>Thrombocytopenia 11%<br>Anemia Grade III-IV 16% |

| Drug Dose and Target | Leukopenia/ Neutropenia Toxicity | Other Grade III-IV Toxicities |
|---|---|---|
| Paclitaxel 175 mg/m$^2$ IV over 3 hours day 1, followed by<br>Cisplatin 75 mg/m$^2$ IV over 1-2 hours day 1 after paclitaxel<br>Repeat cycle every 21 days | Granulocytopenia Grade III-IV 52% | Neutropenic Fever 1.9%<br>Infection (non-neutropenic) 9.6%<br>Nausea/Vomiting 29%<br>Neurosensory 15.4%<br>Neuromotor 11.5%<br>Metabolic 17.3%<br>Cardiac 7.7%<br>Pulmonary 3.8%<br>Neuropsychological/ Neuroclinical 7.7%<br>Hepatotoxicity 3.8%<br>Anemia Grade III 9.6% |
| Gemcitabine 1000 mg/m$^2$ IV days 1, 8, 15<br>Cisplatin 70 mg/m$^2$ IV day 2<br>Repeat cycle every 28 days | Neutropenia<br>Grade III 41.2%<br>Grade IV 29.9% | Neutropenic Fever 2%<br>Neutropenic Sepsis 1%<br>Thrombocytopenia 57%<br>Nausea/Vomiting (Grade III) 22%<br>Alopecia (Grade III) 10.5%<br>Diarrhea (Grade III) 3%<br>Hematuria (Grade III) 4.5%<br>Pulmonary 3%<br>Anemia Grade III-IV 27% |
| Gemcitabine 1200 mg/m$^2$ IV days 1, 8, 15<br>Repeat cycle every 28 days | Grade III-IV 20% | Neutropenic Fever 3%<br>Thrombocytopenia 5%<br>Nausea/Vomiting 5%<br>Fever 3%<br>Edema 5%<br>Deep Vein Thrombosis 3%<br>Respiratory 5%<br>CNS 3%<br>Anemia Grade III-IV 3% |
| Methotrexate 30 mg/m$^2$ IV days 1, 15, 22<br>Vinblastine 3 mg/m$^2$ IV days 2, 15, 22<br>Doxorubicin 30 mg/m$^2$ IV day 2<br>Cisplatin 70 mg/m$^2$ IV day 2<br>Repeat cycle every 28 days | Leukopenia<br>Grade III 38%<br>Grade IV 20 | Neutropenia<br>Nadir Sepsis 25%<br>Nausea/Vomiting 7%<br>Thrombocytopenia 21%<br>Mucositis 13%<br>Renal 2%<br>Hepatic 5%<br>Diarrhea 2% |
| Paclitaxel 250 mg/m$^2$ IV over 24 hours, day 1<br>Repeat cycle every 21 days | Grade III-IV 23%<br>All patients received G-CSF | Neutropenic Fever* 8%<br>Neuropathy 12%<br>Mucositis 12%<br>Diarrhea (Grade IV) 4%<br>*All pts received G-CSF |
| Paclitaxel 200 mg/m$^2$ IV over 1 hour on day 1<br>Gemcitabine 1000 mg/m$^2$ IV over 30 minutes on days 1, 8, and 15<br>Repeat cycle every 21 days | Leukopenia<br>Grade III 37%<br>Grade IV 9% | Thrombocytopenia (Grade III) 13%<br>Fatigue/Asthenia 11%<br>Peripheral Neuropathy 11%<br>Nausea/Vomiting 7%<br>Arthralgia/Myalgia 6%<br>Skin Rash 6%<br>Hypersensitivity Reaction 4%<br>Pneumonitis 2%<br>Anemia Grade III 28% |
| Paclitaxel 225 mg/m$^2$ over 3 hours on day 1<br>Carboplatin targeted by Calvert equation to AUC of 6 IV day 1 after paclitaxel<br>Repeat cycle every 21 days | Grade III-IV 41% | Neutropenic Fever 12%<br>Thrombocytopenia 4%<br>Nausea/Vomiting 12%<br>Neuropathy 20% |

| Drug Dose and Target | Leukopenia/ Neutropenia Toxicity | Other Grade III-IV Toxicities |
|---|---|---|
| GENITOURINARY: PROSTATE CANCER ||| 
| Estramustine 10 mg/kg/d PO (3 divided doses) days 1-5 on an empty stomach<br>Docetaxel 70 mg/m$^2$ IV over 1 hour day 2<br>Hydrocortisone 30 mg PO every morning and 10 mg every evening continuously<br>Repeat estramustine/docetaxel cycles every 21 days. | Leukopenia<br>Grade III 57%<br>Grade IV 4%<br>Neutropenia<br>Grade III 26%<br>Grade IV 30% | Infection<br>(site unknown) 24%<br>Thrombocytopenia 20%<br>Hyperglycemia 18%<br>Hypocalcemia<br>(Grade III) 2%<br>Phlebitis/Thrombosis 6%<br>Edema 22%<br>Malaise/Fatigue/<br>Asthenia 24%<br>Stomatitis/Esophagitis<br>(Grade III) 6%<br>Nausea (Grade III) 4%<br>Vomiting (Grade IV) 2%<br>Diarrhea 6%<br>Anorexia 4%<br>Hepatic 22%<br>Dyspnea 22%<br>Dysrhythmias<br>(Grade III) 2%<br>Ischemia (Grade III) 7%<br>BUN/SCr (Grade III) 9%<br>Renal Failure<br>(Grade IV) 2%<br>Neurologic (Grade III) 8% |
| Estramustine 200 mg/m$^2$ PO tid days 1-42<br>Vinblastine 4 mg/m$^2$ IV weekly for 6 weeks, begin day 1<br>Repeat cycle every 8 weeks | Grade III 7%<br>Grade IV 1% | Neutropenic Infection 7%<br>Thrombocytopenia* 1%<br>Nausea* 28%<br>Leg Edema* 12%<br>Fatigue* 16%<br>Neurologic* 12%<br>Constipation* 3%<br>Cardiac* 5%<br>*Grade II-IV toxicity |
| Mitoxantrone 12 mg/m$^2$ IV day 1<br>Prednisone 5 mg PO bid continuously<br>Repeat cycle every 21 days | Grade III-IV 45% | Neutropenic Sepsis 1%<br>Thrombocytopenia 5%<br>Cardiac 4%<br>Nausea/Vomiting <1%<br>Alopecia 24% |
| Paclitaxel 30 mg/m$^2$/d IV continuous infusion days 1-4<br>Estramustine 600 mg PO daily 24 hr before paclitaxel (2 to 3 divided doses)<br>Repeat cycle every 21 days | Leukopenia<br>Grade III-IV<br>21% | Neutropenic Fever 6%<br>Edema 15%<br>Cardiovascular 6%<br>Anorexia 21%<br>Fatigue 9%<br>Nausea 6%<br>Hepatic 9%<br>Venous Thrombosis 3%<br>Vomiting 3%<br>Diarrhea 3% |
| Vinorelbine 25 mg/m$^2$ IV days 1, 8<br>Estramustine 140 mg PO three times a day days 1-14<br>Repeat cycle every 3 weeks | Leukopenia<br>Grade III 4% | Infection 4%<br>Deep Vein Thrombosis 4%<br>Myocardial Ischemia 4%<br>Fatigue 4%<br>Hearing Loss 4%<br>Dyspnea 4% |
| GENITOURINARY: RENAL CELL CANCER |||
| Interferon alfa-2a 3 MU SQ daily, escalated by 3 MU increments every 7 days, as tolerated to a maximum dose of 9 MU SQ daily | Neutropenia<br>Grade III 3%<br>Leukopenia<br>Grade III 7% | Thrombocytopenia<br>(Grade III) 1%<br>Gastrointestinal<br>(Grade III) 13%<br>Altered Mood<br>(Grade III) 3%<br>Neurologic Toxicity 3%<br>Cardiac Toxicity 5%<br>Anemia Grade III-IV 11% |

-continued

| Drug Dose and Target | Leukopenia/ Neutropenia Toxicity | Other Grade III-IV Toxicities |
|---|---|---|
| Interferon alfa-2a 18 MU SQ TIW × 10 weeks (induction) then × 13 additional weeks (maintenance) | Leukopenia 0.7% | Fever 5% Nausea/Vomiting 5% Pulmonary Symptoms 3% Increased AST/ALT 3% Weight Loss 6% Anemia Grade III-IV 6% |
| Interleukin-2 18 MU/m$^2$/d as an IV continuous infusion × 5 days Interferon alfa-2a 6 MU SQ TIW Treatment consists of 2 induction cycles and 4 maintenance cycles, with a 3-week rest period between cycles. An induction cycle consists of two 5-day courses, separated by a 6-day rest period. Interferon-alfa is given during the two induction cycles and during each maintenance cycle. | Leukopenia 2% | Infection 9% Fever 56% Hypotension Resistant to Vasopressors 67% Nausea/Vomiting 31% Diarrhea 25% Pulmonary Symptoms 15% Renal Symptoms 16% Neurologic Symptoms 14% Increased AST/ALT 11% Cutaneous Signs 14% Cardiac Signs 6% Thrombocytopenia 7% Increased Creatinine 5% Hyperbilirubinemia 2% Anemia Grade III-IV 16% |
| Interleukin-2 600,000 or 720,000 IU/kg IV over 15 minutes every 8 hours × 14 doses Repeat after a 9-day rest period. | None reported | Sepsis 6% Fever and/or Chills 24% Oliguria/Anuria 46% Mental Status Changes 28% Nausea/Vomiting 25% Diarrhea 22% Hyperbilirubinemia 21% Thrombocytopenia 21% Dyspnea 17% Hypotension 74% Elevated BUN/ Creatinine 14% Increased AST/ALT 10% Cardiac Toxicity 9% Increased Alkaline Phosphatase 8% Acidosis 6% Asthenia 4% Pruritus 4% Stomatitis 4% Gastrointestinal Bleeding 4% Anemia Grade III-IV 18% |
| GENITOURINARY: TESTICULAR CANCER | | |
| Bleomycin 30 units IV days 2, 9, 16 Etoposide 100 mg/m$^2$/d IV days 1-5 Cisplatin 20 mg/m$^2$/d IV days 1-5 Repeat cycle every 21 days × 4 | Hematologic Grade III 39% Grade IV 34% | Neutropenic Infection 5% Nausea/Vomiting 70% Neurologic 7% Respiratory 5% Hepatic 3% Pulm. Hemorrhage <1% Resp. Failure 1% |
| Etoposide 100 mg/m$^2$/d IV days 1-5 Cisplatin 20 mg/m$^2$/d IV days 1-5 Repeat cycle every 21 days | At day 21 24% | Neutropenic Nadir Sepsis 10% Nausea/Vomiting* 44% Stomatitis 2% Alopecia† ~100% *Grade I-II toxicity †Unknown grade of toxicity |
| Cisplatin 20 mg/m$^2$/d IV days 1-5 Vinblastine 0.15 mg/kg IV days 1, 2 Bleomycin 30 units IV days 2, 9, 16 Repeat cycle every 21 days | Grade III-IV 59% | Neutropenic Sepsis 4% Thrombocytopenia 5% Paresthesias* 38% Abdominal Pain* 20% Myalgias* 19% *Unknown grade |

| Drug Dose and Target | Leukopenia/ Neutropenia Toxicity | Other Grade III-IV Toxicities |
|---|---|---|
| Vinblastine 0.11 mg/kg IV days 1, 2<br>Ifosfamide 1200 mg/m$^2$/d IV days 1-5<br>(with mesna uroprotection)<br>Cisplatin 20 mg/m$^2$/d IV days 1-5<br>Repeat cycle every 21 days | | Toxicity data reported<br>on 17 patients:<br>89% neutropenic fever<br>requiring antibiotics<br>59% required RBC<br>transfusions<br>35% required platelet<br>transfusions<br>1 therapy-related death<br>due to CNS toxicity |
| Etoposide 75 mg/m$^2$/d IV days 1-5<br>Ifosfamide 1200 mg/m$^2$/d IV days 1-5<br>Cisplatin 20 mg/m$^2$/d IV days 1-5<br>Mesna 120 mg/m$^2$ IV 15 minutes prior to<br>ifosfamide, then 1200 mg/d IV continuous<br>infusion days 1-5<br>Repeat cycle every 21 days | Hematologic<br>Grade III 60% | Neutropenic Infection 6%<br>Nausea/Vomiting 9%<br>Neurological 8%<br>Respiratory 40%<br>Hepatic 3%<br>Renal 5% |
| GYNECOLOGIC: CERVICAL CANCER ||| 
| Cisplatin 100 mg/m$^2$ IV day 1<br>Repeat cycle every 21 days | Leukopenia<br>Grade III-IV 7% | Thrombocytopenia 1%<br>Nephrotoxicity (SCr > 2.0<br>or BUN > 40) 14%<br>Nausea/Vomiting*<br>74%-83%<br>Hearing Loss (clinical)<br>12%<br>Neurotoxicity 7%<br>*Toxicity grading<br>unknown |
| Radiation therapy 1.7 Gy/d on<br>days 1-5 of each week, for a total of<br>29 fractions (49.3 Gy)<br>Cisplatin 70 mg/m$^2$ IV over 2 hours day 1<br>5-Fluorouracil 1000 mg/m$^2$/d IV continuous<br>infusion days 1-4<br>2nd cycle began on day 22, the 3rd and 4th<br>chemotherapy cycles scheduled after completion<br>of RT, to begin on days 43 and 64 | Leukopenia<br>Grade III 33%<br>Grade IV 2.5%<br>Granulocytopenia<br>Grade III 19.6%<br>Grade IV 9% | Infection (Grade III)<br>0.8%<br>Diarrhea 9.8%<br>Nausea (Grade III) 14%<br>Small Bowel Obstruction<br>(Grade IV) 1.6%<br>Stomatitis 2.4%<br>Vomiting 12.3%<br>Anemia Grade III-IV<br>3.3% |
| Cisplatin 50 mg/m$^2$ IV days 1, 29<br>5-Fluorouracil 1000 mg/m$^2$/d IV continuous<br>infusion days 1-4 and 29-32<br>Hydroxyurea 2000 mg/m$^2$ PO<br>twice weekly two hours before<br>radiotherapy at weeks 1-6 | Leukopenia<br>Grade III 41%<br>Grade IV 5% | Thrombocytopenia 4%<br>Gastrointestinal 18%<br>Genitourinary 2%<br>Cutaneous 5%<br>Neurologic 1%<br>Cardiovascular 2%<br>Fatigue 1%<br>Pain 1%<br>Weight Loss 2% |
| Cisplatin 80 mg/m$^2$ IV day 1<br>Vinorelbine 25 mg/m$^2$ IV days 1, 8<br>Repeat cycle every 21 days | Grade III* 52%<br>Grade IV* 4%<br>*Per cycle | Neutropenic Fever 0%<br>Nausea/Vomiting 6%<br>Peripheral Neuropathy<br>2%<br>Alopecia 4%<br>Anemia Grade III-IV<br>10% |
| Cisplatin 40 mg/m$^2$ IV each week<br>during XRT (not to exceed 70 mg/wk) ×<br>6 doses maximum<br>XRT 1.8-2.0 Gy daily, 5 days per week<br>for a total of 45 Gy, followed by local<br>brachytherapy and hysterectomy | Leukopenia<br>Grade III 18%<br>Grade IV 3% | Gastrointestinal 14% |
| Paclitaxel 135 mg/m$^2$ IV over 24 hours<br>day 1, followed by<br>Cisplatin 75 mg/m$^2$ IV day 2<br>Repeat cycle every 21 days. | Grade III 16%<br>Grade IV 61% | Neutropenic Fever 28%<br>Fever 5%<br>Thrombocytopenia 18%<br>Gastrointestinal 36%<br>Neurologic 7%<br>Cardiac 7%<br>Pulmonary 7%<br>Dehydration 2%<br>Electrolyte<br>Abnormalities 2%<br>Pneumonia 2%<br>Anemia Grade III-IV<br>25% |

| Drug Dose and Target | Leukopenia/ Neutropenia Toxicity | Other Grade III-IV Toxicities |
|---|---|---|
| GYNECOLOGIC: ENDOMETRIAL CANCER | | |
| Doxorubicin 60 mg/m$^2$ IV day 1<br>Cisplatin 60 mg/m$^2$ IV day 1 given 12 hours after doxorubicin<br>Repeat cycle every 28 days | Leukopenia<br>Grade III 17%<br>Grade IV 43% | Thrombocytopenia 20%<br>Nausea/Vomiting* 53%<br>*Mild to severe anemia Grade III-IV (Hgb < 10 g) 63% |
| Doxorubicin 60 mg/m$^2$ IV day 1<br>Repeat cycle every 21 days | Grade III-IV 8% | Gastrointestinal 3% |
| GYNECOLOGIC: OVARIAN CANCER | | |
| Altretamine 260 mg/m$^2$/d PO<br>(divided into 3 or 4 doses) days 1-14<br>Repeat cycle every 28 days | | Nausea 14%<br>Vomiting 12%<br>Fatigue 9%<br>Neurologic 2%<br>Anemia Grade III-IV 2% |
| Paclitaxel 175 mg/m$^2$ IV over 3 hrs, day 1, followed by<br>Carboplatin dose targeted by the Calvert equation to AUC of 5, IV day 1<br>Repeat cycle every 21 days. | Grade III 31%<br>Grade IV 45% | Nausea/Vomiting 16%<br>Neurotoxicity 1%<br>Thrombocytopenia 4% |
| Cisplatin 100 mg/m$^2$ IV day 1<br>Repeat cycle every 21 days | Grade III 36%<br>Grade IV 12% | Neutropenic Fever <1%<br>Thrombocytopenia 4%<br>Gastrointestinal 33%<br>Renal 4%<br>Neurologic 11%<br>Cardiovascular 2%<br>Anemia Grade III-IV 11% |
| Paclitaxel 135 mg/m$^2$ IV continuous infusion over 24 hours day 1, followed by<br>Cisplatin 75 mg/m$^2$ IV day 2<br>Repeat cycle every 21 days. | Neutropenia Grade III 49%<br>Grade IV 13% | Infection 2%<br>Fever 2%<br>Thrombocytopenia 3%<br>Other Hematologic 88%<br>Gastrointestinal 17%<br>Cardiovascular 3%<br>Neurologic 9%<br>Metabolic 2%<br>Creatinine Clearance 2%<br>Allergic Reaction 2%<br>Fatigue (Grade III) 1%<br>n = 32 |
| Docetaxel 100 mg/m$^2$ IV over 1 hour day 1<br>Repeat cycle every 21 days. | Granulocytopenia<br>Grade III 6%<br>Grade IV 72% | Febrile Neutropenia 33%<br>Thrombocytopenia (Grade III) 6%<br>anemia Grade III 32% |
| Docetaxel 75 mg/m$^2$ IV over 1 hour day 1, followed by<br>Carboplatin AUC of 5 (via CrEDTA) or AUC of 6 (if CrCl calculated using Cockroft and Gault formula) IV day 1<br>Repeat cycle every 21 days. | Neutropenia<br>Grade III 9%<br>Grade IV 77%<br>Leukopenia<br>Grade III 59%<br>Grade IV 5% | Febrile Neutropenia (Grade IV) 3%<br>Neutropenia >7 days (Grade IV) 14%<br>Thrombocytopenia 14%<br>Nausea (Grade III) 5%<br>Vomiting (Grade III) 5%<br>Fatigue (Grade III) 5%<br>Anemia Grade III-IV 14% |
| Liposomal doxorubicin 50 mg/m$^2$ IV day 1<br>Repeat cycle every 21 days | Grade III-IV 20% | Neutropenic Fever 11%<br>Stomatitis 14%<br>Palmar-Plantar Erythrodysesthesia 29% |
| Paclitaxel 135 mg/m$^2$ IV over 3 or 24 hrs, day 1<br>Repeat cycle every 21 days. | Leukopenia<br>Grade III-IV 78% | Neutropenic Fever 33%<br>Infection 12%<br>Cardiac 2%<br>Thrombocytopenia 8%<br>Vomiting 7%<br>Mucositis 1%<br>Neurologic 2% |

-continued

| Drug Dose and Target | Leukopenia/ Neutropenia Toxicity | Other Grade III-IV Toxicities |
|---|---|---|
| Topotecan 1.5 mg/m$^2$/d IV over 30 min, days 1-5 Repeat cycle every 21 days | Grade III 15% Grade IV 82% | Neutropenic Fever 18% (after these adverse effects, G-CSF was given) Sepsis 9% Nausea 7% Vomiting 4% Fatigue 5% Thrombocytopenia 52% Severe Bleed <1% Anemia Grade III-IV 49% |
| GYNECOLOGIC: UTERINE SARCOMA | | |
| Ifosfamide 1500 mg/m$^2$/d IV days 1-5 Mesna uroprotection at equivalent doses to ifosfamide via IV continuous infusion Repeat cycle every 21 days | Neutropenia Grade III 28% Grade IV 31% Granulocytopenia Grade III 8% Grade IV 28% | Thrombocytopenia 5% Nausea/Vomiting (Grade III) 4% Other Gastrointestinal (Grade IV) 1% Creatinine Elevation (Grade III) 2% Neurologic-Central (Grade III) 19% Neurologic-Peripheral (Grade IV) 1% Hematuria (Grade III) 1% Anemia Grade III-IV 8% |
| HEAD & NECK CANCER | | |
| Carboplatin 300 mg/m$^2$ IV day 1 5-Fluorouracil 1000 mg/m$^2$/d IV continuous infusion days 1-5 Repeat cycle every 28 days | Leukopenia Grade III 9% Grade IV 2% | Neutropenic Sepsis 1% Nausea/Vomiting 6% Thrombocytopenia 13% Diarrhea 2% Stomatitis 15% Renal Toxicity 1% Anemia Grade III-IV 14% |
| Paclitaxel 175 mg/m$^2$ IV over 3 hours day 1 Ifosfamide 1000 mg/m$^2$/d IV over 2 hours days 1-3 Mesna 200 mg/m$^2$ before ifosfamide and 400 mg/m$^2$ after ifosfamide days 1-3 Carboplatin targeted to an AUC of 6 (Calvert formula) as a 30-minute IV infusion day 1 Repeat cycle every 21-28 days. | Neutropenia Grade III-IV 92% | Neutropenic Fever (Grade V*) 2% Fatigue (Grade III) 6% Nausea/Emesis (Grade III) 4% Peripheral Sensory Neuropathy (Grade III) 2% Myalgia/Arthralgia (Grade III) 2% Nephrotoxicity (Grade III) 2% Anorexia (Grade III) 4% *NCIC criteria used, scale Grade 0-V |
| Paclitaxel 175 mg/m$^2$ over 3 hours on day 1 Ifosfamide 1000 mg/m$^2$/d over 2 hours on days 1-3 Mesna 400 mg/m$^2$ IV before ifosfamide and 200 mg/m$^2$ IV, 4 hr after ifosfamide days 1-3 Cisplatin 60 mg/m$^2$ IV day 1 Repeat cycle every 21-28 days. | Grade III-IV 90% | Neutropenic Fever 27% Pneumonia 15% Nausea/Vomiting 6% Anorexia 4% Fatigue 15% Peripheral Neuropathy 6% Renal Toxicity 2% Mucositis 2% Orthostatic Hypotension 4% |
| LEUKEMIAS: ACUTE LYMPHOBLASTIC, ADULT | | |
| Methotrexate 200 mg/m$^2$ IV over 2 hours day 1, followed by: Methotrexate 800 mg/m$^2$ IV over 24 hours day 1 Calcium leucovorin 15 mg PO every 6 hours × 8 doses starting 24 hours after completion of the MTX infusion-dose adjusted based on MTX levels Cytarabine 3000 mg/m$^2$ IV over 2 hours every 12 hours on days 2 and 3 (4 doses total) | | Sepsis 11% Pneumonia 5% Fungal Infections <1% Fever of Unknown Origin 23% Rash 5% Mucositis 5% Neurotoxicity 5% Rash and Desquamation of Palms/Feet 3% |

| Drug Dose and Target | Leukopenia/ Neutropenia Toxicity | Other Grade III-IV Toxicities |
|---|---|---|
| Methylprednisolone 50 mg IV twice daily days 1-3<br>G-CSF 5 mcg/kg SQ twice daily starting day 4 until ANC recovery<br>Cycle repeated when ANC >3 × 109/L and platelets >60 × 109/L (approximately 3-4 weeks) | | Diarrhea 1%<br>Cytarabine-Associated Fever 6% Nephrotoxicity (reversible) 1.5%<br>Cytarabine Neurotoxicity 2% |
| Cyclophosphamide 300 mg/m$^2$ IV over 3 hours every 12 hours days 1-3 (total 6 doses)<br>Mesna 600 mg/m$^2$/d IV continuous infusion days 1-3-continue until 6 hours after last dose of cyclophosphamide<br>Vincristine 2 mg IV days 4, 11<br>Doxorubicin 50 mg/m$^2$ IV day 4<br>Dexamethasone 40 mg PO daily days 1-4 and days 11-14<br>G-CSF 5 mcg/kg SQ twice daily starting day 24 hours after the completion of chemotherapy and continuing until ANC recovery<br>Alternate cycles of Hyper-CVAD with HD MTX-Ara-C every 3-4 weeks (when WBC >3 × 109/L and platelet count >60 × 109/L) | Time to granulocytes >1 × 109/L: 18 days after the first cycle | Induction<br>Moderate-Severe Mucositis 6%<br>Moderate-Severe Diarrhea 3%<br>Disseminated Intravascular Coagulopathy Requiring Therapy 2%<br>Consolidation Neurotoxicity 8%<br>G-CSF-Induced Bone Pain 5% |
| LEUKEMIAS: ACUTE MYELOGENOUS | | |
| Fludarabine 30 mg/m$^2$/d IV over 30 minutes days 1-5<br>Cytarabine 2000 mg/m$^2$/d IV over 4 hours after completion of fludarabine days 1-5<br>G-CSF 5 mcg/kg/d IV day 0 (24 hours prior to starting chemotherapy) until ANC recovery | Neutropenia Grade IV 100% | Documented Infections (>Grade III) 44%<br>Bacterial Infections 34%<br>Fungal Infections 10%<br>Fever of Unknown Origin 44%<br>Mucositis (>Grade III) 10%<br>Diarrhea (>Grade III) 8%<br>Hepatic (>Grade III) 8%<br>Neurologic (>Grade III) 2% |
| Gemtuzumab 9 mg/m$^2$ IV over 2 hours<br>Recommended treatment course is a total of 2 doses with 14 days between the doses | Neutropenia Grade III-IV 98%<br>Leukopenia Grade III-IV 96% | Neutropenic Fever 7%<br>Sepsis 16%<br>Fever 15%<br>Chills 13%<br>Thrombocytopenia 99%<br>Dyspnea 9%<br>Pneumonia 7%<br>Nausea 9%<br>Hyperbilirubinemia 23%<br>Hyperglycemia 12%<br>Anemia Grade III-IV 47% |
| Idarubicin 12 mg/m$^2$/d IV days 1-3<br>Cytarabine 100 mg/m$^2$/d IV continuous infusion days 1-7<br>Only repeat if patient fails to achieve a remission | | Nausea/Vomiting 6%<br>Diarrhea 16%<br>Mucositis 7%<br>Hyperbilirubinemia 9%<br>Skin Rash 5%<br>Alopecia 40%<br>Cardiac Toxicity 11% |
| LEUKEMIAS: ACUTE MYELOGENOUS, INDUCTION | | |
| Cytarabine 100 mg/m$^2$/d IV continuous infusion days 1-5<br>Daunorubicin 45 mg/m$^2$/d IV days 1, 2<br>*For reinduction | | Neutropenic Infection 51%<br>Hemorrhage 20%<br>Hepatic 7%<br>Renal 5%<br>Cardiac 4% |
| Cytarabine 100 mg/m$^2$/d IV continuous infusion days 1-7<br>Daunorubicin 45 mg/m$^2$/d IV days 1-3 | | Neutropenic Infection 54%<br>Hemorrhage 12%<br>Hepatic 2%<br>Renal 4%<br>Gastrointestinal 1% |

| Drug Dose and Target | Leukopenia/ Neutropenia Toxicity | Other Grade III-IV Toxicities |
|---|---|---|
| Etoposide 200 mg/m²/d IV continuous infusion days 8-10<br>Mitoxantrone 12 mg/m²/d IV days 1-3<br>Cytarabine 500 mg/m²/d IV continuous infusion days 1-3, 8-10 | 100% | Neutropenic Infection 54%<br>Thrombocytopenia 100%<br>Mucositis 23%<br>Hyperbilirubinemia 8%<br>Bleeding 6%<br>Rash 5%<br>Diarrhea 3%<br>Metabolic Disorders 2%<br>Cerebellar Syndrome 1%<br>Vomiting 9% |
| LEUKEMIAS: ACUTE MYELOGENOUS, POSTREMISSION | | |
| Cytarabine 100 mg/m²/d IV continuous infusion days 1-5*<br>Repeat cycle every 28 days<br>*For patients >60 years of age | Grade III-IV >16% | Patients Requiring Hospitalization Due to Neutropenic Fever 16%<br>Patients Requiring Transfusions Due to Thrombocytopenia 28% |
| Cytarabine 3000 mg/m² IV over 3 hours every 12 hours days 1, 3, 5<br>Administer with saline, methylcellulose, or steroid eye drops OU, every 2-4 hours, beginning with cytarabine and continuing 48-72 hours after the last cytarabine dose<br>Repeat cycle every 28 days | Grade III-IV 71% | Neutropenic Fever 71%<br>Thrombocytopenia (Grade IV) 86%<br>CNS Toxicities 12% (32% with age >60 yrs) |
| LEUKEMIAS: ACUTE MYELOGENOUS, SALVAGE | | |
| Cyclophosphamide 1000 mg/m²/d IV over 2 hours days 1-3<br>Etoposide 200 mg/m²/d IV over 3 hours days 1-3<br>Carboplatin 150 mg/m²/d for 3 days IV continuous infusion days 1-3<br>Cytarabine 1000 mg/m²/d IV over 2 hours days 1-3 | | Neutropenic Fever 76%<br>Hyperbilirubinemia (Grade IV) 4%<br>Hemorrhagic Cystitis (Grade IV) 4%<br>Diarrhea (Grade III) 4%<br>Mucositis (Grade III) 4%<br>Cardiac Toxicity (Grade III) 4% |
| LEUKEMIAS: ACUTE PROMYELOCYTIC | | |
| Induction Therapy<br>Arsenic trioxide 0.15 mg/kg/d IV over 1-2 hours from day 1 until bone marrow remission (not greater than 60 doses)<br>Consolidation Therapy<br>Should begin 3-6 weeks after completion of induction therapy at a dose of 0.15 mg/kg/d for 25 doses over a period of up to 5 weeks | Neutropenia Grade III-IV 10% | Febrile Neutropenia 8%<br>Fever 5%<br>Disseminated Intravascular Coagulation 8%<br>Thrombocytopenia 12%<br>Arthralgia/Mylagia 13%<br>Dyspnea 10%<br>Sepsis 5%<br>Hypoxia 10%<br>Hypokalemia 13%<br>Hypomagnesemia 13%<br>Hyperglycemia 13%<br>Paresthesias 5%<br>Convulsions 5%<br>Leukocytosis 3%<br>Anemia Grade III-IV 5% |
| Induction<br>Cytarabine 100 mg/m²/d IV continuous infusion days 1-7<br>Daunorubicin 45 mg/m²/d IV days 1-3<br>Consolidation<br>First cycle-identical to induction<br>Second cycle (postremission)-<br>Cytarabine 2000 mg/m² IV over 1 hour every 12 hours days 1-4<br>Daunorubicin 45 mg/m² IV days 1, 2<br>Maintenance therapy-randomized<br>ATRA 45 mg/m²/d PO in divided doses every 12 hours for 1 year or to observation | | Induction Therapy<br>Severe = S<br>Life-Threatening = LT<br>Lethal = L<br>Infection<br>S = 38%, LT = 8%, L = 6%<br>Hepatic S = 13%, LT = 9%<br>Hemorrhage<br>S = 6%, LT = 4%, L = 7%<br>Pulmonary<br>S = 2%, LT = 2%, L = 1%<br>Stomatitis S = 5%, LT = 1%<br>Cardiac S = 9%<br>Nausea S = 9%<br>Diarrhea S = 10%, LT = 1%<br>Dermatologic S = 5%, LT = 1%<br>Neurologic S = 7%, LT = 1% |

| Drug Dose and Target | Leukopenia/ Neutropenia Toxicity | Other Grade III-IV Toxicities |
|---|---|---|
| | | Maintenance Therapy (n = 94) Infection 7.4% Life-Threatening Toxicity 36% Neurotoxicity 11.7% Hepatotoxicity 5.3% |
| LEUKEMIAS: CHRONIC LYMPHOCYTIC | | |
| Alemtuzumab 30 mg IV over 2 hours three times a week (initiate dosing at 3 mg IV daily; when tolerated [infusion-related toxicities are <Grade 2] increase to 10 mg). When the 10 mg dose is tolerated, the maintenance dose of alemtuzumab 30 mg can be initiated. Maintain at 30 mg TIW for up to 12 weeks. | Neutropenia Grade III-IV 64% | Sepsis 10% Fever 19% Thrombocytopenia 50% Fatigue 5% Rigors 16% Hypotension 5% Bronchitis/Pneumonitis 13% Pneumonia 10% Urticaria 5% Dyspnea 9% Anemia Grade III-IV 38% |
| Chlorambucil 30 mg/m² PO day 1 Prednisone 80 mg/d PO days 1-5 Repeat cycle every 14 days Cladribine 0.12 mg/kg/d IV over 2 hours days 1-5 Prednisone 30 mg/m²/d PO days 1-5 Repeat cycle every 28 days | Hematologic Grade III-IV 25% Granulocytopenia 9% | Neutropenic Infection 7% Neutropenic Fever 2% Vomiting 3% FUO/Infection* 56% Thrombocytopenia 9% Autoimmune Hemolytic Anemia* 6% Hepatic* 6% Nausea/Vomitng* 2% Diarrhea* 2% Anemia Grade III-IV 2% *Grade Unknown |
| Fludarabine 25-30 mg/m²/d IV days 1-5 Repeat cycle every 28 days | Neutropenia 56% Grade IV (of cycles) | Febrile Infection During Cycles 1-3 30% Thrombocytopenia 25% Nausea 3% Stomatitis 2% Diarrhea 2% Neuropathy 4% |
| LEUKEMIAS: CHRONIC MYELOGENOUS | | |
| Interferon 5 MU/m² SQ daily Cytarabine 20 mg/m²/d SQ days 1-10 every month Notes: Decrease dose by 50% for granulocyte count <1500/mm³ and/or platelets <100,000/mm³ Cytarabine held for WBC <3000/mm³ and platelets <100,000/mm³; cytarabine discontinued for granulocyte count <1000/mm³ and platelets <50,000/mm³ If hematologic control not achieved, then increase cytarabine to 40 mg/m²/d SQ days 1-15. | | Nausea/Vomiting/ Diarrhea 12.5% Mucositis 5.8% Other GI 1% Weight Loss/ Asthenia 13.3% Skin Rash 5.2% Fever, Flu-like Syndrome 3% Peripheral Neuropathy 1% Central Neurologic Symptoms 1% Depression 4.2% Other Psychologic 3.6% Cytolytic Hepatitis 2.5% Other Toxicity 8.6% Thrombocytopenia 5.5% |
| LEUKEMIAS: HAIRY CELL | | |
| Cladribine 0.1 mg/kg/d IV continuous infusion days 1-7 Administer one cycle | Grade III-IV 87% | Neutropenic Fever 42% Documented Infections 13% Thrombocytopenia 20% Anemia Grade III-IV 22% |

-continued

| Drug Dose and Target | Leukopenia/ Neutropenia Toxicity | Other Grade III-IV Toxicities |
|---|---|---|
| Carboplatin AUC of 6 given IV day 1<br>Paclitaxel 225 mg/m$^2$ IV over 3 hours day 1<br>Repeat cycle every 21 days. | Leukopenia<br>Grade III 26%<br>Grade IV 5%<br>Neutropenia<br>Grade III 21%<br>Grade IV 36% | Thrombocytopenia<br>(Grade III) 10%<br>Nausea (Grade III) 7%<br>Neuropathy (Grade III)<br>13%<br>Vomiting (Grade III) 4%<br>Dehydration (Grade III)<br>4%<br>Fatigue (Grade III) 8%<br>Anemia Grade III-IV<br>13% |
| Paclitaxel 215 mg/m$^2$ IV over 24 hours,<br>day 1, followed by<br>Carboplatin dose targeted by<br>Calvert equation to AUC of 7.5 IV<br>Repeat cycle every 21 days. | Grade III 26%<br>Grade IV 45%<br>(G-CSF use<br>after cycle 2) | Febrile Neutropenia 13%<br>Hospitalization (for<br>IV antibiotics) 13%<br>Nausea/Vomiting 8%<br>Thrombocytopenia 48%<br>Fatigue 21%<br>Anorexia 23%<br>Myalgia/Arthralgia 6%<br>Paresthesia 2%<br>Anemia Grade III-IV<br>34% |
| Cisplatin 100 mg/m$^2$ IV day 1<br>Vinorelbine 30 mg/m$^2$ IV days 1, 8, 15, 22<br>Repeat cycle every 28 days | Leukopenia<br>Grade III 35%<br>Grade IV 15%<br>Neutropenia<br>Grade III 27%<br>Grade IV 49% | Thrombocytopenia<br>(Grade III) 4%<br>Nausea (Grade III) 18%<br>Neuropathy (Grade III)<br>3%<br>Vomiting (Grade III)<br>12%<br>Dehydration (Grade III)<br>6%<br>Fatigue (Grade III) 11%<br>Hyponatremia (Grade III)<br>7%<br>Respiratory Infection<br>(with neutropenia) (Grade<br>III) 5%<br>anemia Grade III 17% |
| Docetaxel 36 mg/m$^2$ IV<br>over 1 hour days 1, 8, 15, 22, 29, 36<br>Repeat cycle every 8 weeks | Leukopenia<br>Grade III 8% | Fatigue/Asthenia 10%<br>Nausea/Emesis 10%<br>Skin Toxicity 3%<br>Neuropathy 3%<br>Hypersensitivity<br>Reactions 3%<br>Alopecia 13%<br>Anemia Grade III 13% |
| Docetaxel 75 mg/m$^2$ IV day 1<br>Cisplatin 100 mg/m$^2$ IV day 1<br>Repeat cycle every 21 days. | Grade III-IV 67% | Hospitalized for Febrile<br>Neutropenia 16%<br>Neutropenic Infection<br>14%<br>Thrombocytopenia 2%<br>Allergy 2%<br>Cardiac Dysrhythmia 4%<br>Diarrhea 6%<br>Nausea 14%<br>Vomiting 14%<br>Alopecia* 12%<br>Asthenia 35%<br>Nail Disorder 4%<br>Neuromotor 2%<br>Neurosensory 2%<br>Anemia Grade III-IV<br>10%<br>*Grade II toxicity |
| Etoposide 100 mg/m$^2$/d IV days 1-3<br>Cisplatin 120 mg/m$^2$ IV day 1<br>Repeat cycle every 21-28 days | Leukopenia<br>Grade III-IV 34% | Neutropenic Infection*<br>5%<br>Thrombocytopenia* 15%<br>Nausea/Vomiting* 77%<br>Diarrhea* 11%<br>Bleeding* 3%<br>Polyneuropathy 2%<br>Renal Dysfunction* 10%<br>Hypoacusia* 7%<br>Alopecia* 60%<br>*Grade II-IV toxicity |

| Drug Dose and Target | Leukopenia/ Neutropenia Toxicity | Other Grade III-IV Toxicities |
| --- | --- | --- |
| Gemcitabine 1200 mg/m$^2$ IV days 1, 8<br>Vinorelbine 30 mg/m$^2$ IV days 1, 8<br>Repeat cycle every 21 days | Neutropenia<br>Grade III 30%<br>Grade IV 8.3% | Thrombocytopenia 13.3%<br>Vomiting 15%<br>Fatigue (Grade III) 5%<br>Anemia Grade III 6.7% |
| Gemcitabine 1000 mg/m$^2$ IV over<br>30-60 minutes days 1, 8, 15, followed by<br>Cisplatin 100 mg/m$^2$ IV over<br>30-120 minutes day 1 only<br>Repeat cycle every 28 days | Granulocytopenia<br>Grade III 21.7%<br>Grade IV 35.3% | Neutropenic Fever 4.6%<br>Thrombocytopenia 50.4%<br>Nausea 27%<br>Vomiting 23%<br>Neurohearing 6%<br>Neuromotor (Grade III) 11.5%<br>Cardiac Dysrrhythmia 2.8%<br>Dyspnea 7%<br>Elevated Creatinine 4.8%<br>Anemia Grade III-IV 25% |
| Paclitaxel 200 mg/m$^2$ IV over 3 hours day 1<br>Repeat cycle every 21 days | Leukopenia<br>Grade III-IV 9%<br>Neutropenia<br>Grade III-IV 34% | Infection 10%<br>Nausea/Vomiting 5%<br>Diarrhea 4%<br>Mucositis 1%<br>Arthralgia/Myalgia 22%<br>Asthenia 14%<br>Peripheral Neuropathy 5%<br>Alopecia 76%<br>Cardiovascular 1%<br>Anemia Grade III-IV 3% |
| Vinorelbine 30 mg/m$^2$ IV weekly | Grade III-IV 79% | Neutropenic Sepsis 3%<br>Nausea/Vomiting (Grade II-IV) 12%<br>Neurologic 9%<br>Diarrhea (Grade II-IV) 4%<br>Alopecia (Grade II-IV) 14% |
| Vinorelbine 30 mg/m$^2$ IV weekly<br>Cisplatin 120 mg/m$^2$ IV days 1 and 29, then every 6 weeks | Grade III-IV 78.7% | Neutropenic Sepsis 4%<br>Nausea/Vomiting (Grade II-IV) 58%<br>Thrombocytopenia 3%<br>Neurologic 7%<br>Ototoxicity 2%<br>Diarrhea (Grade II-IV) 11%<br>Renal (creatinine > 250 umol/L) 6% |
| LUNG CANCER: SMALL-CELL | | |
| Cyclophosphamide 1000 mg/m$^2$ IV day 1<br>Doxorubicin 45 mg/m$^2$ IV day 1<br>Etoposide 100 mg/m$^2$ IV days 1, 3, 5<br>Repeat cycle every 21 days | Leukopenia<br>Grade III 33%<br>Grade IV 46% | Neutropenic Infection<br>(Grade III) 9%<br>(Grade IV) 3%<br>(Grade V) 2%<br>Overall Infection Rate 40%<br>Thrombocytopenia 23%<br>Nausea/Vomiting 33%<br>Mucositis 3%<br>Diarrhea 2%<br>Cardiac 2%<br>Alopecia 57% |
| Cyclophosphamide 800 mg/m$^2$ IV day 1<br>Doxorubicin 50 mg/m$^2$ IV day 1<br>Vincristine 1.4 mg/m$^2$ IV day 1<br>Repeat cycle every 21-28 days | Leukopenia<br>Grade III-IV 79% | Nausea/Vomiting (Grade II-IV) 64%<br>Thrombocytopenia 13%<br>Neuropathy (Grade II-IV) 9%<br>Hepatic (Grade II-IV) 11%<br>Renal (Grade II-IV) 4%<br>Alopecia (Grade II-IV) 72% |

| Drug Dose and Target | Leukopenia/ Neutropenia Toxicity | Other Grade III-IV Toxicities |
|---|---|---|
| Etoposide 100 mg/m$^2$/d IV days 1-3<br>Carboplatin 300 mg/m$^2$ IV day 1<br>Repeat cycle every 21 days | Leukopenia<br>Grade III 10%<br>Grade IV 7% | Neutropenic Infection (all grades) 11%<br>Thrombocytopenia (Grade IV) 4%<br>Alopecia (Grade III) 7% |
| Etoposide 100 mg/m$^2$/d IV days 1-3<br>Cisplatin 100 mg/m$^2$ IV day 2<br>Repeat cycle every 28 days | Neutropenia<br>Grade III-IV<br>85% | Documented Infections (all grades) 8%<br>Fever (all grades) 18%<br>Nausea/Vomiting 19%<br>Thrombocytopenia 18%<br>Creatinine Increase 12%<br>Bilirubin Increase 2%<br>Anemia Grade III-IV 18% |
| Etoposide 100 mg/m$^2$/d IV days 1-3<br>Cisplatin 100 mg/m$^2$ IV day 2<br>Cyclophosphamide 400 mg/m$^2$/d IV days 1-3<br>Epirubicin 40 mg/m$^2$ IV day 1<br>Repeat cycle every 28 days | Neutropenia<br>Grade III-IV<br>99% | Documented Infections (all grades) 22%<br>Fever (all grades) 70%<br>Nausea/Vomiting 22%<br>Thrombocytopenia 78%<br>Creatinine Increase 6%<br>Bilirubin Increase 1%<br>Anemia Grade III-IV 51% |
| Topotecan 1.5 mg/m$^2$/d IV over 30 minutes, days 1-5<br>Repeat cycle every 21 days | Grade III-IV 89% | Neutropenic Fever 28%<br>Neutropenic Sepsis 5%<br>Thrombocytopenia 58%<br>Nausea 4%<br>Fatigue 5%<br>Vomiting 2%<br>Stomatitis 2%<br>Anorexia 1%<br>Diarrhea 1%<br>Anemia Grade III-IV 42% |
| Topotecan 1.0 mg/m$^2$/d IV days 1-5<br>Paclitaxel 135 mg/m$^2$ IV over 24 hr day 5<br>Repeat cycle every 28 days | Grade IV 96%<br>Primary prophylaxis with G-CSF | Neutropenic Fever (of cycles) 21%<br>Thrombocytopenia (Grade IV) 18%<br>Allergic Reaction* 7%<br>Cardiac Dysrhythmia* 4%<br>*Grade not specified |
| LYMPHOMA: HODGKIN'S DISEASE | | |
| Doxorubicin 25 mg/m$^2$ IV days 1, 15<br>Bleomycin 10 units/m$^2$ IV days 1, 15<br>Vinblastine 6 mg/m$^2$ IV days 1, 15<br>Dacarbazine 350-375 mg/m$^2$ IV days 1, 15<br>Repeat cycle every 28 days | Grade III-IV 21% | Neutropenic Infection 2%<br>Thrombocytopenia (Grade IV) 5%<br>Alopecia 24%<br>Pulmonary Toxicity 7%<br>Neuropathy 1%<br>Nausea/Vomiting 33%<br>Anemia Grade III-IV 5% |
| Chlorambucil 6 mg/m$^2$/d PO days 1-14, max 10 mg/day<br>Vinblastine 6 mg/m$^2$ IV days 1, 8, max 10 mg/day<br>Procarbazine 100 mg/m$^2$/d PO days 1-14, max 150 mg/day<br>Prednisolone 40 mg/d PO days 1-14<br>Repeat cycle every 28 days | Leukopenia<br>Grade III 7%<br>Grade IV 2% | Neutropenic Infection 3%<br>Thrombocytopenia 5%<br>Nausea/Vomiting 2%<br>Alopecia <1% |
| Mechlorethamine 6 mg/m$^2$ IV days 1, 8<br>Vincristine 1.4 mg/m$^2$ IV days 1, 8 (maximum 2 mg)<br>Procarbazine 100 mg/m$^2$/d PO days 1-14<br>Prednisone 40 mg/m$^2$/d PO days 1-14<br>Repeat cycle every 28 days | Grade III-IV 68% | Neutropenic Infection (Sepsis) Grade IV 12%<br>Thrombocytopenia 52%<br>Nausea/Vomiting 28%<br>Peripheral Neuropathy 8%<br>Alopecia 5%<br>Pulmonary Toxicity 4%<br>Anemia Grade III-IV 43% |

-continued

| Drug Dose and Target | Leukopenia/ Neutropenia Toxicity | Other Grade III-IV Toxicities |
|---|---|---|
| Mechlorethamine 6 mg/m² IV day 1<br>Doxorubicin 25 mg/m² IV days 1, 15<br>Vinblastine* 6 mg/m² IV days 1, 15<br>Vincristine* 1.4 mg/m² IV days 8, 22<br>Bleomycin 5 units/m² IV days 8, 22<br>Etoposide 60 mg/m² IV days 15, 16<br>Prednisone 40 mg/m² PO QOD, dose tapered over the last 15 days<br>Repeat cycle every 28 days<br>*In patients >50 years of age, vinblastine dose decreased to 4 mg/m², and vincristine dose decreased to 1 mg/m² on weeks 9-12.<br>Concomitant trimethoprim/sulfamethoxazole DS PO bid; acyclovir 200 mg PO tid, ketoconazole 200 mg PO qd and stool softeners used | Grade III 37%<br>Grade IV 45% | Neutropenic Fever 17%<br>Constipation/Ileus* 11%<br>Deep Vein<br>Thrombosis* 3%<br>Neurologic:<br>Motor 8%<br>Sensory 11%<br>Autonomic 12%<br>Phlebitis 38%<br>Nausea/Vomiting 9%<br>Anemia Grade III-IV 26%<br>*Required hospitalization |
| LYMPHOMA: NON-HODGKIN'S | | |
| Cyclophosphamide 750 mg/m² IV day 1<br>Doxorubicin 50 mg/m² IV day 1<br>Vincristine 1.4 mg/m² IV day 1 (maximum 2 mg)<br>Prednisone 100 mg/d PO days 1-5<br>Repeat cycle every 21 days | Grade IV 91%<br>(Note: combined data w/CNOP) | |
| Rituximab 375 mg/m² IV day 1 of each cycle followed by<br>Cyclophosphamide 750 mg/m² IV day 3 of cycle<br>Doxorubicin 50 mg/m² IV day 3 of cycle<br>Vincristine 1.4 mg/m² (max 2 mg) IV day 3 of cycle<br>Prednisone 100 mg/d PO on days 3-7 of cycle<br>Repeat cycle every 21 days<br>Premedicate with acetaminophen and diphenhydramine prior to rituximab | Neutropenia<br>Grade III 15.1%<br>Grade IV 57.6%<br>Leukopenia<br>Grade III 9.1%<br>Grade IV 12.1% | Sepsis 9.1%<br>Fever 9.1%<br>Thrombocytopenia (Grade III) 3%<br>Bowel Obstruction (Grade III) 3%<br>Intestinal Perforation (Grade IV) 3%<br>Infusion-Related Reaction (Grade IV) 3%<br>Anemia Grade III 12.1% |
| Cyclophosphamide 750 mg/m² IV day 1<br>Mitoxantrone 10 mg/m² IV day 1<br>Vincristine 1.4 mg/m² IV day 1 (maximum 2 mg)<br>Prednisone 50 mg/m²/d PO days 1-5<br>Repeat cycle every 21 days | Grade III-IV*<br>>50%<br>*Mean ANC 600/mm³ | Stomatitis 3%<br>Nausea/Vomiting 16%<br>Alopecia 24%<br>Cardiac 2%<br>Neurologic 7%<br>Diarrhea 2%<br>Cutaneous 2 |
| Cyclophosphamide 800 mg/m² IV day 1, then 200 mg/m²/d IV days 2-5<br>Vincristine 1.5 mg/m² IV days 1, 8 in cycle 1 and on days 1, 8, and 15 on cycle 3<br>Doxorubicin 40 mg/m² IV day 1<br>Cytarabine intrathecal 70 mg days 1, 3<br>Methotrexate 1200 mg/m² IV over 1 hour, followed by 240 mg/m²/hour for the next 23 hours starting on day 10<br>Calcium leucovorin 192 mg/m² IV to start 12 hours after the completion of the methotrexate infusion × 1 dose, then 12 mg/m² IV every 6 hours until the methotrexate level is <5 × 10−8 mol/L<br>GM-CSF 7.5 mcg/kg/d subcutaneously day 13 onwards until ANC > 1000.<br>Methotrexate 12 mg intrathecal (IT) day 15 | Neutropenia<br>Grade IV<br>97.6% cycles (<18 years)<br>Grade IV (≥18 years)<br>97.8%<br>Leukopenia<br>Grade IV<br>97.6% cycles (<18 years)<br>Grade IV<br>95.6% cycles (≥18 years) | Thrombocytopenia (Grade III)<br>17.1% (<18 years) and 9.3% (≥18 years)<br>Thrombocytopenia (Grade IV)<br>53.7% (<18 years) and 39.5% (≥18 years)<br>Stomatitis (Grade III)<br>26.8% (<18 years) and 28.9% (≥18 years)<br>Stomatitis (Grade IV)<br>41.5% (<18 years) and 20% (≥18 years)<br>Hepatotoxicity (Grade III)<br>24.4% (all ages)<br>Hepatotoxicity (Grade IV)<br>2.4% (all ages) |
| Denileukin diftitox 9 or 18 mcg/kg/d IV days 1-5<br>Repeat cycle every 21 days<br>Premedicate with acetaminophen and antihistamines<br>Premedication with corticosteroids not permitted | 9 mcg/kg:<br>Leukopenia 6%<br>Neutropenia 3%<br>18 mcg/kg:<br>Leukopenia 3%<br>Neutropenia 3% | Infection 33-43%<br>Infusion-Related Events<br>Back Pain 6-11%<br>Chest Pain/ Tightness 9%<br>Pruritis 6%<br>Hypotension 8-11%<br>Vasodilation 3%<br>Dyspnea 6-11%<br>Constitutional Symptoms 37-47%<br>Gastrointestinal 20-36% |

| Drug Dose and Target | Leukopenia/ Neutropenia Toxicity | Other Grade III-IV Toxicities |
|---|---|---|
| | | Vascular Leak Syndrome 17-25% Thrombotic Events 3-8% Rash 19-23% Right Heart Failure 3-6% CNS 17-25% |
| Dexamethasone 40 mg/d PO or IV days 1-4 Cisplatin 100 mg/m²/d IV continuous infusion day 1 Cytarabine 2000 mg/m² IV every 12 hours for 2 doses, day 2 Repeat cycle every 21 to 28 days | Grade IV 53% | Neutropenic Sepsis 31% Infection* 31% Thrombocytopenia* 39% Renal** 20% Gastrointestinal† 20% Neurological†† 6% Respiratory†† 6% Tumor Lysis Syndrome 5% *Grade IV toxicity **SCr > double baseline value †Severe ††Unknown grade of toxicity |
| Etoposide 40 mg/m²/d IV days 1-4 Methylprednisolone 250-500 mg/d IV days 1-5 Cisplatin 25 mg/m²/d IV continuous infusion days 1-4 Cytarabine 2000 mg/m² IV day 5 Give immediately following completion of etoposide and cisplatin Repeat cycle every 21-28 days | Grade IV 50% | Febrile Neutropenia 30% Thrombocytopenia (plt <70,000/mm³) 50% Nausea/Vomiting 6% Renal (SCr > double baseline) 22% |
| Etoposide 100 mg/m²/d IV days 1-3 Carboplatin AUC of 5 (maximum dose 800 mg) IV day 2 Ifosfamide 5 g/m² IV continuous infusion over 24 hours day 2 (with 100% replacement with mesna) G-CSF 5 mcg/kg/d SQ days 5-12 | Neutropenia 20.8% | Thrombocytopenia 29.4% Neurotoxicity (not graded) 3% Increased Alkaline Phosphatase (2×) 11% Increased Alanine Transferase (2×) 9.8% Anemia Grade III-IV 26.5% |
| Cyclophosphamide 1000 mg/m² IV day 1 Fludarabine 20 mg/m²/d IV over 30 minutes days 1-5 Repeat cycle every 28 days | Neutropenia (all cycles) Grade III 25% of cycles Grade IV 18% of cycles Neutropenia (first cycle, without growth factor) Grade III 26% Grade IV 28% | Infectious toxicity 11% Pulmonary toxicity 18% |
| Fludarabine 25 mg/m²/d IV days 1-3 Idarubicin 12 mg/m² IV day 1 Repeat cycle every 28 days | Hematologic toxicity Grade III-IV 3.7% | Nausea 72.5% |
| Fludarabine 20 mg/m²/d IV days 1-5 Cyclophosphamide 600 mg/m² IV day 1 G-CSF 5 mcg/kg SQ starting day 8 continuing 10-14 days until ANC ≥ 10,000 Trimethoprim/Sulfamethoxazole PO twice daily every Monday, Wednesday, Friday Allopurinol 300 mg daily days 1-7, cycle 1 only Repeat cycle every 28 days | Neutropenia Grade III 20% Grade IV 8% | Thrombocytopenia (Grade III) 1.6% Pulmonary (Grade III) 3.3% Anemia Grade III-IV 7% |
| Fludarabine 25 mg/m²/d IV days 1-3 Mitoxantrone 10 mg/m² IV day 1 Dexamethasone 20 mg/d PO days 1-5 Repeat cycle every 28 days | Neutropenia Grade IV 20% | Febrile Neutropenia 3.8% Thrombocytopenia: Platelets <50,000 8% Platelets <100,000 31% |
| Etoposide 60 mg/m²/d IV over 1 hour days 1-5 Ifosfamide 1500 mg/m²/d IV over 1 hour days 1-5 | Neutropenia Grade IV 100% (all ages) Leukopenia | Thrombocytopenia (Grade III): 14.3% cycles (<18 years) |

| Drug Dose and Target | Leukopenia/ Neutropenia Toxicity | Other Grade III-IV Toxicities |
|---|---|---|
| Mesna 360 mg/m² IV over 1 hour (1 dose mixed with ifosfamide), followed by mesna 360 mg/m² IV over 15 minutes every 3 hours days 1-5<br>Cytarabine 2000 mg/m² IV over 3 hours every 12 hours on days 1, 2 (a total of 4 doses)<br>Methotrexate intrathecal 12 mg × 1 on day 5<br>GM-CSF 7.5 mcg/kg/d SQ day 7 onwards | Grade IV 100% (all ages) | 3.7% (≥18 years) Thrombocytopenia (Grade IV) 82.9% cycles (<18 years) 96.3% (≥18 years) Hepatotoxicity (Grade III) 5.9% cycles (<18 years) Stomatitis (Grade III) 5.7% cycles (<18 years) 3.4% cycles (≥18 years) Stomatitis (Grade IV) 2.9% cycles (<18 years) |
| Methotrexate 400 mg/m² IV weeks 2, 6, 10 with leucovorin rescue<br>Doxorubicin 50 mg/m² IV weeks 1, 3, 5, 7, 9, 11<br>Cyclophosphamide 350 mg/m² IV weeks 1, 3, 5, 7, 9, 11<br>Vincristine 1.4 mg/m² IV weeks 2, 4, 6, 8, 10, 12 (maximum of 2 mg)<br>Prednisone 75 mg/d PO for 12 weeks then taper over last 2 weeks<br>Bleomycin 10 units/m² IV weeks 4, 8, 12<br>Trimethoprim/sulfamethoxazole DS tablet PO bid for 12 weeks<br>Ketoconazole 200 mg/d PO<br>Administer one cycle | Grade IV 21% | Neutropenic Infection Major Infection 11% Minor Infection 11% Thrombocytopenia* 2% Mucositis† 26% Neurologic† 8% Cutaneous† 3% Endocrinologic 5% *Grade IV Toxicity †Severe or Major Anemia Grade III-IV 20% Requiring transfusion |
| Methotrexate 200 mg/m² IV days 8, 15<br>Leucovorin 10 mg/m² PO q6h for 6 doses, beginning 24 hours after each methotrexate dose<br>Bleomycin 4 units/m² IV day 1<br>Doxorubicin 45 mg/m² IV day 1<br>Cyclophosphamide 600 mg/m² IV day 1<br>Vincristine 1 mg/m² IV day 1 (maximum 2 mg)<br>Dexamethasone 6 mg/m²/d PO days 1-5<br>Repeat cycle every 21 days | Leukopenia Grade III 34% Grade IV 50% | Neutropenic Infection* 40% Neutropenia Grade III 25% Grade IV 10% Thrombocytopenia 13% Vomiting 11% Stomatitis 37% Neurologic 11% Pulmonary* 11% Diarrhea 2% Skin 1% Cardiac 3% Hepatic 1% Anemia Grade III-IV 42% *Grade III-V toxicity |
| Mesna 1330 mg/m²/d IV administered at same time as ifosfamide, then 500 mg PO, 4 hours after ifosfamide, days 1-3<br>Ifosfamide 1330 mg/m²/d IV over 1 hour, days 1-3<br>Mitoxantrone 8 mg/m² IV day 1<br>Etoposide 65 mg/m²/d IV days 1-3<br>Repeat cycle every 21 days for 6 cycles, followed by 3 to 6 cycles of ESHAP | | Neutropenic Fever 42% of patients, 7% of cycles Documented Infection 17% of patients, 3% of cycles Neutrophils* 1.1K Platelets* 133K Hemoglobin* 9.7 g/dl Nausea/Vomiting 11% Diarrhea 3% Stomatitis 1% Hearing Loss 2% Cardiovascular 2% *Mean nadir levels |
| Prednisone 60 mg/m²/d PO day 1-14<br>Doxorubicin 25 mg/m² IV day 1<br>Cyclophosphamide 650 mg/m² IV day 1<br>Etoposide 120 mg/m² IV day 1<br>Cytarabine 300 mg/m² IV day 8<br>Bleomycin 5 units/m² IV day 8<br>Vincristine 1.4 mg/m² IV day 8<br>Methotrexate 120 mg/m² IV day 8<br>Leucovorin 25 mg/m² PO q6h for 4 doses beginning 24 hours after methotrexate<br>Trimethoprim/sulfamethoxazole DS PO bid<br>Repeat cycle every 21 to 28 days | Grade III-IV 20% | Febrile Neutropenia 20% Documented Infection 13% Thrombocytopenia 7% Tumor Lysis 16% Coagulopathy* 12% GI Bleeding* 5% Anemia Grade III-IV 61% Requiring transfusion *Requiring hospitalization |

-continued

| Drug Dose and Target | Leukopenia/ Neutropenia Toxicity | Other Grade III-IV Toxicities |
|---|---|---|
| MELANOMA | | |
| Cisplatin 20 mg/m$^2$/d IV days 2-5<br>Vinblastine 1.6 mg/m$^2$/d IV days 1-5<br>Dacarbazine 800 mg/m$^2$ IV day 1<br>Repeat cycle every 21 days | Grade IV 50% | Neutropenic Fever 30%<br>Thrombocytopenia 26%<br>Alopecia* 100%<br>Nausea/Vomiting* 86%<br>Renal* 12%<br>Diarrhea* 34%<br>Hypomagnesemia** 68%<br>Neuropathy† 20%<br>*Unknown grade<br>**Requiring replacement<br>†Moderately severe |
| Dacarbazine 1000 mg/m$^2$ IV day 1<br>Repeat cycle every 21 days | Neutropenia<br>Grade III 10%<br>Grade IV 9%<br>Leukopenia without neutropenia<br>Grade III 1% | Thrombocytopenia 7%<br>Nausea/Vomiting 5%<br>Dyspnea 1%<br>Anemia Grade III-IV 6% |
| Dacarbazine 250 mg/m$^2$/d IV<br>over 30 minutes days 1-5<br>Repeat cycle every 21 days | Neutropenia<br>Grade III 1%<br>Grade IV 1% | Fever (Grade III) 2%<br>Thrombocytopenia 8%<br>Asthenia (Grade III) 1%<br>Fatigue (Grade III) 2%<br>Headache (Grade III) 1%<br>Pain (Grade III) 13%<br>Constipation (Grade III) 3%<br>Nausea (Grade III) 4%<br>Vomiting (Grade III) 4%<br>Somnolence (Grade III) 1%<br>Anemia Grade IV 1% |
| Dacarbazine 220 mg/m$^2$/d IV days 1-3, every 22-24 days<br>Carmustine 150 mg/m$^2$ IV day 1<br>Cisplatin 25 mg/m$^2$/d IV days 1-3, every 22-24 days<br>Tamoxifen 160 mg/d PO 7 days before chemotherapy, then 40 mg/d days 1-42<br>Repeat every 43 days | Grade IV 31%-32% | Neutropenic Fever 11%<br>Systemic Infection (requiring IV antibiotics) 4% or 3%<br>Deep Vein Thrombosis 4%<br>Hot Flashes 3%<br>Thrombocytopenia* 44%<br>Vomiting† 40%<br>*Grade IV toxicity<br>†Unknown toxicity grade |
| Tamoxifen 10 mg PO twice daily (start 1 week prior to chemotherapy and continue indefinitely)<br>Carmustine (BCNU) 150 mg/m$^2$ IV day 1 (repeat every 42 days-every other cycle)<br>Cisplatin 25 mg/m$^2$/d IV days 1-3<br>Dacarbazine 220 mg/m$^2$/d IV days 1-3<br>Repeat cisplatin and dacarbazine every 21 days | Neutropenia<br>Grade III 24%<br>Grade IV 15%<br>Leukopenia without neutropenia<br>Grade III 8%<br>Grade IV 1% | Thrombocytopenia 57%<br>Nausea/Vomiting 18%<br>Fatigue 7%<br>Increased Serum Creatinine 3%<br>Dyspnea 5%<br>Anemia Grade III-IV 32% |
| Dacarbazine 800 mg/m$^2$ IV day 1<br>Cisplatin 20 mg/m$^2$/d IV days 1-4<br>Vinblastine 1.2 mg/m$^2$/d IV days 1-4<br>Interferon-alfa 2b 5 MU/m$^2$/d SQ days 1-5, 8, 10, 12<br>Aldesleukin 9 MU/m$^2$/d IV continuous infusion days 1-4<br>Filgrastim 5 mcg/kg/d SQ days 7-16<br>Repeat cycle every 21 days for a maximum of 4 cycles | Neutropenia<br>Grade IV 30% | Neutropenic Fever 9%<br>Infection 7%<br>Thrombocytopenia 43%<br>Hypotension 30%<br>Nausea/Vomiting 27%<br>Renal Insufficiency 11%<br>Neurologic Toxicity 5%<br>Bleeding 2% |
| Temozolomide 200 mg/m$^2$/d PO days 1-5<br>Repeat cycle every 28 days | Neutropenia<br>Grade III 1%<br>Grade IV 2% | Fever 2%<br>Thrombocytopenia 7%<br>Asthenia (Grade III) 3%<br>Fatigue (Grade III) 3%<br>Headache 6%<br>Pain (Grade III) 7%<br>Constipation (Grade III) 3%<br>Nausea (Grade III) 4%<br>Vomiting 5%<br>Anemia Grade III-IV 2% |

| Drug Dose and Target | Leukopenia/ Neutropenia Toxicity | Other Grade III-IV Toxicities |
|---|---|---|
| MULTIPLE MYELOMA | | |
| Vincristine 0.03 mg/kg IV day 1<br>Carmustine 0.5-1 mg/kg IV day 1<br>Cyclophosphamide 10 mg/kg IV day 1<br>Melphalan 0.25 mg/kg/d PO days 1-4 or<br>0.1 mg/kg/d PO days 1-7 or 1-10<br>Prednisone 1 mg/kg/d PO days 1-7<br>Repeat cycle every 35-42 days | Leukopenia<br>Grade IV 16% | Parethesias and<br>peripheral neuropathy<br>occurred frequently<br>Nausea occurred<br>occasionally |
| Melphalan 8 mg/m$^2$/d PO days 1-4<br>Prednisone 60 mg/m$^2$/d PO days 1-4<br>Repeat cycle every 28 days | Grade III 29%<br>Grade IV 8% | Neutropenic Infections<br>(Grade III-IV) 14%<br>Nausea/Vomiting* 10%<br>Neuropathy* 2%<br>Alopecia† 7%<br>Thrombocytopenia 23%<br>*Grade II-IV toxicity<br>†Grade I-IV toxicity |
| Thalidomide 200 mg PO daily at bedtime<br>(dose increase every 2 weeks for 6 weeks<br>up to a dose of 800 mg/day)<br>Vincristine 0.4 mg/d IV continuous infusion<br>days 1-4<br>Doxorubicin 9 mg/m$^2$/d IV continuous<br>infusion days 1-4<br>Dexamethasone 40 mg PO<br>qd 1-4, 9-12, 17-20<br>Repeat cycle every 28-35 days | | Thrombocytopenia 3.6%<br>Anemia Grade III-IV<br>3.6%<br>Neutropenic Sepsis 30%<br>Thrombocytopenia<br>(Grade II) 11%<br>Removal of Catheter<br>Due to Thrombis<br>or Infection 14%<br>Cushingoid Features 26%<br>Irritability 19%<br>Aggravation of<br>Diabetes 11% |
| Vincristine 1.2 mg/m$^2$ IV<br>day 1 (maximum 2 mg)<br>Carmustine 20 mg/m$^2$ IV day 1<br>Melphalan 8 mg/m$^2$/d PO days 1-4<br>Cyclophosphamide 400 mg/m$^2$ IV day 1<br>Prednisone 40 mg/m$^2$/d PO<br>days 1-7 of all cycles<br>20 mg/m$^2$/d PO days 8-14<br>first three cycles only<br>Repeat cycle every 35 days | Grade III 30%<br>Grade IV 16% | Neutropenia<br>(Grade IV) 14%<br>Nausea/Vomiting* 31%<br>Neuropathy* 24%<br>Alopecia† 25%<br>Thrombocytopenia 23%<br>*Grade II-IV toxicity<br>†Grade I-IV toxicity |
| SARCOMA: UNCLASSIFIED | | |
| Doxorubicin 22.5 mg/m$^2$/d IV continuous<br>infusion days 1-4<br>Dacarbazine 225 mg/m$^2$/d IV continuous<br>infusion days 1-4<br>Repeat cycle every 21 days | Grade III-IV 38% | Nausea/Vomiting 9%<br>Thrombocytopenia 4%<br>Cardiac 1%<br>Pulmonary Embolism 1%<br>Mucositis/Stomatitis 7%<br>Anemia Grade III-IV 6% |
| Doxorubicin 50 mg/m$^2$ IV bolus, day 1<br>Ifosfamide 5000 mg/m$^2$/d IV continuous<br>infusion following doxorubicin, day 1<br>Mesna 600 mg/m$^2$ IV bolus before<br>ifosfamide, 2500 mg/m$^2$/d IV continuous<br>infusion with ifosfamide 1250 mg/m$^2$ IV<br>over 12 hr following ifosfamide<br>Repeat cycle every 21 days | Leukopenia<br>Grade III-IV<br>73%<br>Grade IV 34% | Neutropenic Fever 2%<br>Documented Infection<br>6%<br>Fever 2%<br>Thrombocytopenia* 5%<br>Nausea/Vomiting 41%<br>Alopecia 71%<br>Diarrhea 2%<br>Oral 3%<br>Renal 2%<br>Cardiac 1%<br>Consciousness 3%<br>Hematuria 2%<br>*<75,000/mm$^3$ |
| Doxorubicin 75 mg/m$^2$ IV day 1<br>Repeat cycle every 21 days | Grade III-IV 51%<br>Grade IV 21% | Infection 3%<br>Nausea/Vomiting 13%<br>Thrombocytopenia 2%<br>Mucositis 6%<br>Cardiotoxicity 1% |
| Etoposide 100 mg/m$^2$/d IV days 1-3<br>Ifosfamide 2500 mg/m$^2$/d IV days 1-3<br>Mesna at 20% of ifosfamide dose<br>prior to and 4, 8, and 12 hours after<br>ifosfamide administration<br>Repeat cycle every 28 days | Leukopenia<br>Grade IV 38% | Neutropenic Fever<br>during Leukopenia 5%<br>Nausea/Vomiting<br>(all Grades) 70%<br>Thrombocytopenia 3%<br>Alopecia (significant)<br>85%<br>Renal 2% |

| Drug Dose and Target | Leukopenia/ Neutropenia Toxicity | Other Grade III-IV Toxicities |
|---|---|---|
| Mesna 2500 mg/m²/d IV continuous infusion days 1-4<br>Doxorubicin 15 mg/m²/d IV continuous infusion days 1-4<br>Ifosfamide 2500 mg/m²/d IV continuous infusion days 1-3<br>Dacarbazine 250 mg/m²/d IV continuous infusion days 1-4<br>Repeat cycle every 21 days | Grade III-IV 80% | Neutropenic Infection 1%<br>Thrombocytopenia 26%<br>Somnolence/Coma 1%<br>Nausea/Vomiting 9%<br>Mucositis/Stomatitis 7%<br>Gastrointestinal 4%<br>Anemia Grade III-IV 22% |
| SARCOMA: AIDS-RELATED KAPOSI'S SARCOMA | | |
| Liposomal daunorubicin 40 mg/m² IV over 30-60 minutes every 2 weeks | Leukopenia<br>Grade III 33%<br>Grade IV 5%<br>Neutropenia<br>Grade III 36%<br>Grade IV 15% | Fever 5%<br>Thrombocytopenia 1%<br>Fatigue 6%<br>Diarrhea 4%<br>Nausea/Vomiting 5%<br>Abdominal Pain 3%<br>Dyspnea 3%<br>Allergic Reactions 3%<br>Anemia Grade III-IV 11% |
| Liposomal doxorubicin 20 mg/m² IV over 30 minutes every 2 weeks | Leukopenia 36%<br>Neutropenia<br>Grade IV 6% | Thrombocytopenia 3%<br>Nausea/Vomiting 15%<br>Peripheral Neuropathy 6%<br>Mucositis 5%<br>Anemia Grade III-IV 9.8% |
| Paclitaxel 100 mg/m² IV over 3 hours every 2 weeks | Neutropenia<br>Grade III 25%<br>Grade IV 36% | Thrombocytopenia 6%<br>Increased AST 5%<br>Alopecia (Grade III) 9%<br>Fatigue 25%<br>Myalgia (Grade III) 16%<br>Nausea/Vomiting (Grade III) 13%<br>Diarrhea 16%<br>Neuropathy (Grade III) 2%<br>Mucositis (Grade III) 2%<br>Anemia Grade III-IV 27% |
| UNKNOWN PRIMARY: ADENOCARCINOMA | | |
| 5-Fluorouracil 600 mg/m² IV days 1, 8, 29, 36<br>Doxorubicin 30 mg/m² IV days 1, 29<br>Mitomycin 10 mg/m² IV day 1<br>Repeat cycle every 8 weeks | Leukopenia<br>Grade III-IV 7% | Neutropenic Sepsis 5%<br>Thrombocytopenia 14%<br>Mucositis (Grade II-III) 7%<br>Cardiac 2% |
| Paclitaxel 200 mg/m² IV over 1 hour, day 1, followed by carboplatin dose targeted by Calvert equation to AUC of 6 IV day 1<br>Etoposide 50 mg/d PO alternated with 100 mg/d PO days 1-10<br>Repeat cycle every 21 days | Leukopenia<br>Grade III 56%<br>Grade IV 20% | Neutropenic Fever 13%<br>Nausea/Vomiting 9%<br>Thrombocytopenia 26%<br>Peripheral Neuropathy 7%<br>Hypersensitivity 2% |

In certain embodiments, patients are subjected to a hypoxia imaging technique prior to administration of the compositions comprising the compounds of the present invention. Examples of imaging techniques suitable, for the determination of the presence of hypoxic tumor cells include computed tomography (CT), magnetic resonance imaging (MRI), single photon emission computer tomography (SPECT), and positron emission tomography (PET). Use of such visualization methods can advantageously be used to select a subset of patients that are particularly suitable for treatment with hypoxia activated antiproliferative compositions of the present invention.

In this embodiment, the invention is directed to a method of treating, preventing or ameliorating a hyperproliferative disease in an animal in need thereof, comprising determining whether said hyperproliferative disease is characterized by hypoxic tissue, and treating said animal with an effective amount of a compound of the invention.

The term "radiotherapeutic agent," as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, surgery, and/or another radiotherapy.

In certain embodiments involving radiotherapeutic agents or treatments, the present invention relates to a method for treating cancer comprising the administration of vinca alkaloid or analog N-oxide having Formula I, in combination with a treatment comprising a therapeutically effective dose of brachytherapy. The brachytherapy can be administered according to any schedule, dose, or method known to one of skill in the art to be effective in the treatment or amelioration of cancer, without limitation. In general, brachytherapy comprises insertion of radioactive sources into the body of a subject to be treated for cancer, preferably inside the tumor itself, such that the tumor is maximally exposed to the radioactive source, while preferably minimizing the exposure of healthy tissue.

In certain embodiments, the brachytherapy can be intracavitary brachytherapy. In other embodiments, the brachytherapy can be interstitial brachytherapy. Whether the brachytherapy is intracavitary brachytherapy or interstitial brachytherapy, the brachytherapy can be administered at a high dose rate, a continuous low dose rate, or a pulsed dose rate. For example, and not by way of limitation, a high dose rate brachytherapy regimen can be a dose of 60 Gy administered in ten fractions over six days, while a continuous low dose rate brachytherapy regimen can be a total dose of about 65 Gy, administered continuously at about 40 to 50 cGy per hour. Other examples of high, continuous low, and pulsed dose rate brachytherapy are well known in the art. See, e.g., Mazeron et al., *Sem. Rad. One.* 12:95-108 (2002).

Representative radioisotopes that can be administered in any of the above-described brachytherapies include, but are not limited to, phosphorus 32, cobalt 60, palladium 103, ruthenium 106, iodine 125, cesium 137, iridium 192, xenon 133, radium 226, californium 252, or gold 198. Other radioisotopes may be selected for administration in brachytherapy according to the desirable physical properties of such a radioisotope. One of skill in the art will readily recognize that many properties will affect a radioisotope's suitability for use in brachytherapy, including, but not limited to, the radioisotope's half-life, the degree to which emitted radiation penetrates surrounding tissue, the energy of emitted radiation, the ease or difficulty of adequately shielding the radioisotope, the availability of the radioisotope, and the ease or difficulty of altering the shape of the radioisotope prior to administration.

Additional methods of administering and apparatuses and compositions useful for brachytherapy are described in U.S. Pat. Nos. 6,319,189, 6,179,766, 6,168,777, 6,149,889, and 5,611,767, each of which is incorporated herein by reference in its entirety.

In certain embodiments involving radiotherapeutic agents or treatments, the present invention relates to a method for treating cancer comprising the administration of vinca alkaloid or analog N-oxide having Formula I, in combination with a treatment comprising a therapeutically effective dose of a radionuclide. The radionuclide therapy can be administered according to any schedule, dose, or method known to one of skill in the art to be effective in the treatment or amelioration of cancer, without limitation. In general, radionuclide therapy comprises systemic administration of a radioisotope that preferentially accumulates in or binds to the surface of cancerous cells. The preferential accumulation of the radionuclide can be mediated by a number of mechanisms, including, but not limited to, incorporation of the radionuclide into rapidly proliferating cells, specific accumulation of the radionuclide by the cancerous tissue without special targeting (e.g., iodine 131 accumulation in thyroid cancer), or conjugation of the radionuclide to a biomolecule specific for a neoplasm.

Representative radioisotopes that can be administered in radionuclide therapy include, but are not limited to, phosphorus 32, yttrium 90, dysprosium 165, indium 111, strontium 89, samarium 153, rhenium 186, iodine 131, iodine 125, lutetium 177, and bismuth 213. While all of these radioisotopes may be linked to a biomolecule providing specificity of targeting, iodine 131, indium 111, phosphorus 32, samarium 153, and rhenium 186 may be administered systemically without such conjugation. One of skill in the art may select a specific biomolecule for use in targeting a particular neoplasm for radionuclide therapy based upon the cell-surface molecules present on that neoplasm. For example, hepatomas may be specifically targeted by an antibody specific for ferritin, which is frequently over-expressed in such tumors. Examples of antibody-targeted radioisotopes for the treatment of cancer include ZEVALIN (ibritumomab tiuxetan) and BEXXAR (tositumomab), both of which comprise an antibody specific for the B cell antigen CD20 and are used for the treatment of non-Hodgkin lymphoma.

Other examples of biomolecules providing specificity for particular cell are reviewed in an article by Thomas, *Cancer Biother. Radiopharm.* 17:71-82 (2002), which is incorporated herein by reference in its entirety. Furthermore, methods of administering and compositions useful for radionuclide therapy may be found in U.S. Pat. Nos. 6,426,400, 6,358,194, 5,766,571, and 5,563,250, each of which is incorporated herein by reference in its entirety.

In certain embodiments involving radiotherapeutic agents or treatments, the present invention relates to a method for treating cancer comprising the administration of vinca alkaloid or analog N-oxide having Formula I, in combination with a treatment comprising a therapeutically effective dose of external-beam radiation therapy. The external-beam radiation therapy can be administered according to any schedule, dose, or method known to one of skill in the art to be effective in the treatment or amelioration of cancer, without limitation. In general, external-beam radiation therapy comprises irradiating a defined volume within a subject with a high energy beam, thereby causing cell death within that volume. The irradiated volume preferably contains the entire cancer to be treated, and preferably contains as little healthy tissue as possible.

In certain embodiments, the external-beam radiation therapy can be three-dimensional conformal radiotherapy. In other embodiments, the external-beam radiation therapy can be continuous hyperfractionated radiotherapy. In still other embodiments, the external-beam radiation therapy can be intensity-modulated radiotherapy. In yet other embodiments, the external-beam radiation therapy can be helical tomotherapy. In still other embodiments, the external-beam radiation therapy can be three-dimensional conformal radiotherapy with dose escalation. In yet other embodiments, the external-beam radiation therapy can be stereotactic radiotherapy, including, but not limited to, single fraction stereotactic radiotherapy, fractionated stereotactic radiotherapy, and fractionated stereotactically guided conformal radiotherapy.

The external-beam radiation therapy can be generated or manipulated by any means known to one of skill in the art. For example, the photon beam used in external-beam radiation therapy can be shaped by a multileaf collimator. Other examples of suitable devices for generating a photon beam for use in external-beam radiation therapy include a gamma knife and a linac-based stereotactic apparatus. In certain embodiments, administration of the external-beam radiation therapy is controlled by a computer according to a three-dimensional model of the patient in the treatment position. Such a model can be generated, for example, by computed tomography (CT), magnetic resonance imaging (MRI), single photon emission computer tomography (SPECT), and positron emission tomography (PET). Use of such visualization methods can advantageously minimize the volume of healthy tissue treated, thereby allowing higher total doses of radiation to be administered to the patient.

In addition, healthy tissues can optionally be protected from the effects of the external-beam radiation therapy by placing blocking devices such as, e.g., lead shields, in locations where such protection is needed. Alternatively or additionally, metal reflecting shields can optionally be located to reflect the photon beam in order to concentrate the radiation on the cancerous tissue to be treated and protect healthy tissue. Placement of either shield is well within the knowledge of one of skill in the art.

Methods of administering and apparatuses and compositions useful for external-beam radiation therapy can be found in U.S. Pat. Nos. 6,449,336, 6,398,710, 6,393,096, 6,335,961, 6,307,914, 6,256,591, 6,245,005, 6,038,283, 6,001,054, 5,802,136, 5,596,619, and 5,528,652, each of which is incorporated herein by reference in its entirety.

In certain embodiments involving radiotherapeutic agents or treatments, the present invention relates to a method for treating cancer comprising the administration of vinca alkaloid or analog N-oxide having Formula I, in combination with a treatment comprising a therapeutically effective dose of thermotherapy. The thermotherapy can be administered according to any schedule, dose, or method known to one of skill in the art to be effective in the treatment or amelioration of cancer, without limitation. In certain embodiments, the thermotherapy can be cryoablation therapy. In other embodiments, the thermotherapy can be hyperthermic therapy. In still other embodiments, the thermotherapy can be a therapy that elevates the temperature of the tumor higher than in hyperthermic therapy.

Cryoablation therapy involves freezing of a neoplastic mass, leading to deposition of intra- and extra-cellular ice crystals; disruption of cellular membranes, proteins, and organelles; and induction of a hyperosmotic environment, thereby causing cell death. Cryoablation can be performed in one, two, or more freeze-thaw cycles, and further the periods of freezing and thawing can be adjusted for maximum tumor cell death by one of skill in the art. One exemplary device that can be used in cryoablation is a cryoprobe incorporating vacuum-insulated liquid nitrogen. See, e.g., Murphy et al., *Sem. Urol. Oncol.* 19:133-140 (2001). However, any device that can achieve a local temperature of about $-180°$ C. to about $-195°$ C. can be used in cryoablation therapy. Methods for and apparatuses useful in cryoablation therapy are described in U.S. Pat. Nos. 6,383,181, 6,383,180, 5,993,444, 5,654,279, 5,437,673, and 5,147,355, each of which is incorporated herein by reference in its entirety.

Hyperthermic therapy typically involves elevating the temperature of a neoplastic mass to a range from about $42°$ C. to about $44°$ C. The temperature of the cancer may be further elevated above this range; however, such temperatures can increase injury to surrounding healthy tissue while not causing increased cell death within the tumor to be treated. The tumor may be heated in hyperthermic therapy by any means known to one of skill in the art without limitation. For example, and not by way of limitation, the tumor may be heated by microwaves, high intensity focused ultrasound, ferromagnetic thermoseeds, localized current fields, infrared radiation, wet or dry radiofrequency ablation, laser photocoagulation, laser interstitial thermic therapy, and electrocautery. Microwaves and radiowaves can be generated by waveguide applicators, horn, spiral, current sheet, and compact applicators.

Other methods of and apparatuses and compositions for raising the temperature of a tumor are reviewed in an article by Wust et al., Lancet Oncol. 3:487-97 (2002), and described in U.S. Pat. Nos. 6,470,217, 6,379,347, 6,165,440, 6,163,726, 6,099,554, 6,009,351, 5,776,175, 5,707,401, 5,658,234, 5,620,479, 5,549,639, and 5,523,058, each of which is incorporated herein by reference in its entirety.

In certain embodiments involving radiotherapeutic agents or treatments, the present invention relates to a method for treating cancer comprising the administration of vinca alkaloid or analog N-oxide having Formula I, in combination with a treatment comprising a therapeutically effective dose of radiosurgery. The radiosurgery can be administered according to any schedule, dose, or method known to one of skill in the art to be effective in the treatment or amelioration of cancer, without limitation. In general, radiosurgery comprises exposing a defined volume within a subject to a manually directed radioactive source, thereby causing cell death within that volume. The irradiated volume preferably contains the entire cancer to be treated, and preferably contains as little healthy tissue as possible. Typically, the tissue to be treated is first exposed using conventional surgical techniques, then the radioactive source is manually directed to that area by a surgeon. Alternatively, the radioactive source can be placed near the tissue to be irradiated using, for example, a laparoscope. Methods and apparatuses useful for radiosurgery are further described in Valentini et al., Eur. J. Surg. Oncol. 28:180-185 (2002) and in U.S. Pat. Nos. 6,421, 416, 6,248,056, and 5,547,454, each of which is incorporated herein by reference in its entirety.

In certain embodiments involving radiotherapeutic agents or treatments, the present invention relates to a method for treating cancer comprising the administration of vinca alkaloid or analog N-oxide having Formula I, in combination with a treatment comprising a therapeutically effective dose of charged-particle radiotherapy. The charged-particle radiotherapy can be administered according to any schedule, dose, or method known to one of skill in the art to be effective in the treatment or amelioration of cancer, without limitation. In certain embodiments, the charged-particle radiotherapy can be proton beam radiotherapy. In other embodiments, the charged-particle radiotherapy can be helium ion radiotherapy. In general, charged-particle radiotherapy comprises irradiating a defined volume within a subject with a charged-particle beam, thereby causing cellular death within that volume. The irradiated volume preferably contains the entire cancer to be treated, and preferably contains as little healthy tissue as possible. A method for administering charged-particle radiotherapy is described in U.S. Pat. No. 5,668,371, which is incorporated herein by reference in its entirety.

In certain embodiments involving radiotherapeutic agents or treatments, the present invention relates to a method for treating cancer comprising the administration of vinca alkaloid or analog N-oxide having Formula I, in combination with a treatment comprising a therapeutically effective dose of neutron radiotherapy. The neutron radiotherapy can be administered according to any schedule, dose, or method known to one of skill in the art to be effective in the treatment or amelioration of cancer, without limitation.

In certain embodiments, the neutron radiotherapy can be a neutron capture therapy. In such embodiments, a compound that emits radiation when bombarded with neutrons and preferentially accumulates in a neoplastic mass is administered to a subject. Subsequently, the tumor is irradiated with a low energy neutron beam, activating the compound and causing it to emit decay products that kill the cancerous cells. Such compounds are typically boron containing compounds, but any compound that has a significantly larger neutron capture cross-section than common body constituents can be used.

The neutrons administered in such therapies are typically relatively low energy neutrons having energies at or below about 0.5 eV. The compound to be activated can be caused to preferentially accumulate in the target tissue according to any of the methods useful for targeting of radionuclides, as described below, or in the methods described in Laramore, *Semin. Oncol.* 24:672-685 (1997) and in U.S. Pat. Nos. 6,400,796, 5,877,165, 5,872,107, and 5,653,957, each of which is incorporated herein by reference in its entirety.

In other embodiments, the neutron radiotherapy can be a fast neutron radiotherapy. In general, fast neutron radiotherapy comprises irradiating a defined volume within a subject with a neutron beam, thereby causing cellular death within that volume. The irradiated volume preferably contains the entire cancer to be treated, and preferably contains as little healthy tissue as possible. Generally, high energy neutrons are administered in such therapies, with energies in the range of about 10 to about 100 million eV. Optionally, fast neutron radiotherapy can be combined with charged-particle radiotherapy in the administration of mixed proton-neutron radiotherapy.

In certain embodiments involving radiotherapeutic agents or treatments, the present invention relates to a method for treating cancer comprising the administration of vinca alkaloid or analog N-oxide having Formula I, in combination with a treatment comprising a therapeutically effective dose of photodynamic therapy. The photodynamic therapy can be administered according to any schedule, dose, or method known to one of skill in the art to be effective in the treatment or amelioration of cancer, without limitation. In general, photodynamic therapy comprises administering a photosensitizing agent that preferentially accumulates in a neoplastic mass and sensitizes the neoplasm to light, then exposing the tumor to light of an appropriate wavelength. Upon such exposure, the photosensitizing agent catalyzes the production of a cytotoxic agent, such as, e.g., singlet oxygen, which kills the cancerous cells.

Representative photosensitizing agents that may be used in photodynamic therapy include, but are not limited to, porphyrins such as porfimer sodium, 5-aminolaevulanic acid and verteporfin; chlorins such as temoporfin; texaphyrins such as lutetium texephyrin; purpurins such as tin etiopurpurin; phthalocyanines; and titanium dioxide. The wavelength of light used to activate the photosensitizing agent can be selected according to several factors, including the depth of the tumor beneath the skin and the absorption spectrum of the photosensitizing agent administered. The period of light exposure may also vary according to the efficiency of the absorption of light by the photosensitizing agent and the efficiency of the transfer of energy to the cytotoxic agent. Such determinations are well within the ordinary skill of one in the art.

Methods of administering and apparatuses and compositions useful for photodynamic therapy are disclosed in Hopper, *Lancet Oncol.* 1:212-219 (2000) and U.S. Pat. Nos. 6,283,957, 6,071,908, 6,011,563, 5,855,595, 5,716,595, and 5,707,401, each of which is incorporated herein by reference in its entirety.

It will be appreciated that both the particular radiation dose to be utilized in treating a hyperproliferative disorder and the method of administration will depend on a variety of factors. Thus, the dosages of radiation that can be used according to the methods of the present invention are determined by the particular requirements of each situation. The dosage will depend on such factors as the size of the tumor, the location of the tumor, the age and sex of the patient, the frequency of the dosage, the presence of other tumors, possible metastases and the like. Those skilled in the art of radiotherapy can readily ascertain the dosage and the method of administration for any particular tumor by reference to Hall, E. J., Radiobiology for the Radiologist, 5th edition, Lippincott Williams & Wilkins Publishers, Philadelphia, Pa., 2000; Gunderson, L. L. and Tepper J. E., eds., Clinical Radiation Oncology, Churchill Livingstone, London, England, 2000; and Grosch, D. S., Biological Effects of Radiation, 2nd edition, Academic Press, San Francisco, Calif., 1980. In certain embodiments, radiotherapeutic agents and treatments may be administered at doses lower than those known in the art due to the additive or synergistic effect of the compound having Formula I.

Compositions in accordance with the present invention may be employed for administration in any appropriate manner, e.g., oral or buccal administration, e.g., in unit dosage form, for example in the form of a tablet, in a solution, in hard or soft encapsulated form including gelatin encapsulated form, sachet, or lozenge. Compositions may also be administered parenterally or topically, e.g., for application to the skin, for example in the form of a cream, paste, lotion, gel, ointment, poultice, cataplasm, plaster, dermal patch or the like, or for ophthalmic application, for example in the form of an eye-drop, -lotion or -gel formulation. Readily flowable forms, for example solutions, emulsions and suspensions, may also be employed e.g., for intralesional injection, or may be administered rectally, e.g., as an enema or suppository, or intranasal administration, e.g., as a nasal spray or aerosol. Microcrystalline powders may be formulated for inhalation, e.g., delivery to the nose, sinus, throat or lungs. Transdermal compositions/devices and pessaries may also be employed for delivery of the compounds of the invention. The compositions may additionally contain agents that enhance the delivery of the compounds having Formula I (or other active agents), e.g., liposomes, polymers or co-polymers (e.g., branched chain polymers). Preferred dosage forms of the present invention include oral dosage forms and intravenous dosage forms.

When the unit dosage of the vinca alkaloid N-oxide, an analog, or a salt thereof is a solution or a suspension, the dosage form may be in a sealed container with substantially no carbon dioxide.

Intravenous forms include, but are not limited to, bolus and drip injections. In preferred embodiments, the intravenous dosage forms are sterile or capable of being sterilized prior to administration to a subject since they typically bypass the subject's natural defenses against contaminants. Examples of intravenous dosage forms include, but are not limited to, Water for Injection USP; aqueous vehicles including, but not limited to, Sodium Chloride Injection, Ringer's Injection, Dextrose Injection, Dextrose and Sodium Chloride Injection, and Lactated Ringer's Injection; water-miscible vehicles including, but not limited to, ethyl alcohol, polyethylene glycol and polypropylene glycol; and non-aqueous vehicles including, but not limited to, corn oil, cottonseed oil, peanut oil, sesame oil, ethyl oleate, isopropyl myristate and benzyl benzoate. In certain embodiments, vincristine N-oxide forms a clear solution at 5 mg/mL and at about 20 mg/mL in deionized water, in saline solution, and in 5% dextrose/water solution.

The pharmaceutical compositions of the present invention may further comprise one or more additives. Additives that are well known in the art include, e.g., detackifiers, antifoaming agents, buffering agents, antioxidants (e.g., ascorbic acid, ascorbyl palmitate, sodium ascorbate, butylated hydroxyanisole (BHA), butylated hydroxytoluene (BHT), propyl gallate, malic acid, fumaric acid, potassium metabisulfite, sodium bisulfite, sodium metabisulfite, and tocopherols, e.g., α-tocopherol (vitamin E)), preservatives, chelating agents, viscomodulators, tonicifiers, flavorants, colorants, odorants, opacifiers, suspending agents, binders, fillers, plasticizers, lubricants, and mixtures thereof. The amounts of such additives can be readily determined by one skilled in the art, according to the particular properties desired, and can be formulated such that compounds having Formula I are stable, e.g., not reduced by antioxidant additives.

The additive may also comprise a thickening agent. Suitable thickening agents may be of those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropylmethyl-cellulose phthallates; and salts thereof such as sodium-carboxymethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products.

Such thickening agents as described above may be included, e.g., to provide a sustained release effect. However, where oral administration is intended, the use of thickening agents may not be required. Use of thickening agents is, on the other hand, indicated, e.g., where topical application is foreseen.

In one embodiment of the invention, compounds having Formula I are formulated as described, for example, in U.S. Pat. No. 4,923,876.

Although the dosage of the compound having Formula I will vary according to the activity and/or toxicity of the particular compound, the condition being treated, and the physical form of the pharmaceutical composition being employed for administration, it may be stated by way of guidance that a dosage selected in the range from 0.1 to 20 mg/kg of body weight per day will often be suitable, although higher dosages, such as 0.1 to 50 mg/kg of body weight per day may be useful. Those of ordinary skill in the art are familiar with methods for determining the appropriate dosage. Methods for assessing the toxicity, activity and/or selectivity of the compounds having Formula I may be carried out using any of the methods known in the art, including the antiproliferative activity test.

In certain instances, the dosage of the compounds having Formula I will be lower, e.g., when used in combination with at least a second hyperproliferative disorder treatment, and may vary according to the activity and/or toxicity of the particular compound, the condition being treated, and the physical form of the pharmaceutical composition being employed for administration.

When the composition of the present invention is formulated in unit dosage form, the compound having Formula I will preferably be present in an amount of between 0.01 and 2000 mg per unit dose. More preferably, the amount of compound having Formula I per unit dose will be about 0.01, 0.05, 0.1, 0.5, 1, 5, 10, 20, 30, 40, 50, 60, 70, 80, 90, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2100, 2200, 2300, 2400, 2500, 2600, 2700, 2800, 2900, 3000, 3250, 3500, 3750, 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, or 10000 mg or any amount therein.

When the unit dosage form of the composition is a capsule, the total quantity of ingredients present in the capsule is preferably about 10-1000 μL. More preferably, the total quantity of ingredients present in the capsule is about 100-300 μL. In another embodiment, the total quantity of ingredients present in the capsule is preferably about 10-1500 mg, preferably about 100-1000 mg.

Irinotecan is preferably administered at a dose of about 5 mg/m$^2$ to about 500 mg/m$^2$, from about 50 mg/m$^2$ to about 300 mg/m$^2$, from about 75 mg/m$^2$ to about 200 mg/m$^2$. In a specific embodiment, an effective amount of irinotecan is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 mg/m$^2$ or more. In certain embodiments, an effective dose of irinotecan is between about 20 mg to about 500 mg, between about 40 mg to about 300 mg, between about 50 mg to about 200 mg, between about 75 mg to about 150 mg. In certain embodiments, the methods of the invention comprise administering irinotecan in a dose of about 0.1 mg/kg bodyweight to about 10 mg/kg body weight. In other embodiments, irinotecan may be administered in a dose of about 0.1, 0.2, 0.5, 1, 1.5, 2, 2.5, 3, 3.5, 4, 4.5, 5, 5.5, 6, 6.5, 7, 7.5, 8, 8.5, 9, 9.5, or 10 mg/kg bodyweight, or more. In certain embodiments, an effective dose of irinotecan is between about 0.5 mg/kg, to about 9 mg/kg, between about 1 mg/kg to about 8 mg/kg, between about 2 mg/kg to about 7 mg/kg, between about 3 mg/kg to about 5 mg/kg.

When the composition of the present invention is formulated in unit dosage form, irinotecan will preferably be present in an amount of between 10 mg and 1000 mg per unit dose. Preferably, the amount of irinotecan per unit dose will be about 10, 15, 20, 25, 30, 35, 40, 45, 50, 55, 60, 65, 70, 75, 80, 85, 90, 95, 100 115, 120, 125, 130, 135, 140, 145, 150, 155, 160, 165, 170, 175, 180, 185, 190, 195, 200, 210, 220, 230, 240, 250, 260, 270, 280, 290, 300, 350, 400, 450, or 500 mg or any amount therein. In one embodiment, the amount of irinotecan per unit dose will be about 50 mg to about 350 mg, about 75 mg to about 250 mg, about 100 mg to about 200. In one embodiment, the unit dosage form comprises 30, 45, 60, 75, 90, 120, 135, 150, or 180 mg of irinotecan.

In certain embodiments, the dosage of an N-oxide of vinca alkaloid or analog thereof will be administered according to a metronomic dosing. As used here, the term "metronomic dosing" refers to a dosing regimen, which uses a dose lower than the maximum tolerated doses (MTD) to minimize toxic side effects, administered at constant intervals without rest periods. For purposes of the present invention, the desired pharmacological effect of metronomic dosing with an N-oxide of vinca alkaloid or analog thereof is inhibition of tumor growth. "Inhibition of tumor growth" means causing a suppression of tumor growth and/or causing a regression in tumor size. It is believed that metronomic dosing elicits repeated waves of apoptosis of tumor endothelial cells by targeting cells of the vasculature which form the blood vessels of the tumor as opposed to the tumor cells themselves. Thus, metronomic dosing appears to abrogate tumor cells' apparent capability to repair and recover during the usual rest periods between episodic application of a cytotoxic drug at or near MTD, followed by periods of rest to allow normal tissues to recover.

The term "MTD" as used here for N-oxides of vinca alkaloids and analogs may be identified as part of the clinical evaluation of the N-oxide. For example, phase I trials can include a determination of the maximum tolerated dose, dose-limiting toxicities (DLT) and pharmacokinetics of an N-oxides of vinca alkaloids or analog. Thus, the MTD for any Food and Drug Administration (FDA) approved therapeutic compound can be determined by those of ordinary skill in the art. The MTD for any particular therapeutic compound may vary according to its formulation (e.g., injectable formulation, implantable bioerodible polymer formulation, oral formulation), route of delivery (e.g., intravenous, oral, intratumoral), manner of delivery (e.g., infusion, bolus injection), dosing schedule (e.g., hourly, daily, weekly) and the like. MTD frequently is defined as the highest dose level at which 50 percent of subjects administered with the drug develop a dose-limiting toxicity. Other definitions which are clinically relevant and generally accepted will be known to one of ordinary skill in the art.

The present invention also provides metronomic therapy regimes. In some embodiments, there is provided a metronomic dosing of an N-oxide of vinca alkaloid or analog, wherein the N-oxide is administered over a period of at least 1, 2, 3, 4, 5, 6, 7, or 8 weeks or 2, 3, 4, 5, 6, 7, 8, 9, 10, 11, 12, 18, 24, 30, or 36 months wherein the interval between each administration is no more than about 1, 2, 3, 4, 5, 6 or 7 days, and wherein the dose of the N-oxide of vinca alkaloid or analog at each administration is about 0.25% to about 80% of its MTD. In other embodiments, the vinca alkaloid N-oxide is administered at no more than 80%, 75%, 70%, 65%, 60%, 55%, 50%, 45%, 40%, 35%, 30%, 25%, 23%, 20%, 18%, 16%, 14%, 12%, 10%, 9%, 8%, 7%, 6%, 5%, 4%, 3%, 2%, or 1% of its MTD, which is predicted to be 100 mg/m$^2$ to 700 mg/m$^2$. In some embodiments, there is provided a method of administering a composition comprising an N-oxide of vinca alkaloid or analog, wherein the composition is administered over a period of at least one week, wherein the interval between each administration is no more than about a day, and wherein the dose of the N-oxide of vinca alkaloid or analog at each administration is about 0.25% to about 80% of its MTD or other doses mentioned herein. In some embodiments, there is provided a method of administering a composition comprising an N-oxide of vinca alkaloid or analog, wherein the composition is administered over a period of at least one month, wherein the interval between each administration is no more than about a week, and wherein the dose of the N-oxide at each administration is about 0.25% to about 80% of MTD or other doses mentioned herein. In some embodiments, the composition is administered at least about any of 1×, 2×, 3×, 4×, 5×, 6×, 7× (i.e., daily) a week.

In some embodiments, the compositions may be administered continuously over a pre-specified period, for example continuously transfusing the compositions for about 0.25 to about 80% of the MTD or other doses mentioned herein, wherein the pre-specified period is at least 1, 2, 3, 4, 5, 6, 7, or 8 weeks. In some embodiments, the intervals between successive continuous administration (e.g., infusion) sessions are at least about 1 day, 2 days, 3 days, 4 days, 5 days, six days, one week, 2 weeks, 3 weeks, 4 weeks, or 5 weeks after which a new continuous administration session is started.

In some embodiments, one or more patches applied at one or more parts of the body may be used to deliver a dose that does not exceed about 0.25 to about 80% of the MTD of the N-oxide per application period, or other doses mentioned herein. In some embodiments, the intervals between each administration by patch are less than about any of 7 days, 6 days, 5 days, 4 days, 3 days, 2 days, and 1 day. In some embodiments, the composition is administered by a patch over a period of at least about any of 1 day, 2 days, 3 days, 4 days, 5 days, six days, one week, 2 weeks, 3 weeks, 4 weeks, 5 weeks, 6 weeks, 7 weeks, or 8 weeks. In some embodiments, the intervals between successive patch administrations are at least about 1 day, 2 days, 3 days, 4 days, 5 days, six days, one week, 2 weeks, 3 weeks, 4 weeks, or 5 weeks after which one or more new patches are applied. Examples of transdermal patches that may be suitable to deliver metronomic doses of vinca alkoloid N-oxides and analogs thereof may be found in U.S. Pat. Nos. 6,977,070, 7,022,340, 6,004,581, 5,939,094, 5,624,677, 7,001,609, 6,632,522, 6,630,238, 6,482,871, 6,086,911, 5,698,217, 5,639,469, 5,244,677, 4,451,260, 6,173,851, 5,223,261, 5,192,548, 6,645,528, 5,700,480, 6,974,588, 6,238,693, 6,000,548, 4,726,951, 4,721,619, 5,225,196, 4,983,392, 6,103,257, 6,110,486, 5,955,098, 5,985,317, and 5,952,000.

In some embodiments, a controlled release formulation may be used to control release rate of the N-oxide of vinca alkaloid or analog from preparations so that a metronomic dosing regimen is maintained for a pre-determined period of time. In some embodiments, the metronomic dosing of the N-oxide of vinca alkaloid or analog may be maintained by using an erodable polymer matrix, reservoir device, microparticles, nanoparticles, osmotic pumps, or pH dependant coatings. In these embodiments, the N-oxide of vinca alkaloid or analog may be delivered at a dose that does not exceed about 0.25 to about 80% of the MTD of the N-oxide per application period, or other doses mentioned herein.

In some embodiments, there is provided a metronomic dosing of an N-oxide of vinca alkaloid or analog, wherein the N-oxide is administered over a period of at least 1, 2, 3, 4, 5, 6, 7, or 8 weeks or 2, 3, 4, 5, 6, 7, 8, 9, 10, 11, 12, 18, 24, 30, or 36 months, wherein the interval between each administration is no more than about a week, and wherein the dose of the N-oxide at each administration is about 25 mg/m$^2$ to about 500 mg/m$^2$. In some embodiments, there is provided a metronomic dosing of an N-oxide of vinca alkaloid or analog, wherein the N-oxide is administered over a period of at least three months, wherein the interval between each administration is no more than about a week, and wherein the dose of the N-oxide at each administration is about 25 mg/m$^2$ to about 500 mg/m$^2$. In some embodiments, there is provided a metronomic dosing of an N-oxide of vinca alkaloid or analog, wherein the N-oxide is administered over a period of at least one month, wherein, the interval between each administration is no more than about one day, two days, three days, four days, five days, six days, or one week, and wherein the dose of the N-oxide at each administration is about 25 mg/m$^2$ to about 500 mg/m$^2$. In some embodiments, there is provided a metronomic dosing of an N-oxide of vinca alkaloid or analog, wherein the N-oxide is administered over a period of at least one week, wherein the interval between each administration is no more than about 12, 24, 36, 48, 60, 72, 84, 96, 108, or 120 hours, and wherein the dose of the N-oxide at each administration is about 25 mg/m$^2$ to about 500 mg/m$^2$. In some embodiments, the dose of the N-oxide of vinca alkaloid or analog per administration is less than about any of 25, 30, 35, 40, 45, 50, 55, 60, 70, 80, 90, 100, 120, 140, 160, 180, 200, 250, 300, 350, 400, 450, and 500 mg/m$^2$. In some embodiments, the composition is administered at least about any of 1×, 2×, 3×, 4×, 5×, 6×, and 7× (i.e., daily) a week. In some embodiments, the intervals between each administration are less than about any of 7 days, 6 days, 5 days, 4 days, 3 days, 2 days, and 1 day.

The relative proportion of ingredients in the compositions of the invention will, of course, vary considerably depending on the particular type of composition concerned. The relative proportions will also vary depending on the particular function of ingredients in the composition. The relative proportions will also vary depending on the particular ingredients employed and the desired physical characteristics of the product composition, e.g., in the case of a composition for topical use, whether this is to be a free flowing liquid or a paste. Determination of workable proportions in any particular instance will generally be within the capability of a person of ordinary skill in the art. All indicated proportions and relative weight ranges described below are accordingly to be understood as being indicative individually inventive teachings only and not as limiting the invention in its broadest aspect.

The amount of compound having Formula I in compositions of the invention will of course vary, e.g., depending on the intended route of administration and to what extent other components are present. In general, however, the compound having Formula I will suitably be present in an amount of from about 0.005% to 20% by weight based upon the total weight of the composition. In certain embodiments, the compound having Formula I is present in an amount of from about 0.01% to 15% by weight based upon the total weight of the composition.

In addition to the foregoing, the present invention also provides a process for the production of a pharmaceutical composition as hereinbefore defined, which process comprises bringing the individual components thereof into intimate admixture and, when required, compounding the obtained composition in unit dosage form, for example filling said composition into tablets, gelatin, e.g., soft or hard gelatin, capsules, or non-gelatin capsules.

The starting materials of the N-oxides of the present invention are known and described, for example, in U.S. Pat. Nos. 6,555,547, 6,365,735, RE37,449, 6,127,377, 5,369,111, 5,030,620, 5,024,835, 4,831,038, 4,765,972, RE30,561 and 4,160,767.

In certain situations, more than one of the nitrogen atoms of the vinca alkaloid analog may be oxidized simultaneously. In certain cases, one or more of the multiple N-oxide groups may be reduced selectively, leaving one or more of the other N-oxide groups in place. Thus, the present invention contemplates the preparation of N-oxide analogs in which one or more of the nitrogen atoms that are suitable for N-oxide formation are present as the N-oxide without regard to the susceptibility of a particular nitrogen atom to N-oxide formation or the susceptibility of a particular N-oxide group to reduction. It is envisaged to employ a combination of suitable protecting groups (see: Greene, T. W.; Wuts, P. G. M. *Protective Groups in Organic Synthesis*, second edition, Wiley Interscience, 1991) to protect those nitrogen atoms not undergoing oxidation.

By way of an example, primary and secondary amines that may be present in a vinca alkaloid analog may be protected using, for example, tert-butyl sulfonyl (BUS) group. Jarowicki, K. and Kocienski, P., *J. Chem. Soc., Perkin Trans* 1, 4005-4037, 4029 (1998); Sun, P. and Weinreb, S. M. *J. Org. Chem.* 62:8604-08 (1997). The BUS protecting group is introduced by reaction of the amine with tert-butylsulfinyl chloride followed by oxidation of the sulfinyl amide with, for example, dimethyldioxirane, m-chloroperbenzoic acid or $RuCl_3$ catalyzed $NaIO_4$. The oxidation step in the preparation of the BUS-protected primary or secondary amines may also oxide any tertiary amine and heteroaromatic nitrogen present in the compounds. Thus, this protecting group may be introduced into primary and secondary amines while simultaneously oxidizing tertiary and heteroaromatic nitrogen atoms.

The BUS protecting group is stable towards strong reagents such as alkyllithium, Grignard reagents, 0.1M HCl in MeOH (20° C., 1 hr), 0.1M TFA in dichloromethane (20° C., 1 hr) and pyrolysis at 180° C. The BUS-protected secondary amines can be cleaved with 0.1 M triflic acid in dichloromethane containing anisole as a cation scavenger at 0° C. for 15-30 minutes while primary amines are released more slowly at room temperature. If desired, both BUS-protected primary and secondary amines may be deprotected with 0.1 M triflic acid in dichloromethane containing anisole as a cation scavenger at 25° C. for 2.5 hours. Thus, the BUS protecting group may allow protecting primary and secondary amines simultaneously while also oxidizing tertiary amines and heteroaromatic nitrogen atoms to the N-oxides. Moreover, the BUS protecting group may allow protecting primary and secondary amines simultaneously, oxidizing tertiary amines and heteroaromatic nitrogen atoms to N-oxides, deprotect the secondary amine selectively, alkylate the secondary amine to a tertiary amine, oxidize the resulting tertiary amine and deprotect the primary amine. Alternatively, a primary and a secondary amine may be protected with BUS protecting group, the secondary amine may be deprotected selectively, the secondary amine may be protected with, for example, Boc protecting group, and then the primary amine may be deprotected selectively followed by alkylation and oxidation. Thus, when a primary amine and a secondary amine are present in a vinca alkaloid analog, a BUS protecting group may be used to transform one of amines to an N-oxide without affecting the other.

Recent development in the use of Boc group to protect amines allows introduction and removal of the group under mild conditions. For example, a vinca alkaloid analog amine group may be protected with Boc group by simply mixing the analog and Boc-ON (2-(Boc-oxyimino)-2-phenylacetonitrile, available from Aldrich Co.) in benzene at 25° C. for 20 minutes (or 6 hours if the amine is an electron deficient aniline) in the presence of powdered zinc. See Spivey, A. C. and Maddaford A. *Annu. Rep. Prog. Chem.*, Sect. B, 95:83-95 (1999). Alkyl esters are tolerated.

Boc-protected amines are generally deprotected using triflic acid although recent developments generally use mildly acidic conditions that leave acid-labile groups unaffected. For example, heating Boc protected p-anisidines at 180° C. in the presence of 4-chlorophenol deprotects the amine group without affecting acid sensitive methoxy enols (—CH═C (OCH$_3$)—). Jarowicki, K. and Kocienski, P., *J. Chem. Soc., Perkin Trans* 1, 4005-4037, 4025 (1998). Thus, primary and secondary amines in vinca alkaloid may be protected with Boc group followed by oxidation of the tertiary amines and deprotection of the primary and secondary amines.

It has also recently been reported a new base-sensitive amino protecting group 1,1-dioxobenzo[b]thiophene-methoxycarbonyl (Bsmoc). Bsmoc is introduced via its chloroformate or N-hydroxy-succinimide derivative. The Bsmoc group is stable towards tertiary amines for 24 hours but is removed within 3-5 minutes using piperidine. Jarowicki, K. and Kocienski, P., *J. Chem. Soc., Perkin Trans* 1, 4005-4037, 4027 (1998). Thus, primary and secondary amines present in vinca alkaloid analogs may conveniently be protected with Bsmoc protecting group followed by oxidation of the tertiary amines and removal of the protecting group under mild conditions.

It has also been reported that certain heteroaromatic nitrogen atoms can be oxidized selectively in the presence of certain aromatic primary amines and certain secondary amines adjacent to a double bond. Delia, T. J. et al. *J. Org. Chem.* 30:2766-68 (1965). For example, oxidation of cytosine with m-chloroperbenzoic acid results in cytosine 3-N-oxide despite the presence of aromatic primary amine and a secondary amine. Thus, heteroaromatic nitrogen atoms and tertiary amines may be oxidized in the presence of certain aromatic primary amines and secondary amines.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

Figure 1:
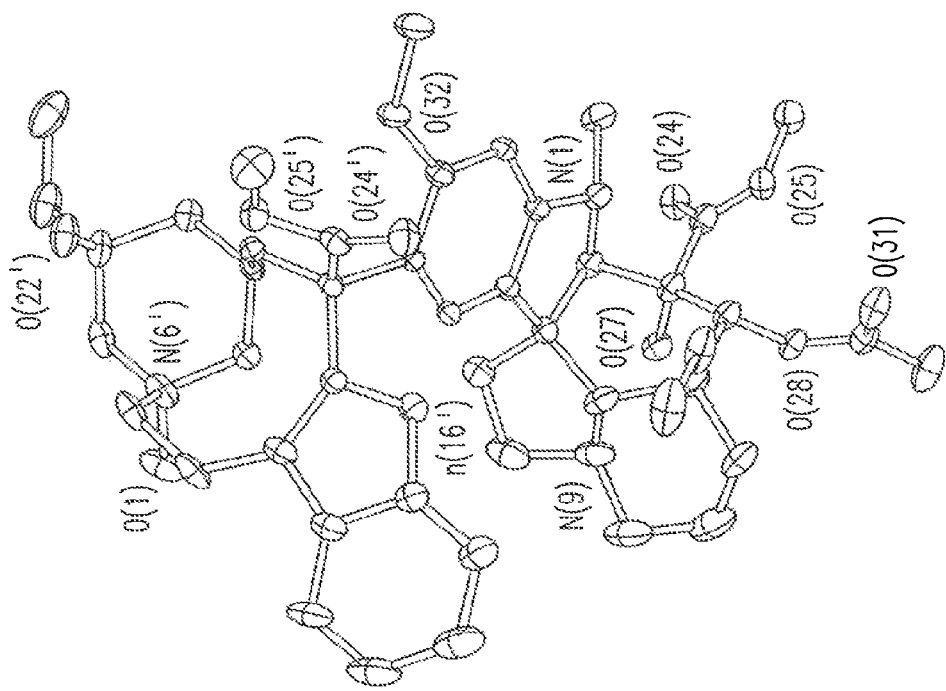
FIG. 1 shows x-ray single crystal structure of vinblastine N-oxide. The chemical structure of the compound is also shown for comparison purposes.
Figure 1:
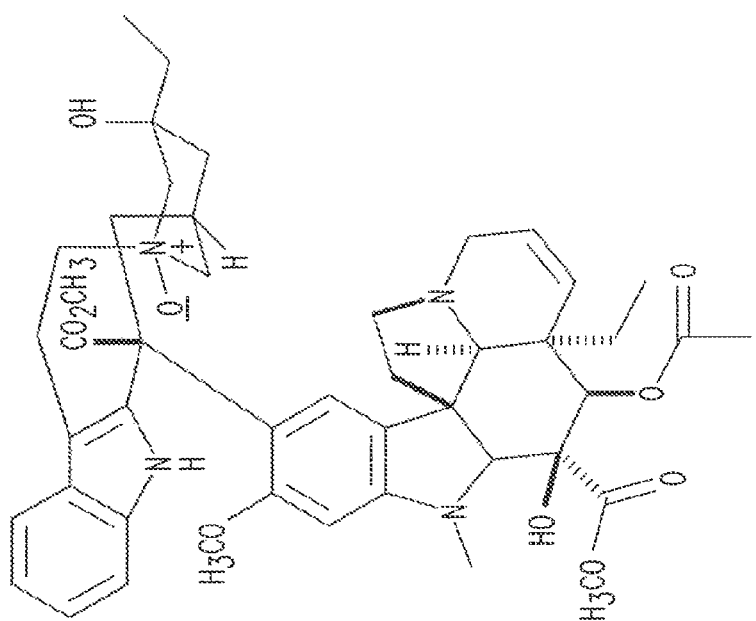

EXAMPLES $^1$H NMR spectra were obtained from INOVA-300 MHz or INOVA-500 MHz spectrometers using $D_2O$ or $CDCl_3$ as a solvent (s, d, t, dd and m indicate singlet, doublet, triplet, doublet of doublet, and multiplet, respectively). Analytical thin-layer chromatography was performed on polyester-backed plates from EMD Chemicals, Inc., precoated with silica gel 60 $F_{254}$. Radial thin-layer chromatography was performed on a Harrison Research Chromatron (7924T) using 2 mm thick silica plates coated in our laboratory with silica gel 60 $PF_{254}$ containing gypsum (EMD Chemicals, Inc.). Analytical scale high-performance liquid chromatography (HPLC) was performed on a 4.6 mm×250 mm MICROSORB $C_{18}$ column using a pressure of 1800-2100 psi. The procedure for the synthesis for the N-oxides of vinblastine, vincristine, and vinorelbine was adapted from P. Mangeney et al. for the procedure for oxidation of vinorelbine. The formation of vinblastine N-oxide leads to the formation of a new stereocenter. We have determined the configuration of the newly introduced oxygen atom in vinblastine $N'_b$-oxide synthesized below to be cis to the nearby ethyl group by single crystal x-ray analysis of the maleate salt (FIG. 1). Both epimers of the N-oxide on either the $R_8$ or $R'_8$ nitrogen atom in Formula I are contemplated in this invention. Vinblastine N-oxide is an intermediate for the synthesis of vinorelbine. See Mangeny, P. et al. *Tetrahedron.* 35:2175-2179 (1979).

Example 1

Synthesis of Vinblastine $N'_b$-Oxide Free Base And Salts

Sub-Gram Scale

Vinblastine free base. Vinblastine sulfate was purchased from Asian Talent. A 610-mg sample of vinblastine sulfate was dissolved in 20 mL of dichloromethane and then it was shaken with 20 mL of 5% aqueous sodium carbonate. The organic layer was separated and aqueous solution was extracted with dichloromethane (2×20 mL) and then with chloroform (20 mL). The combined organic layer and extracts were dried over sodium sulfate and evaporated to dryness, affording 526 mg (97%) of vinblastine free base as a sticky white solid. The purity of vinblastine free base was checked by $^1$H 300 MHz NMR and HPLC (99.1% AUC) using a Varian CHROMSEP HPLC column SS 250×4.6 mm including holder with guard column, MICROSORB 100-5 C18; gradient: 30/70 (0.1% trifluoroacetic acid in acetonitrile)/(0.1% trifluoroacetic acid in water) to 100/0 (0.1% trifluoroacetic acid in acetonitrile)/(0.1% trifluoroacetic acid in water); detection at 254 nm and 270 nm.

Vinblastine N-oxide free base. To a stirred solution of vinblastine free base (526 mg, 0.65 mmol) in $CH_2Cl_2$ (5 mL) at 0° C. was added dropwise a chilled solution of m-chloroperoxybenzoic acid (168 mg, 0.97 mmol) in 6 mL of $CH_2Cl_2$. The progress of the reaction was followed by silica gel TLC (eluent: 5:0.7 $CHCl_3$-MeOH; vinblastine $R_f$=0.65; vinblastine N-oxide $R_f$=0.25). The reaction was complete after ~2 min. The solution was washed with aqueous sodium carbonate (10 mL, 5 g/100 mL) to remove m-chlorobenzoic acid and any remaining m-chloroperoxybenzoic acid. The organic layer was dried over sodium sulfate and the solvent was evaporated under reduced pressure, yielding crude vinblastine N-oxide (600 mg). Chromatography over a short column of silica gel (eluent: 5:0.5 $CHCl_3$-MeOH) followed by radial chromatography (eluent: 5:0.5 $CHCl_3$-MeOH) gave vinblastine N-oxide (340 mg, 64%) as a beige powder. For larger scale preparations, the N-oxide may be obtained in comparable purity and yield by column chromatography over silica gel (eluent: 5:0.3 $CHCl_3$-MeOH to 5:0.7 $CHCl_3$-MeOH). The silica gel should be deactivated with methanol prior to the chromatography. The 500 MHz $^1$H NMR spectrum of vinblastine $N'_b$-oxide in $CDCl_3$ is consistent with the assigned structure. HPLC, >98% AUC.

Hydrogen Chloride Salt of Vinblastine N-oxide. A 55-mg (0.066 mmol) sample of vinblastine N-oxide was dissolved in 4 mL of methanol. The solution was cooled to −30° C. and then 33 μL (0.066 mmol) of 2N HCl in water was added. The resulting solution was stirred for 5 min. Then solvent was evaporated and the residue was dissolved in deionized water (4 mL), filtered and lyophilized to give the HCl salt of vinblastine N-oxide as a white somewhat hygroscopic powder. The 300 MHz $^1$H NMR spectrum in $D_2O$ is consistent with the assigned structure.

Maleic Acid salt of Vinblastine N-oxide. A 15-mg (0.018 mmol) sample of vinblastine N-oxide was dissolved in 2 mL of methanol. To this solution was added 2 mg (0.018 mmol) of maleic acid dissolved in 0.170 mL of methanol at room temperature. The solution was stirred for 5 min and then evaporated. Dichloromethane (DCM, 5 mL) was added to the residue and then the solution was concentrated to dryness to give 17 mg of the maleic acid salt of vinblastine N-oxide. The sample was dissolved in $D_2O$ (0.7 mL) for an NMR spectrum, which was consistent with the assigned structure. The $D_2O$ solution was allowed to stand at room temperature overnight. White plate-like crystals separated. Single crystal x-ray analysis (FIG. 1) confirmed that the newly introduced oxygen atom is attached to the $N'_b$ nitrogen atom and that this oxygen atom is cis to the ethyl group at the 20' position as seen in FIG. 1. The configuration of the N-oxide oxygen atom in vinblastine $N'_b$-oxide is the same as that of the methiodide methyl group in leurocristine methiodide dehydrate as described in the x-ray crystal structure reported by Moncrief and Lipscomb (Moncrief, J. W.; Lipscomb, W. N. *Acta Cryst.* 1966, 21, 322).

Example 2

Synthesis of Vinblastine $N'_b$-Oxide Free Base And Salts

Multi-Gram Scale

Vinblastine Free Base. A 3-L, three-neck, round-bottom flask equipped with a mechanical stirrer, a nitrogen inlet, an addition funnel, and a temperature probe was purged with nitrogen. The flask was charged with a solution of vinblastine sulfate (40.0 g, 44 mmol, Guangzhou Huanye Pharmaceutical Co.) in DCM (600 mL), followed by the addition of a 10% solution of $Na_2CO_3$ (140 mL, 132 mmol) at 0-5° C. over 10 min. The mixture was allowed to agitate at 0-5° C. for 20 min and then the layers were separated after 5 min. The aqueous layer was extracted with DCM (2×200 mL) by agitating the mixture for 5 min and allowing phases to separate for 5 min. Analysis of the aqueous layer after the extractions did not show any product. The combined organic extracts were washed with water (200 mL) and dried over sodium sulfate. HPLC analysis of the organic solution indicated 98.5% purity for the product. This solution (1.2 L) was diluted with DCM (0.6 L) and progressed to the oxidation step without concentration.

Vinblastine N-Oxide free base. A 3-L, three-neck, round-bottom flask equipped with a mechanical stirrer, a nitrogen inlet, an addition funnel, and a temperature probe was purged with nitrogen. The flask was charged with the solution of vinblastine free base in DCM (1.8 L), followed by the addition of a 70-75% solution of m-CPBA (10.6 g, 44 mmol) in DCM (0.5 L) at −75 to −70° C. over 45 minutes. An in-process analysis by TLC after 5 minutes indicated the full consumption of vinblastine and formation of the N-oxide. The mixture was warmed to −10° C. and quenched with a 10% solution of $Na_2CO_3$ (200 mL) by agitating the mixture at −10 to 0° C. for 5 minutes. The organic solution was separated after 5 minutes and washed with 10% $Na_2CO_3$ (200 mL), followed by water (200 mL). The solution was dried over sodium sulfate and concentrated under vacuum. This afforded 40.2 grams of the crude product as a wet solid in 96.5% purity.

The crude N-oxide was dissolved in a 1:1 mixture of DCM/DMF (60 mL) and diluted with MTBE (600 mL). The resultant slurry was agitated at ambient temperature for 15 minutes. The solids were filtered and washed with MTBE (80 mL). The product was dried under vacuum at ambient temperature for 18 hours. This process yielded 37.3 g (102%) of the product in 97.8% purity as a white solid. Proton NMR spectrum of the solid was consistent with the structure of the compound.

Vinblastine N-Oxide Dihydrochloride. A 1-L, three-neck, round-bottom flask equipped with a mechanical stirrer, a nitrogen inlet, an addition funnel, and a temperature probe was purged with nitrogen. The flask was charged with a solution of vinblastine N-oxide (37.3 g) in 2:1 isopropyl alcohol (IPA)/MeOH (120 mL) and diluted with isopropyl acetate (IPAc, 200 mL). The resultant solution was cooled to −35 to −30° C. A 4 N solution of HCl in IPA (21.1 mL, 84.4 mmol) was added over 10 min and the mixture was allowed to stir at this temperature for 5 minutes. The mixture was then diluted with IPAc (1.4 L, 35 vol) and allowed to stir at 0-10° C. for 30 minutes. The solids were filtered and washed with IPAc (200 mL). HPLC analysis of the wet cake indicated 98.0% purity for the product. The product was dried under vacuum at ambient temperature and 29-30 in. Hg for 58 hours. This provided 35.4 g of the product as a white solid. HPLC analysis indicated 97.7% purity for the solid. NMR spectrum was consistent with the structure of the compound but indicated 7 wt % of residual IPAc, 1 wt % IPA, and 1 wt % DMF.

Diethyl Ether Slurry of Vinblastine N-Oxide Dihydrochloride Salt. The batch (33.3 g) was suspended in diethyl ether (500 mL, 15 vol) at 0-5° C. and agitated for 18 hours. The batch was filtered and the solids were dried at ambient temperature and 29-30 in. Hg for 24 hours. This provided 29.9 g of the salt as a white solid. HPLC analysis indicated 96.6% purity for the solid. $^1$H NMR and mass spectra were consistent with the structure of the compound but indicated ≈0.3 wt % diethyl ether.

Example 3

Synthesis of Vinorelbine N'$_b$-Oxide

Vinorelbine free base was purchased from Asia Talent. Purification, when necessary, was accomplished by radial chromatography on silica gel using 9:1 $CHCl_3$-MeOH as eluent.

Vinorelbine N'$_b$-oxide was synthesized using essentially the same procedure used to prepare vinblastine N'$_b$-oxide. m-Chloroperoxybenzoic acid (45 mg, 0.26 mmol) in $CHCl_3$ (2.5 mL) was added at 0° to a stirred solution of purified vinorelbine (150 mg, 0.20 mmol) in $CHCl_3$ (4.5 mL) under nitrogen. After 15 min, the mixture was poured into an aqueous sodium carbonate (27 mL, 40 g/L) and was extracted by $CHCl_3$ (20 mL). After drying over sodium sulfate and filtration, the $CHCl_3$ extract was evaporated under reduced pressure affording crude vinorelbine N-oxide (125 mg, 83%). Thin-layer chromatography (silica; 9:1 $CHCl_3$/MeOH) indicated the presence of a small amount of starting vinorelbine (vinorelbine $R_f$=0.37, vinorelbine N'$_b$-oxide $R_f$=0.18). Radial chromatography on silica gel (eluent, 9:1 $CHCl_3$/MeOH) gave vinorelbine N'$_b$-oxide as an off-white solid (100 mg; 75%). The sample was dissolved in ethyl acetate/hexanes and then the open flask was placed in a sealed container containing an open flask of hexanes. As the hexanes diffused slowly into the vinorelbine N'$_b$-oxide solution, vinorelbine N'$_b$-oxide precipitated out as an off-white powder (80 mg; 53%). The 300 MHz $^1$H NMR spectrum was consistent with the assigned structure. The configuration of the N'$_b$-oxide oxygen atom is assigned the same stereochemistry as that found in vinblastine N-oxide by x-ray crystallography.

Example 4A

Synthesis of Vincristine N'$_b$-Oxide

Vincristine Free Base. Vincristine sulfate was purchased from Asian Talent. A 480-mg sample of vincristine sulfate was dissolved in 10 mL of 7:3 chloroform/methanol and then it was shaken with a 15 mL of 5% aqueous sodium carbonate. The organic layer was separated and aqueous solution was then extracted with dichloromethane (2×20 mL) followed by chloroform (2×20 mL). The combined organic layer and extracts were dried over sodium sulfate and concentrated to dryness, affording 420 mg (98%) of vincristine free base as a sticky yellowish-white solid. The purity of vincristine free base was checked by 1H 300 MHz NMR and HPLC (99.0% AUC).

Vincristine N'$_b$-Oxide. m-Chloroperoxybenzoic acid (132 mg, 0.76 mmol) in 2 mL of dichloromethane was added dropwise at 0° C. to a stirred solution of vincristine free base (420 mg, 0.51 mmol) in dichloromethane (4 mL). The progress of the reaction was followed by silica gel TLC (eluent: 5:0.5 $CHCl_3$-MeOH; vincristine $R_f$=0.65; vincristine N-oxide $R_f$=0.30) and was complete after ~2 min. The solution was washed with aqueous sodium carbonate (8 mL, 5 g/100 mL) to remove m-chlorobenzoic acid and any remaining m-chloroperoxybenzoic acid. The organic layer was dried over sodium sulfate and the solvent was evaporated under reduced pressure, yielding crude vincristine N-oxide (450 mg). Chromatography over a short column of silica gel (eluent: 5:0.5 $CHCl_3$-MeOH) followed by radial chromatography over silica gel (eluent: 5:0.5 CHCl$_3$-MeOH) gave vincristine N-oxide (288 mg, 67%) as an off-white powder. The 300 MHz $^1$H NMR spectrum in CDCl$_3$ was consistent with the assigned structure. Reverse phase HPLC showed a purity of >98% (AUC). The configuration of the N-oxide oxygen atom is assigned the same stereochemistry as that found in vinblastine N-oxide by x-ray crystallography.

Example 4B

Synthesis of Vincristine N'$_b$-Oxide

Vincristine Free Base. Vincristine sulfate was purchased from Asian Talent. A 970-mg sample of vincristine sulfate was dissolved in 20 mL of 19:1 methylene chloride/methanol and then it was shaken with a 20 mL of 5% aqueous sodium carbonate. The organic layer was separated and aqueous solution was then extracted with dichloromethane (2×30 mL) followed by chloroform (1×30 mL). The combined organic layer was washed with water and extracts were dried over sodium sulfate and concentrated to dryness, affording 870 mg (100%) of vincristine free base as a sticky yellowish-white solid. The purity of vincristine free base was checked by $^1$H 300 MHz NMR and HPLC (99.0% AUC).

Vincristine N'$_b$-Oxide. To a stirred solution of Vincristine free base (870 mg, 1.00 mmol) in CH$_2$Cl$_2$ (130 mL) at −78° C. a chilled (by standing on dry ice) solution of m chloroperbenzoic acid (66% m-CPBA, Aldrich, 273 mg, 1.60 mmol) in 40 mL of CH$_2$Cl$_2$ was added dropwise by way of an unchilled separatory funnel during 30 minutes. The progress of the reaction was followed by TLC (eluent: CH$_2$Cl$_2$-MeOH, 5:0.8, R$_f$-Vincristine 0.80, R$_f$-Vincristine N-oxide 0.30). The reaction was complete after 10 minutes. The resulting solution was warmed to −10° C. and washed with aqueous Na$_2$CO$_3$ (3×10 mL, 5 g/100 mL) to remove excess of m-CPBA and the resulting m-chlorobenzoic acid. The organic layer was washed with water, dried over sodium sulfate and the solvent was evaporated under reduced pressure in a 35° C. bath, yielding crude Vincristine N-oxide (about 900 mg). Column chromatography over silica gel (60-200 mesh, VWR International, Inc., in 100% CH$_2$Cl$_2$, eluent, CH$_2$Cl$_2$-MeOH. 5:0.5 to 5:1) gave Vincristine N-oxide as an off white solid (670 mg, 74%). The silica gel (50 g of silica gel per 1 g of N-oxide) should be deactivated by washing with methylene chloride/methanol, 5:0.5 mixture before using for the chromatography. The 300 MHz $^1$H NMR spectrum in CDCl$_3$ was consistent with the assigned structure. Reverse phase HPLC showed a purity of >99% (AUC).

Example 5

Cytotoxicity of Vinca-alkaloids and Analog N-Oxides Thereof in Lymphoma, Leukemia, Multiple Myeloma and Cells Derived from Hemtalogical Malignancies The cytotoxicity of vinca alkaloids and analog N-oxides thereof on different lymphoma, leukemia, and multiple myeloma cell lines will be tested in vitro under normoxic as well as 0.2% O$_2$ hypoxic conditions. Standard viability assays using MTT or Alamar Blue dye will be conducted to determine the 50% Inhibitory Concentration (IC$_{50}$) for each compound. Cultured tumor cells will be treated with the compounds for 8 hr or greater under normoxic or hypoxic conditions, and viability will be measured 24-48 hr later. In certain cases, enzyme inhibitors to bioreductive enzymes will be co-cultured with the cells to verify mechanism of action.

Positive controls will use chemotherapeutic agents at doses shown in the art to be effective. The results should indicate that vinca alkaloids and its related N-oxide analogs are cytotoxic to many of the cell lines derived from hematological malignancies, with IC$_{50}$ values in the nanomolar to sub-nanomolar range. Vinca alkaloid analog N-oxides are expected to be increased or differential cytotoxicity profiles than the parent compounds under normoxic or euoxic conditions.

Example 6

Anti-Tumor Activity of Vinca-Alkaloids and Analog N-Oxides Thereof in Lymphoma, Leukemia, Multiple Myeloma and Cells Derived from Hemtalogical Malignancies The in vivo antitumor efficacy of vinca alkaloids and analog N-oxides will be evaluated using syngeneic and xenotransplant experimental murine models of hematological malignancies. For example, DBA/2 mice (n=12/group) will be inoculated intraperitoneally (ip) with 1×10$^5$ murine L1210 or 1×10$^6$ P388 leukemic tumor cells. Following tumor implantation, mice will be treated with 10-1000 mg/kg of vinca alkaloids and analog N-oxides by intravenous administration. Agents may be administered on a single or multiple treatment regimen (ie. once weekly, q3d) to yield optimal dose schedule benefit. The effects of treatment with vinca alkaloids and N-oxide analogs compared to vehicle control treated mice on prolonging the survival of tumor bearing mice will be compared using a pre-determined survival endpoint. Animals will also be monitored for symptoms of acute toxicity such as body weight loss, neurotoxicities, lymphopenia and neutropenia. As a positive control, treatment will be compared with a standard agent.

In a related example, the in vivo antitumor efficacy of vinca alkaloids and analog N-oxides will be evaluated using a Namalwa human lymphoma xenograft model in nude mice. Female nu/nu mice (n=10/group) will be implanted with human Namalwa lymphoma cells by subcutaneous injection. Pair-matched mice will be randomized to different treatment groups when their tumors are approximately 50-100 mm$^3$ in size as determined by caliper measurements. Mice will be treated with 10-1000 mg/kg of vinca alkaloids and analog N-oxides by intravenous administration on a weekly or once every 3 day schedule. The anti-tumor effects of the compounds will be assessed as tumor growth inhibition (TGI) and tumor growth delay (TGD) by established criteria and practices known in the art. Treatment effects will also be compared to a standard agent known in the art such as mitoxantrone or doxorubicin.

In a related example, the in vivo antitumor efficacy of vinca alkaloids and analog N-oxides will be demonstrated in a human xenotransplantion model of acute lymphocytic leukemia (ALL) in immunodeficient mice. NOD/SCID mice will be implanted with primary human ALL tumor cells. Tumor grafting and burden will be monitored by flow cytometry using standard leukemia identification markers and pair-matched animals will be randomized into control or treatment groups. Seven to 10 days following transplant, mice will be injected intravenously (iv) with 10-1000 mg/kg of vinca alkaloids and analog N-oxides by intravenous administration on a weekly or once every 3 day schedule. Mice will be bled routinely and assessed for tumor burden by FACS analysis. The number of leukemic tumor cells per ml of blood prior and post-treatment will be compared to evaluate compound efficacy. Animals will also be monitored for symptoms of acute toxicity such as body weight loss, neurotoxicities, lymphopenia and neutropenia. As a positive control, treatment will be compared with a standard agent.

Further, the in vivo antitumor activity of vinca alkaloids and analog N-oxide in combination with chemotherapeutic agents and/or radiotherapy will be evaluated using a xenograft model in nude mice.

Further, the in vivo antitumor activity of vinca alkaloids and analog N-oxide in combination with therapeutic monoclonal antibodies such as anti-CD52 (Campath), anti-CD20 (Rituxan, Zevalin, Bexxar), anti-CD22 (LymphoCide) anti-CD33 (MyloTarg), or HLA-DR (Lym-1, Oncolym) will be evaluated using a xenograft model in nude mice.

Further, the in vivo antitumor activity of vinca alkaloids and analog N-oxide in combination with small molecular weight inhibitors of kinases such as imatanib (Gleevec) will be evaluated using a xenograft model in nude mice.

Example 7

Cytotoxicity of Vinca-alkaloid Analogs and N-Oxides Thereof in Solid Tumor Lines The differential cytotoxicity of vinca-alkaloids and analog N-oxides thereof on different solid tumor cell lines are demonstrated in vitro under normoxic conditions and 0.2% $O_2$ hypoxic conditions. Shown in FIGS. 2A-2D and 3A-3D and Tables 2 and 3 are results obtained from treatment effects of vinblastine N-oxide and vincristine N-oxide, against human H460 lung adenocarcinoma, HT29 colorectal adenocarcinoma, A549 non-small cell lung carcinoma, FaDU head and neck tumor cell lines in vitro. Tumor cell line were cultured in DMEM-10% FBS under standard conditions. One-hundred mm plastic culture dishes were seeded with $1 \times 10^6$ tumor cells and treated with vinca alkaloids or N-oxide analogs at a dose range of 0.01-100 nM. Cells were exposed with gentle rocking to a constant level of low oxygen (0.2% $O_2$-5% $CO_2$-balance $N_2$) in a hypoxia apparatus (INVIV02400 Hypoxia Workstation, Ruskin Technology) for 14 hr at 37° C. Identically treated cells were incubated under normoxia (air-5% $CO_2$) at 37° C. Cells were harvested and replated in fresh medium at a density of $1 \times 10^3$ cells/well in 48-well plastic culture plates to assess viability 24-72 hr later. Briefly, Alamar Blue was added to replicate wells on Day 0 and Day 3, and cells were incubated for a further 3-6 hr at 3° C. before fluorescence readings using a plate reader (530-560 nm excitation, 590 emission). The percent inhibition of proliferation was calculated and plotted against control-treated cells at each drug concentration. The 50% growth inhibitory concentration ($IC_{50}$) values were calculated for the paired normoxic and hypoxic treatments. The Hypoxia Cytotoxicity Ratio (HCR) was determined as the ratio of the $IC_{50}$ of the compound under normoxic conditions vs. hypoxic conditions.

Figure 2B:
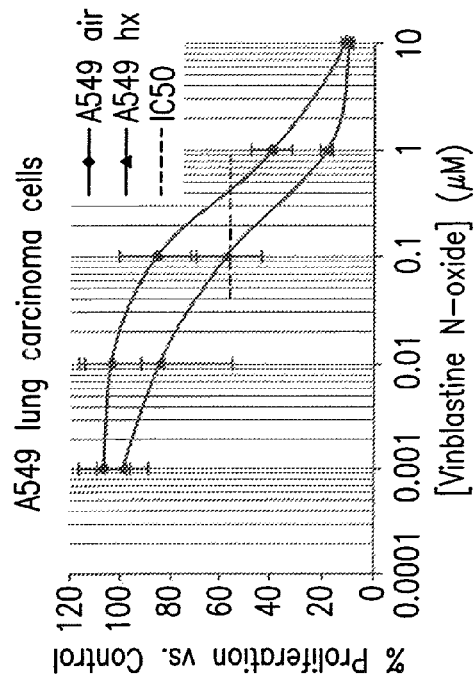
FIG. 2A-2D show hypoxia-activated cytotoxicity of vinblastine N-oxide against multiple human solid tumor cell lines in vitro.
Figure 2D:
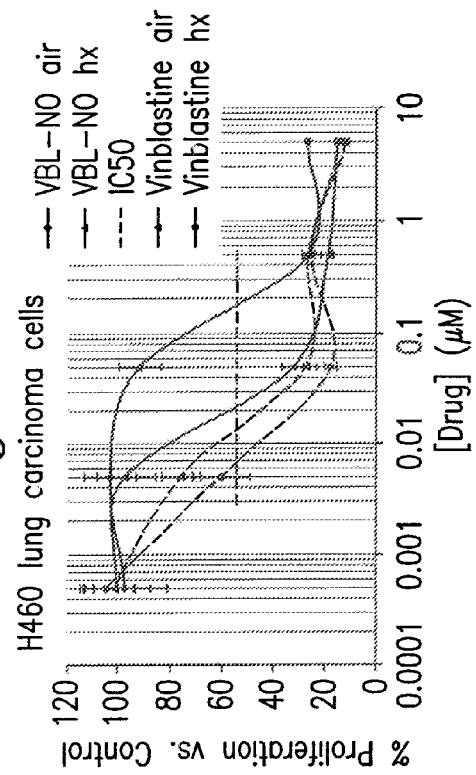
Figure 2A:
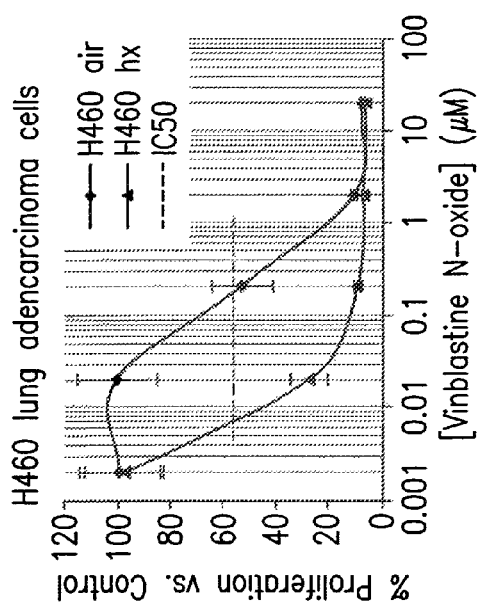
Figure 2C:
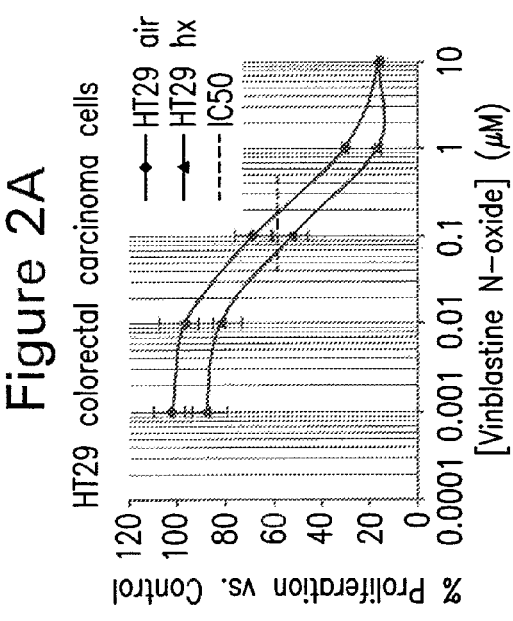

As shown in FIGS. 2A-2D and Table 2, it was demonstrated that vinblastine N-oxide has decreased cytotoxic activity under normoxic conditions compared to the parent vinblastine compound against multiple human solid tumor cell lines including H460 lung, HT29 colorectal and A549 lung adenocarcinoma cells. Upon hypoxia exposure, vinblastine N-oxide treatment was demonstrated to have potent cytotoxic activity with comparable activity to vinblastine as shown in FIG. 2D and Table 2. The HCR values of 3-21 for vinblastine N-oxide as shown in Table 2 demonstrates hypoxia-induced cytotoxicity of this compound against multiple human solid tumor cell line in vitro.

TABLE 2

Cytotoxicity and 50% inhibitory concentrations (IC50) of vinblastine N-oxide or vinblastine on human tumor cell lines exposed to normoxic vs. hypoxic conditions.

| Compound | Cell Line | IC50 Air (mM) | IC50 Hypoxia (mM) | Hypoxia Cytotoxicity Ratio (HCR)* |
|---|---|---|---|---|
| Vinblastine | H460 | 0.15 | 0.07 | 21.4 |
| N-oxide | H460 | 0.2 | 0.02 | 10 |
|  | H460 | 0.2 | 0.03 | 6.7 |
| Vinblastine | H460 | 0.02 | 0.017 | 1 |
| Vinblastine | A549 | 0.15 | 0.035 | 4.3 |
| N-oxide | A549 | 0.45 | 0.10 | 4.5 |
| Vinblastine | HT29 | 0.15 | 0.05 | 3 |
| N-oxide | HT29 | 0.2 | 0.07 | 2.9 |
| Vinblastine N-oxide | SiHa | 4 | 0.7 | 4.3 |
| Vinblastine N-oxide | FaDu | 0.15 | 0.02 | 7.5 |

*HCR is defined as (IC50 air)/(IC50 hypoxia)

Figure 3A:
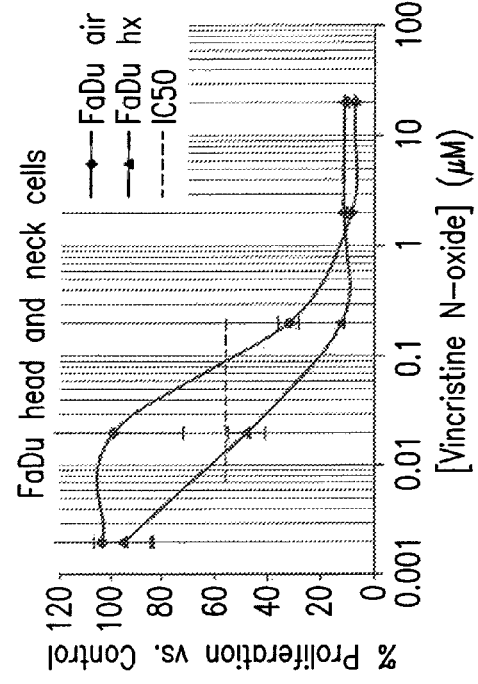
FIGS. 3A-3D show hypoxia-activated cytotoxicity of vincristine N-oxide against multiple human solid tumor cell lines in vitro.
Figure 3B:
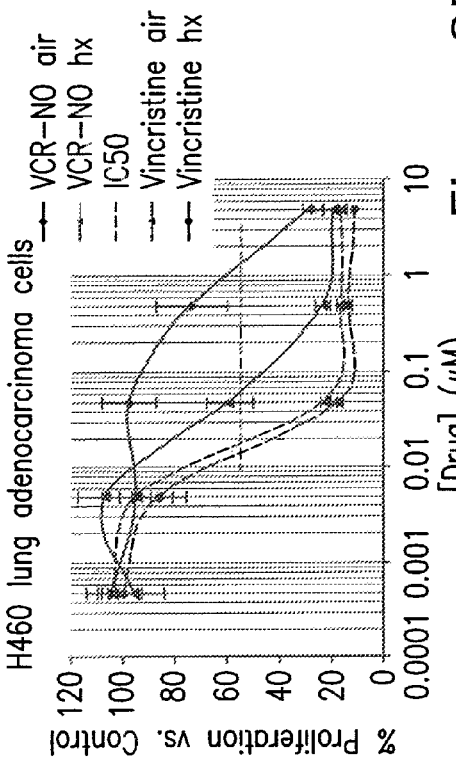
Figure 3C:
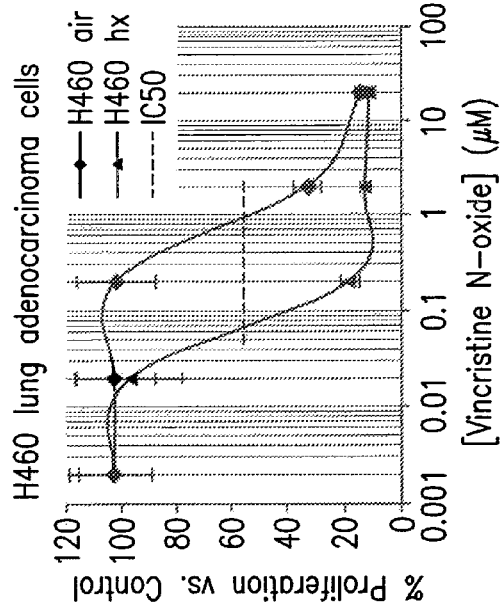
Figure 3D:
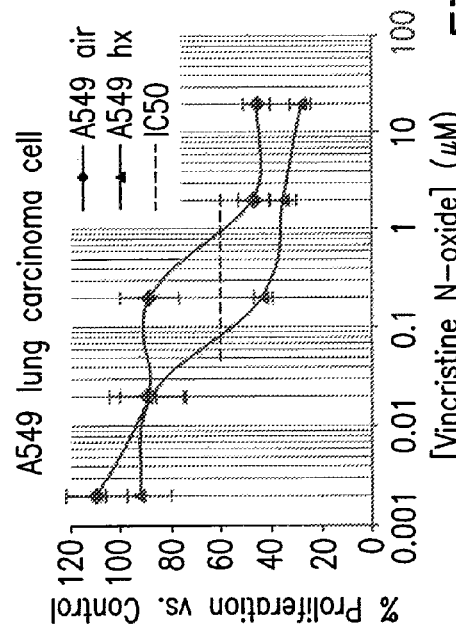

As shown in FIGS. 3A-3D and Table 3, it was demonstrated that vincristine N-oxide has decreased cytotoxic activity under normoxic conditions compared to the parent vincristine compound against multiple human solid tumor cell lines. Upon hypoxia exposure, vincristine N-oxide treatment was demonstrated to have potent cytotoxic activity with comparable activity to vincristine (FIG. 3D and Table 3). The HCR values of 5-25 for vincristine N-oxide as shown in Table 3 demonstrates hypoxia-induced cytotoxicity of this compound against multiple human solid tumor cell line in vitro.

TABLE 3

Cytotoxicity and 50% inhibitory concentrations (IC50) of vincristine N-oxide or vincristine on human tumor cell lines exposed to normoxic vs. hypoxic conditions.

| Compound | Cell Line | IC50 Air (mM) | IC50 Hypoxia (mM) | Hypoxia Cytotoxicity Ratio (HCR)* |
|---|---|---|---|---|
| Vincristine | H460 | 1.5 | 0.06 | 25 |
| N-oxide | H460 | 0.9 | 0.065 | 14 |
|  | H460 | 1 | 0.2 | 5 |
| Vincristine | H460 | 0.017 | 0.015 | 1.1 |
| Vincristine N-oxide | A549 | 0.9 | 0.08 | 11.2 |
| Vincristine N-oxide | FaDu | 0.09 | 0.015 | 6 |

*HCR is defined as (IC50 air)/(IC50 hypoxia)

Example 8

Cytotoxicity of Vinca Alkaloid Analogs and N-Oxides Thereof in Solid Tumor Lines Using Clonogenic Assays The differential cytotoxicity of vinca alkaloids and analog N-oxides thereof on different solid tumor cell lines are demonstrated in vitro under normoxic conditions and 0.2% $O_2$ hypoxic conditions using colony formation (clonogenic) assays. Shown are results in FIG. 4 obtained from treatment effects of vinblastine N-oxide on the growth of viable colonies of H460 lung carcinoma tumor cells following exposure to normoxic (20% $O_2$) vs. hypoxic (0.2% $O_2$) conditions.

Figure 4:
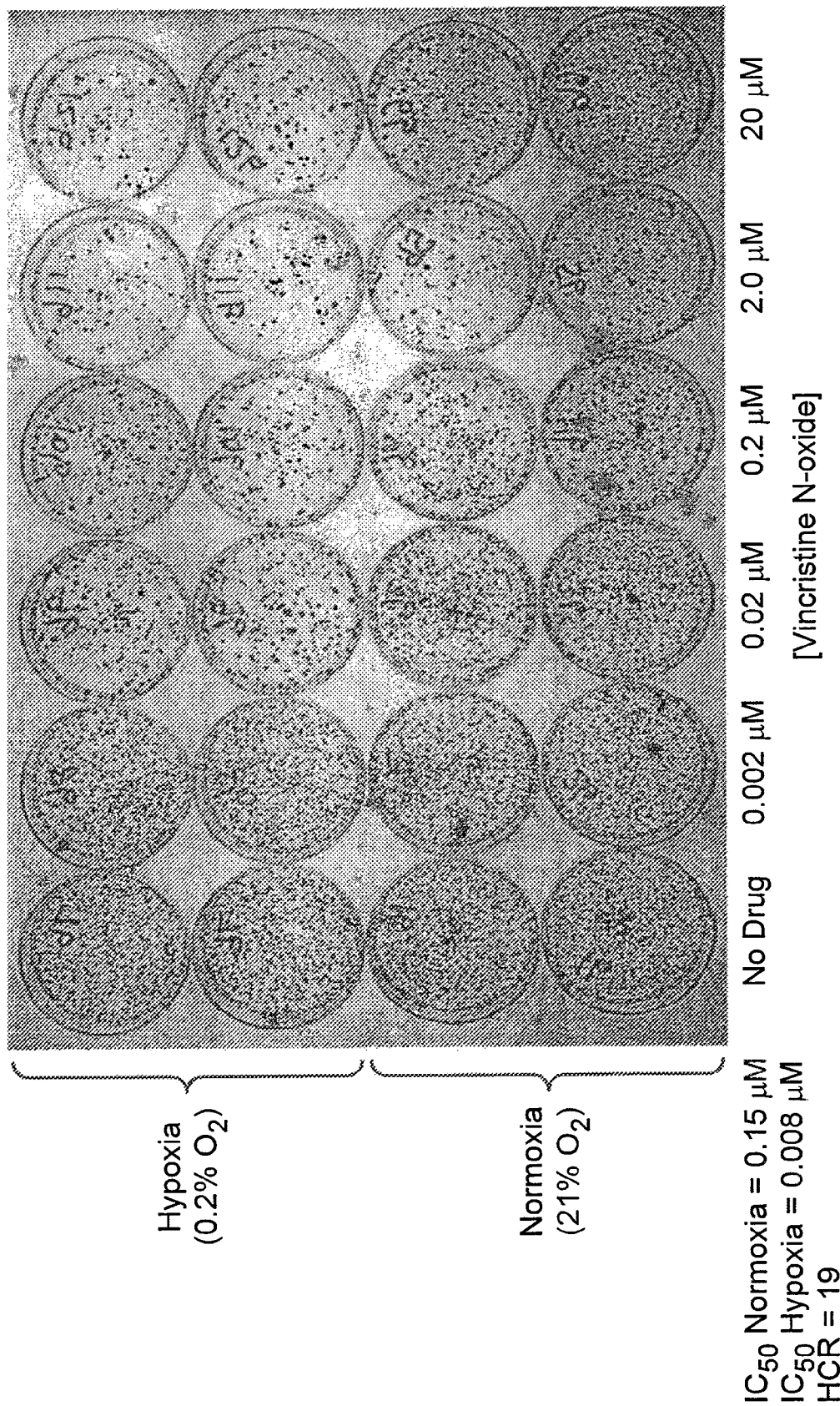
FIG. 4 shows differential cytotoxic activity of vincristine N-oxide against viable H460 lung adenocarcinoma tumor colonies under hypoxic vs. normoxic conditions in vitro.

Human H460 lung adenocarcinoma tumor cells were cultured in DMEM-10% FBS under standard conditions and seeded in 100 mm plastic culture dishes at a density of $1 \times 10^6$ cells/dish. Cells were then treated with vinblastine N-oxide at a 0.01-100 nM dose range. Cells were exposed with gentle rocking to a constant level of low oxygen (0.2% $O_2$-5% $CO_2$-balance $N_2$) in a hypoxia apparatus (INVIVO2400 Hypoxia Workstation, Ruskin Technology) for 14 hr at 3° C. Identically treated cells were incubated under normoxia (air-5% $CO_2$) at 3° C. Cells were harvested and replated in fresh medium at a density of $1 \times 10^5$ cells/well in fresh plastic culture plates to assess the growth of viable colonies 7 days later. Colonies were fixed, stained with 0.4% crystal violet and enumerated 7 days later. The 50% Inhibitory concentration to block the number of viable colonies compared to control-treated cells under normoxic and hypoxic conditions are calculated. As shown in FIG. 4, vinblastine N-oxide had decreased cytotoxic activity against H460 lung tumor cells under normoxic conditions compared to its potent cyotoxic activity under hypoxic conditions. Vinblastine N-oxide demonstrates a Hypoxia Cytotoxicity Ratio of ~20 against the growth of viable H460 tumor colonies in vitro (FIG. 4). The results demonstrated that vinblastine N-oxide is a prodrug that is activated under hypoxia to a potent cyototoxin with low nanomolar $IC_{50}$ inhibitory activity against human solid tumor cell lines in vitro.

Example 9

Activation of Cytotoxicity of Vinca Alkaloid N-Oxides Analogs Against Human Solid Tumor Cell Lines is Oxygen Dependent Our results demonstrate the vinca alkaloid N-oxide analogs have decreased cytotoxic activity under normoxic conditions but are activated to potent cytotoxic agents under conditions of hypoxia. Human H460 lung adenocarcinoma tumor cells were cultured in DMEM-10% FBS under standard conditions. One-hundred mm plastic culture dishes were seeded with $1 \times 10^6$ tumor cells/dish and treated with vinca alkaloids or N-oxide analogs at a 0.01-100 nM dose range. Cells were exposed with gentle rocking to a constant level of low oxygen (0.2, 1% or 5% $O_2$-5% $CO_2$-balance $N_2$) in a hypoxia apparatus (INVIVO2400 Hypoxia Workstation, Ruskin Technology) for 14 hr at 3° C. Identically treated cells were incubated under normoxia (air-5% $CO_2$) at 3° C. Cells were harvested and replated in fresh medium at a density of $1 \times 10^3$ cells/well in 48-well plastic culture plates to assess viability 24-72 hr later. Briefly, Alamar Blue was added to replicate wells on Day 0 and Day 3, and cells were incubated for a further 3-6 hr at 37° C. before fluorescence readings using a plate reader (530-560 nm excitation, 590 emission). The percent inhibition of proliferation was calculated and plotted against control-treated cells at each drug concentration. The 50% growth inhibitory concentration ($IC_{50}$) values were calculated for the paired normoxic and hypoxic treatments. The Hypoxia Cytotoxicity Ratio (HCR) was defined as (($IC_{50}$ in Hypoxia)/($IC_{50}$ in Normoxia)). In FIG. 5 we demonstrate that the activation of cytotoxicity against human H460 lung adenocarcinoma cells is oxygen dependent. Increased cytotoxicity of vinblastine N-oxide against cultured H460 lung tumor cells was observed as the oxygen concentrations were decreased. Shown in FIG. 5 are the Hypoxia Cytotoxicity Ratio (HCR) of vinblastine N-oxide plotted against the partial $O_2$ concentrations of 0.2%, 1%, and 5% $O_2$ that were tested.

Example 10

Bioreduction of Vinca-Alkaloid N-Oxides to their Respective Parent Compounds in Hypoxic Cancer Cells as Measured by LC/MS-MS Analysis Here we demonstrate that vinblastine N-oxide and vicristine N-oxide are bioreduced under (0.2% $O_2$) hypoxic conditions to their respective parent compounds as detected by chromatography and mass spectrometric analysis. Human H460 lung adenocarcinoma tumor cells were seeded in 100 mm dishes at a density of $1 \times 10^6$ cells/dish and untreated or treated with vinca alkaloid N-oxide analogs at a dose range of 0.02-7 μM. Cells were exposed with gentle rocking to a constant level of low oxygen (0.2% $O_2$-5% $CO_2$-balance N2) in a hypoxia apparatus (INVIVO2400 Hypoxia Workstation, Ruskin Technology) for 12 hr at 37° C. Identically treated cells were incubated under normoxia (air-5% $CO_2$) at 3° C. Cells were harvested and lysed in DNA lysis buffer (20 mM Tris-HCL, pH 8.0, 1 mM EDTA, 0.1% Triton X-100) and stored at −80° C. for analysis of DNA content and LC/MS/MS analysis. Lysates were thawed and analysed for DNA using Hoescht 33258dye and fluorescence ($\lambda_{excitation}$ 350 nm, $\lambda_{emmission}$ 455 nm) in order to normalize the measured vinca alkaloid or N-oxide analog concentrations to amounts of cells lysed in the experiment. Lysates were mixed with 150 ml of methanol containing 0.1% acetic acid and vinca alkaloid internal standard, and vortexed for 10 min, and centrifuged for 5 min at 18000 g. Clarified supernatants were transferred to HPLC vials fitted with glass inserts and analyzed by LC-MS/MS. Chromatography was performed on an Acquity HPLC system fitted with an Acquity BEH C18 colum, and used 0.1% (v:v) formic acid in water for mobile phase A, and 0.1% (v:v) formic acid in acetonitrile for mobile phase B. Mass spectral analysis was performed using a Micromass Quattro Micro triple quadupole mass spectrometer.

In FIGS. 6A-6D are shown the chromatograms of vinblastine and vinblastine N-oxide analog of the HPLC/MS-MS analysis of extracellular medium from vinblastine N-oxide treated H460 tumor cells under normoxia and hypoxia conditions. The vinblastine chromatogram distinctly illustrates the increased liberation of vinblastine and a decreased peak of vinblastine N-oxide under hypoxia exposure. In FIGS. 7A and 7B are shown the quantitative amounts of vinblastine N-oxide and the vinblastine parent compound measured using mass spectral analysis from lysates or the extracellular medium of 0.2 vinblastine N-oxide treated cells under hypoxic or normoxic conditions. The amounts of each compound were calculated from standard curves. These results clearly demonstrate that vinblastine N-oxide is bioreduced to vinblastine under hypoxia exposure and is detected in both the lysates and extracellular medium of treated cells. The extracellular liberation of vinblastine upon hypoxia activation in treated cells indicates that vinblastine N-oxide analog may have potential bystander cytotoxic effects.

In FIGS. 8A and 8B are shown the quantitative amounts of vincristine N-oxide and the vincristine parent compound measured using mass spectral analysis from lysates or the extracellular medium of 7 μM vincristine N-oxide treated H460 lung adenocarcinoma cells under hypoxic or normoxic conditions. The amounts for each compound were calculated from standard curves. These results clearly demonstrate that vincristine N-oxide is bioreduced to vincristine under hypoxia exposure and is detected in both the lysates and extracellular medium of treated cells. The extracellular liberation of vincristine upon hypoxia activation in treated cells indicates that vincristine N-oxide analog may have potential bystander cytotoxic effects.

Example 11

Vinca-Alkaloid N-Oxide Analogs have Reduced Systemic and Lethal Toxicity Compared to their Parental Vinca-Alkaloids In Vivo We demonstrate here that vinblastine N-oxide and vincristine N-oxide analogs have decreased systemic and lethal toxicity compared to their respective parent compounds, vinblastine and vincristine, in rodents in vivo.

In FIG. 9 are shown the results of a 28-day acute toxicity study of female athymic nu/nu mice that were injected intraperitoneally (ip) with 6-60 mg/kg vinblastine N-oxide once every three days for a total of 5 treatments (q3d×5). Body weights were monitored twice weekly and up to 2 weeks following treatment. Mice were also injected ip with 4 or 6 mg/kg vinblastine using the same q3d×5 schedule as a positive control. Shown in FIG. 9 are the % Body Weight Loss of mice (n=5/group) treated with vinblastine N-oxide at a dose range of 6-60 mg/kg or vinblastine at 4-6 mg/kg. Mice treated with vinblastine at a lethal dose of 4 or 6 mg/kg succumbed with a median day of death of 10.8 or 9.8 days, respectively. In contrast, mice treated with vinblastine N-oxide at doses of up to 15 times the lethal dose of vinblastine showed no evidence of significant body weight loss or gross symptoms of toxicity at 14 days following the last treatment.

In FIG. 10 are shown the results of a 28-day acute toxicity study of female athymic nu/nu tumor-bearing mice that were injected intravenously (iv) with 0.6-10 mg/kg vincristine N-oxide once every three days for a total of 5 treatments (q3d×5). Body weights were monitored twice weekly and up to 2 weeks following treatment. Mice were also injected iv with 0.6 or 1 mg/kg vincristine using the same q3d×5 schedule as a positive control. Shown in FIG. 10 are the % Body Weight Loss of mice (n=5/group) treated with vincristine N-oxide at a dose range of 0.6-10 mg/kg or vincristine at 0.6-1 mg/kg. Mice treated with vincristine showed significant body weight loss during the course of treatment. In contrast, mice treated with vincristine N-oxide at doses of up to 10 times the maximum tolerated dose of vincristine showed no evidence of significant body weight loss or gross symptoms of toxicity at 14 days following the last treatment.

Example 12

Anti-Tumor Activity of Vinca-Alkaloids and Analog N-Oxides Thereof in Solid Tumor Models in Mice The in vivo antitumor efficacy of vinca-alkaloid and analog N-oxides will be evaluated using xenograft murine models. For example, human H460 lung adenocarcinoma, HT29 colorectal adenocarcinoma, or A549 lung carcinoma tumor fragments (approximately 1 mm$^3$) will be implanted subcutaneously (sc) into female nude (nu/nu) mice. When the tumors reach approximately 100 mm$^3$ in size (25 days following implantation), the animals will be pair-matched into 10 mice per group. Mice will be injected iv with vinca-alkaloid N-oxide analog at a dose of 1-200 mg/kg on a q3d×5 schedule. Mice will also be treated with vehicle as a negative control and the bioreduced parent compound at the maximal tolerated dose as a positive control using the same schedule. Tumors will be measured with calipers twice weekly and tumor volume calculated using the formula: Tumor Volume (mm$^3$)=((width)$^2$× length)/2. Animals will be monitored for signs of toxicity and weighed daily for the first 5 days of the study and then twice-weekly until the study end. As pre-defined in the protocol, each animal will be actively euthanized when its tumor reached the pre-determined endpoint size of 1200 mm$^3$ or at the conclusion of the study (day 60) whichever comes first. The time to endpoint (TTE) will be calculated for each mouse as TTE (days)=(log$_{10}$(endpoint volume mm$^3$)−b)/m where b is the intercept and m is the slope of the line obtained by linear regression of a log-transformed tumor growth data set. Treatment outcome will be determined from tumor growth delay (TGD) which is defined as the increase in median TTE in a treatment (T) group as compared to the control (C) group (TGD=T−C) expressed in days or as a percentage of the median TTE of the control group % TGD= ((T−C)/C)×100. Kaplan-Meier plots will be constructed to demonstrate the percentage animals remaining in the study as a function of time following treatment. Statistical significance between the treated vs. control groups will be evaluated by logrank analysis.

In another example, female nude mice (nu/nu) will be implanted sc with fragments of human BxPC-3 pancreatic tumors. When the tumors reach approximately 60-80 mm$^3$ in size, the animals will be pair-matched into treatment and control groups containing ten mice per group. Mice will be injected iv with vinca-alkaloid N-oxide analog at a dose of 1-200 mg/kg on a q3d×5 schedule. Mice will also be treated with vehicle as a negative control and the bioreduced parent compound at the maximal tolerated dose as a positive control using the same schedule. Tumors will be measured with calipers twice weekly and tumor volume calculated using the formula: Tumor Volume (mm$^3$)=((width)$^2$× length)/2. Animals will be monitored for signs of toxicity and weighed daily for the first 5 days of the study and then twice-weekly until the study end. As pre-defined in the protocol, the experiment will be terminated when the vehicle control group tumor size reaches an average of ~2000 mm$^3$ (~27 days). Upon termination, the mice will be weighed, sacrificed, tumors excised, and the mean tumor volume per group calculated. Tumor growth inhibition (TGI), defined as the change in mean tumor volume of the treated groups/the change in mean tumor volume of the control group×100 (ΔT/ΔC) will be calculated for each group. Statistical comparisons will be carried out using ANOVA followed by the Dunnett multiple comparisons test.

The anti-tumor activity of vinca-alkaloid N-oxides will also be assessed in an orthotopic (ot) solid tumor xenograft model. In one embodiment, female athymic mice will injected with 2.5×10$^6$ human BxPC-3 pancreatic cells directly into the pancreas parenchyma. Treatment with vehicle (negative control), 10-200 mg/kg vinca-alkaloid N-oxide analog (iv), or 40 mg/kg gemcitabine (ip) will be initiated on day 14 post-tumor implantation at a q3d×5 schedule. Treatment groups will consist of 12 mice/group; an extra 5 mice be added to each group for histological analysis. Mice will be monitored twice daily for symptoms of disease and actively euthanized based on the criteria outlined by the Institutional Ethical Committee; the day of sacrifice will be considered the day of cancer death. Prolongation of survival, a primary endpoint in the study, will be evaluated using Kaplan-Meier plots and statistical significance of treatment responses compared to control groups will be analyzed by logrank analysis. For histological analysis, mice will be sacrificed at multiple days throughout treatment course and blinded tissue sections from resected tumors will be analysed by standard immunohistochemical techniques for detection of tumor proliferation (BrDUrd incorporation), hypoxia (pimonidazole staining), vasculature (CD31 staining), apoptosis (TUNEL staining) and necrosis. The effects of vinca-alkaloid N-oxide analogs in comparison to vehicle control treated on the tumor microenvironment will be qualitatively and quantitatively assessed. In addition, other target organs such as the lung and liver that demonstrate metastases formation will be resected and analysed for treatment effects on metastatic spread. Five μm-thick formalin-fixed paraffin-embedded tissue sections will be stained with hematoxylin and eosin (H&E) gross histopathological analysis will be performed in a blinded fashion to compute the metastatic tumor burden. The total percentage of space occupied by invasive tumor cells was enumerated and will be expressed as a percentage of total tissue evaluated. Statistical analysis will be computed using the non-parametric Mann-Whitney U-test. The effects of vinca-alkaloid N-oxides on preventing the growth of metastatic tumor cells and preventing the metastatic spread of hypoxic tumor cells will be evaluated.

Further, the in vivo antitumor activity of vinca-alkaoid and analog N-oxide in combination with chemotherapeutic agents and/or radiotherapy will be evaluated using a xenograft model in nude mice.

Further, the in vivo antitumor activity of vinca-alkaoid and analog N-oxide in combination with biological agents, such as therapeutic monoclonal antibodies (anti-VEGF, anti-EGF) will be evaluated using a xenograft model in nude mice.

Further, the in vivo antitumor activity of vinca-alkaoid and analog N-oxide in combination with small molecules tyrosine kinase inhibitors will be evaluated using a xenograft model in nude mice.

Further, the in vivo antitumor activity of vinca-alkaoid and analog N-oxide in combination with vascular disrupting, vascular damaging, or anti-angiogenic agents will be evaluated using a xenograft model in nude mice.

Further, the in vivo antitumor activity of vinca-alkaoid and analog N-oxide in combination with Hypoxia-Inducible Factor-1 or -2 (HIF-1 or HIF-2) antagonists will be evaluated using a xenograft model in nude mice.

Further, the in vivo antitumor activity of vinca-alkaoid and analog N-oxide in combination with other therapeutic agents that target euoxic tumor cells will be evaluated using a xenograft model in nude mice.

Further, the in vivo antitumor activity of vinca-alkaoid and analog N-oxide in combination with other agents that decrease tumor oxygenation or increase tumor consumption will be evaluated using a xenograft model in nude mice.

Example 13

Tumor Selectivity of Vinca-Alkaloids N-Oxide Analogs

The systemic and local tumor concentrations of vinca-alkaloid N-oxide analogs and their bioreduced parent compound metabolites will be monitored in tumor bearing mice using quantitative analytical procedures such as HPLC/MS-MS.

In one example, female athymic nude mice will be sc injected with $1 \times 10^7$ H460 lung adenocarcinoma tumor cells. Animals will be dosed when the mean tumor volume reached 300 mm$^3$. Mice will be randomized into treatment groups of 5 mice/group. The mice will receive a single iv bolus injection of vinca alkaloid N-oxide at 10-200 mg/kg by tail-vein injections. Three mice per dose will be sacrificed at 15 min, 30 min, 1 hr, 2 hr, 4 hr, 8 hr, 12 hr and 24 hr post-treatment. Plasma and dried tumor samples will be collected and stored at −80° C. for further analysis using HPLC/MS/MS. Quantitation of vinca-alkaloid N-oxides and its bioreduced metabolites, from plasma and tumor samples will be determined following liquid-liquid extraction in methanol containing 0.1% (v/v) acetic acid. Following liquid extraction, plasma samples will be spiked with known concentrations of the internal standard, and subjected to centrifugation at 15000× rpm for 10 min at 4° C. The resulting supernatants will be analyzed by chromatography using an Acquity HPLC system fitted with an Acquity BEH C18 colum, and used 0.1% (v:v) formic acid in water for mobile phase A, and 0.1% (v:v) formic acid in acetonitrile for mobile phase B. Mass spectral analysis will be performed using a Micromass Quattro Micro triple quadupole mass spectrometer. Resected tumor samples (~300 mg) will be homogenized in cold water, spiked with known internal standard and subjected to liquid-liquid extraction. Following the centrifugation of tissue homogenates, the supernatants will be collected and concentrated to a final volume of 0.4 ml using a vacuum concentrator prior to HPLC/MS/MS analysis as described above. The amounts of vinca-alkaloid N-oxides and its bioreduced parent metabolite will be analysed from plasma and tumor samples at various times post-treatment to demonstrate increased tumor selectivity and decreased systemic exposure following drug administration.

Example 14

In Vivo Anti-Tumor Efficacy of Vinca-Alkaloids and Analog N-Oxides Thereof in Murine Syngeneic Leukemias The in vivo antitumor efficacy of vinca alkaloids and analog N-oxides were evaluated using syngeneic experimental murine models of hematological malignancies. For example, B6D2F1 mice (n=8/group) were inoculated subcutaneously (sc) in the right flank with $1 \times 10^6$ murine L1210 leukemic tumor cells. Growth of tumors was monitored as the average tumor size reached 80 to 120 mm$^3$. Seven days later (day 1 of the study) mice were pair matched into the appropriate treatment groups and were treated with vincristine, vinblastine and analog N-oxides by intravenous administration via the tail vein. Test agents were administered on multiple treatment regimen (q3d×5) to yield optimal dose schedule benefit. Vehicle control treated mice served as the negative control group; mice treated with the bioreduced parent compounds, vincristine and vinblastine, dosed at their mean therapeutic doses (MTDs), served as the positive control groups. Tumors were measured with calipers twice weekly and tumor volume calculated using the formula: Tumor Volume (mm$^3$)= ((width)$^2$× length)/2. Animals were monitored for signs of toxicity and weighed daily for the first 5 days of the study and then twice-weekly until the study end. As pre-defined in the protocol, each animal was actively euthanized when its tumor reached the pre-determined endpoint size of 2000 mm$^3$ or at the conclusion of the study (day 37) whichever came first. The time to endpoint (TTE) was calculated for each mouse as TTE (days)=(log$_{10}$(endpoint volume mm$^3$)−b)/m where b is the intercept and m is the slope of the line obtained by linear regression of a log-transformed tumor growth data set. Treatment outcome was determined from tumor growth delay (TGD) which is defined as the increase in median TTE in a treatment (T) group as compared to the control (C) group (TGD=T−C) expressed in days or as a percentage of the median TTE of the control group % TGD=((T−C)/C)×100. Kaplan-Meier plots were constructed to demonstrate the percentage animals remaining in the study as a function of time following treatment. Statistical significance between the treated vs. control groups was evaluated by logrank analysis.

As indicated in FIG. 11, VCR-NO resulted in a significant dose dependent L1210 tumor growth delay with superior activity as compared to the vincristine parent compound. Administered at a 75 mg/kg dose on a q3d×5 schedule, VCR-NO resulted in 49% TGD (P<0.01) as compared to 8% for vincristine (NS). Similarly, using survival as an endpoint (FIG. 12), VCR-NO dosed at 75 mg/kg q3d×5 resulted in 28.2 days median survival as compared with 19.6 days for vincristine given at its MTD of 1 mg/kg q3d×5 and 18.1 days for vehicle treated mice.

As shown in FIGS. 13 and 14 VBL-NO also demonstrated significant anti-tumor efficacy in the L1210 leukemia model.

VBL-NO dosed at 30 mg/kg on a q3dx5 schedule resulted in 41% TGD with a median survival of 25.5 days as compared to 18.1 days for vehicle treated mice. The anti tumor efficacy seen with VBL-NO dosed at 30 mg/kg q3dx5 was comparable to the parental compound vinblastine given at its MTD of 5 mg/kg q3dx5 (34% TGD, 24.3 days survival).

In a related example, the in vivo antitumor efficacy of vinca alkaloids and analog N-oxides was evaluated using another syngeneic experimental murine model of hematological malignancies, P388. This model was developed by subcutaneously inoculating B6D2F1 mice (n=8/group) with $1 \times 10^6$ murine P388 leukemic tumor cells using similar methodology to that described above for L1210. Seven days after tumor inoculation, when the average tumor size reached 80 to 120 mm³ (day 1 of the study), mice were placed into the appropriate treatment groups and were treated with the parental agents, vincristine and vinblastine, as well as the test agents, the analog N-oxides, by intravenous administration. Agents were administered on multiple treatment regimen (q3dx5) to yield optimal dose schedule benefit. Efficacy of treatment with the N-oxide analogs was determined by Tumor Growth Delay (TGD) and Kaplan-Meier survival analysis as described for L1210, the exception being that the conclusion of the study was day 45 or the predefined endpoint size of 2000 mm³ whichever came first. Vehicle control treated mice served as the negative control group; mice treated with the standard agents, vincristine and vinblastine, dosed at their MTDs, served as the positive control groups.

As indicated in FIG. 15, VCR-NO resulted in a highly significant P388 tumor growth delay. Administered at a 60 mg/kg dose on a q3dx5 schedule, VCR-NO resulted in 76% TGD (P<0.001) as compared to 54% for vincristine. Similarly, using survival as an endpoint (FIG. 16) VCR-NO dosed at 60 mg/kg q3dx5 resulted in 23.8 days median survival as compared with 20.8 days for vincristine given at its MTD of 1 mg/kg q3dx5 and 13.5 days for vehicle treated mice.

As shown in FIGS. 17 and 18 VBL-NO also demonstrated significant anti-tumor efficacy in the P388 leukemia model. VBL-NO dosed at 30 mg/kg on a q3dx5 schedule resulted in 92% TGD (P<0.001) with a median survival of 25.9 days as compared to 13.4 days for vehicle treated mice.

Example 15

In Vivo Anti-Tumor Efficacy of Vinca-Alkaloids and Analog N-Oxides Thereof in Murine Xenograft Models of Human Leukemia and Cells Derived from Hematalogical Malignancies The in vivo antitumor efficacy of vinca alkaloids and analog N-oxides were evaluated using murine xenograft models of human hematological malignancies. In one example, female nude mice (n=10) were inoculated subcutaneously with $15 \times 10^6$ human K562 myelogenous leukemia cells in a 1:1 ratio with matrigel on the right flank. Tumor volumes were monitored and calculated using the formula: Tumor volume=(a²×b/2) where 'a' is the smallest diameter and 'b' is the largest diameter. Once the established tumors reached approximately 75-150 mm³ (individual tumor volumes may range from 100 to 250 mg) the mice were assigned to the various vehicle control and treatment groups such that the mean tumor volumes in the treated groups were within 10% of the mean tumor weight in the vehicle control group. On the same day (day 1) and days 4, 7, 10, and 13, vinca-alkaloid N-oxide analogs (VCR-NO, VBL-NO) were administered intravenously according to a q3dx5 schedule. Mice were also treated with vehicle (negative control) and the standard agents, vinblastine and vincristine (positive controls). Tumor volumes were recorded three times a week starting when tumors were palpable and including the day of study termination. Animals were monitored for signs of toxicity and body weights were recorded twice a week starting on the first day of treatment and including the day of study termination. As pre-defined in the protocol, each animal was actively euthanized if the animal was found moribund, if the body weight decreased below 14 g, if the individual tumor volume reached 3,000 mm³ or if the tumor ulcerated. The mean day of sacrifice were calculated to determine the tumor growth delay and tumor growth inhibition effects of each test article as compared to vehicle control. Survival endpoints were defined as a tumor volume reaching ~3000 mm³ for each tumor type and Kaplan-Meier plots were constructed to demonstrate the percentage animals remaining in the study as a function of time following treatment. Statistical significance between the treated vs. control groups was evaluated by logrank analysis.

As indicated in FIG. 19, VCR-NO resulted in a significant dose-dependent K562 tumor growth inhibition. Administered at a 30 mg/kg or 40 mg/kg dose on a q3dx5 schedule, VCR-NO resulted in 60% and 84% tumor growth inhibition (P<0.01) respectively as compared to vehicle control. Similarly, using survival as an endpoint (FIG. 20), VCR-NO dosed at 30 mg/kg or 40 mg/kg on a q3dx5 schedule resulted in 48 day and 60 day median survival respectively as compared with 30 days for vehicle treated mice. Efficacy seen with VCR-NO was similar to that of the standard agent vincristine given at its MTD of 1.5 mg/kg q3dx5.

As shown in FIGS. 21 and 22 VBL-NO also demonstrated significant anti-tumor efficacy in the K562 myelogenous leukemia model. VBL-NO dosed at 25 mg/kg or 35 mg/kg on a q3dx5 schedule resulted in 77% and 89% tumor growth inhibition (P<0.01) respectively as compared to vehicle control. Similarly, using survival as an endpoint (FIG. 22), VBL-NO dosed at 25 mg/kg or 35 mg/kg on a q3dx5 schedule resulted in 51 day and 57 day median survival respectively as compared with 30 days for vehicle treated mice. Efficacy seen with VBL-NO was similar to that of the standard agent vinblastine given at its MTD of 2.5 mg/kg q3dx5.

In a related example, the in vivo antitumor efficacy of vinca alkaloids and analog N-oxides was evaluated using murine xenograft model of human hematological malignancies, HL60. In this example, female nude mice (n=10) were inoculated subcutaneously with $15 \times 10^6$ human HL60 promyelocytic leukemia cells in a 1:1 ratio with matrigel on the right flank using similar methodology to that described above for K562. As indicated in FIG. 23, VCR-NO resulted in a significant HL60 tumor growth inhibition. Administered at a 30 mg/kg or 40 mg/kg dose on a q3dx5 schedule, VCR-NO resulted in 94% and 96% tumor growth inhibition (P<0.01) respectively as compared to vehicle control. Similarly, using survival as an endpoint (FIG. 24), VCR-NO dosed at 30 mg/kg or 40 mg/kg on a q3dx5 schedule resulted in 60 day and 58 day median survival respectively as compared with 21.5 days for vehicle. Efficacy seen with VCR-NO was similar to that of the standard agent vincristine given at its MTD of 1.5 mg/kg q3dx5.

As shown in FIGS. 25 and 26 VBL-NO also demonstrated significant anti-tumor efficacy in the HL60 promyelocytic leukemia model. VBL-NO dosed at 25 mg/kg or 35 mg/kg on a q3dx5 schedule resulted in 91% and 94% tumor growth inhibition (P<0.01) respectively as compared to vehicle control. Similarly, using survival as an endpoint (FIG. 26), VBL-NO dosed at 25 mg/kg or 35 mg/kg on a q3dx5 schedule resulted in 60 day median survival as compared with 21.5 days for vehicle treated mice. VBL-NO treated mice were still alive at the end of the study and were sacrificed at day 60 according to the protocol.

Example 16

Anti-Tumor Activity of Vinca-Alkaloids and Analog N-Oxides Thereof, Alone or in Combination with Chemotherapeutic Agents, in Murine Xenograft Models of Human Solid Tumors The in vivo antitumor efficacy of vinca-alkaloid and analog N-oxides was evaluated using murine xenograft models of human solid tumors. In this example, human HT29 colorectal adenocarcinoma tumor fragments (approximately 1 mm³) were implanted sc into the flank of female nude (nu/nu) mice. When the tumors grew to approximately 80-120 mm³ in size the mice were pair-matched into 10 mice per group. Mice were injected iv with vinca-alkaloid N-oxide analogs at a range of doses on a q3dx5 schedule. Mice were also treated with vehicle (negative control) and the standard agent, CPT11 (positive control). Tumors were measured with calipers twice weekly and tumor volume calculated using the formula: Tumor Volume (mm³)=((width)²×length)/2. Animals were monitored for signs of toxicity and weighed daily for the first 5 days of the study and then twice-weekly until the study end. As pre-defined in the protocol, each animal was actively euthanized when its tumor reached the pre-determined endpoint size of 1000 mm³ or at the conclusion of the study (day 60) whichever came first. The time to endpoint (TTE) was calculated for each mouse as TTE (days)=(log$_{10}$(endpoint volume mm³)−b)/m where b is the intercept and m is the slope of the line obtained by linear regression of a log-transformed tumor growth data set. Treatment outcome was determined from tumor growth delay (TGD) which is defined as the increase in median TTE in a treatment (T) group as compared to the control (C) group (TGD=T−C) expressed in days or as a percentage of the median TTE of the control group % TGD=((T−C)/C)×100. Kaplan-Meier plots were constructed to demonstrate the percentage animals remaining in the study as a function of time following treatment. Statistical significance between the treated vs. control groups was evaluated by logrank analysis.

As indicated in Table 4 and FIG. 27, VCR-NO administered as a single agent at 15 mg/kg on a q3dx5 schedule resulted in 52% TGD in the HT29 colon model. The standard agent, CPT-11 dosed at 100 mg/kg q week×3 also resulted in 52% TGD. When VCR-NO and CPT-11 were administered in combination, TGD increased to 111%. As indicated in FIG. 28, efficacy was also demonstrated using survival as an endpoint. As single agents, both VCR-NO dosed at 15 mg/kg q3dx5 and CPT-11 dosed at 100 mg/kg q week×3 resulted in a median survival of 39.6 days compared to the vehicle control of 26 days. When used in combination VCR-NO dosed at 15 mg/kg q3dx5 and CPT-11 dosed at 100 mg/kg q week×3 resulted in a median survival of 55 days. These data provide strong rationale for the use of these agents as combination therapy.

Table 4 shows the efficacy of vincristine N-oxide analog (VCR-NO) as single agent or in combination with CPT-11 in the HT29 colon xenograft model in nude mice model (n=10) as determined by Tumor Growth Delay.

|  | VCR-NO (none) | VCR-NO (low)* | VCR-NO (high)* |
|---|---|---|---|
| CPT-11 (none) |  | 52% | 42% |
| CPT-11 (low)** | 71% | 59% | 74% |
| CPT-11 (high)** | 52% | 111% | 82% |

*VCR-NO (iv dose): low dose = 15 mg/kg q3d × 5; high dose = 25 mg/kg q3d × 5
**CPT-11 (ip dose): low dose = 50 mg/kg q week × 3; high dose = 100 mg/kg q week × 3

As indicated in Table 5 and FIG. 29, VBL-NO administered as a single agent at 20 mg/kg on a q3dx5 schedule resulted in 46% TGD in the HT29 colon model. The standard agent, CPT-11 dosed at 50 mg/kg q week×3 resulted in 34% TGD. When VBL-NO and CPT-11 were administered in combination, TGD increased to 83%. As indicated in FIG. 30, efficacy was also demonstrated using survival as an endpoint. As a single agent, VBL-NO dosed at 20 mg/kg q3dx5 resulted in a median survival of 36.1 days, and CPT-11 dosed at 50 mg/kg q week×3 resulted in a median survival of 33.1 days compared to the vehicle control of 24.7 days. When used in combination VBL-NO dosed at 20 mg/kg q3dx5 and CPT-11 dosed at 50 mg/kg q week×3 resulted in a median survival of 45.1 days. These data provide strong rationale for the use of these agents as combination therapy.

Table 5 shows the efficacy of vinblastine N-oxide analog (VBL-NO) as single agent or in combination with CPT-11 in the HT29 colon xenograft model in nude mice model (n=10) as determined by Tumor Growth Delay.

|  | VBL-NO (none) | VBL-NO (low)* | VBL-NO (high)* |
|---|---|---|---|
| CPT-11 (none) |  | 0% | 46% |
| CPT-11 (low)** | 34% | 58% | 83% |
| CPT-11 (high)** | 60% | 54% | 82% |

*VBL-NO (iv dose): low dose = 10 mg/kg q3d × 5; high dose = 20 mg/kg q3d × 5
**CPT-11 (ip dose): low dose = 50 mg/kg q week × 3; high dose = 100 mg/kg q week × 3.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method of treating or ameliorating a hyperproliferative disorder selected from the group consisting of glioblastoma, lung cancer, breast cancer, pancreatic cancer, cervical cancer, prostate cancer, soft tissue carcinoma, and colon cancer, the method comprising administering to an animal in need thereof a therapeutically effective amount of a compound selected from the group consisting of vinblastine N-oxide, desacetyl vinblastine N-oxide, vinorelbine N-oxide, vincristine N-oxide, desacetyl vinflunine N-oxide, desacetyl vinorelbine N-oxide, vindesine N-oxide and vinflunine N-oxide, or a pharmaceutically acceptable salt thereof.

2. A method of treating or ameliorating a hyperproliferative disorder selected from the group consisting of glioblastoma, lung cancer, head and neck carcinoma, breast cancer, pancreatic cancer, cervical cancer, prostate cancer, soft tissue carcinoma, colon cancer and leukemia in an animal in need thereof, the method comprising:

(a) determining whether said hyperproliferative disorder is characterized by hypoxic tissue, and
(b) treating said animal with an effective amount of a compound selected from the group consisting of vinblastine N-oxide, desacetyl vinblastine N-oxide, vinorelbine N-oxide, vincristine N-oxide, desacetyl vinflunine N-oxide, desacetyl vinorelbine N-oxide, vindesine N-oxide and vinflunine N-oxide.

3. The method of claim 1 or 2 further comprising repeatedly administering said compound to said animal at a dose below the maximum tolerated dose.

4. The method of claim 1 or 2, wherein said compound is vincristine N-oxide, or a pharmaceutically acceptable salt thereof.

5. The method of claim 4, wherein said pharmaceutically acceptable salt is the dihydrochloride salt.

6. The method of claim 1 or 2, wherein said compound is vinblastine N-oxide, or a pharmaceutically acceptable salt thereof.

7. The method of claim 6, wherein said pharmaceutically acceptable salt is the dihydrochloride salt.

8. The method of claim 1, further comprising subjecting said animal to an imaging technique selected from the group consisting of computed tomography, magnetic resonance imaging, single photon emission computer tomography and positron emission tomography prior to or during administration of said compound.

9. The method of claim 1 or 2, further comprising administering to said animal a topoisomerase 1 inhibitor.

10. The method of claim 9 wherein said topoisomerase 1 inhibitor is selected from the group consisting of topotecan, irinotecan, 9-aminocamptothecin, 10-aminocamptothecin, 10,11-methylenedioxycamptothecin and SN-38, or a pharmaceutically acceptable salt thereof.

11. The method claim 10, wherein said topoisomerase 1 inhibitor is irinotecan, or a pharmaceutically acceptable salt thereof.

12. The method of claim 11, wherein irinotecan, or a pharmaceutically acceptable salt thereof, is administered 50 mg/m$^2$ to 500 mg/m$^2$ once weekly, once every two weeks or once every three weeks.

13. The method of claim 11, wherein the compound is vinblastine N-oxide or vincristine N-oxide.

14. The method of claim 13, wherein the compound is administered 1 mg/kg one dose every three days, repeated five times to 500 mg/kg one dose every three days, repeated five times.

15. The method of claim 14, wherein the compound is administered 5 mg/kg one dose every three days, repeated five times to 50 mg/kg one dose every three days, repeated five times.

16. The method of claim 1 or 2, wherein the hyperproliferative disorder is selected from the group consisting of lung cancer, cervical cancer, and colon cancer.

17. The method of claim 16, wherein the hyperproliferative disorder is colon cancer.

18. The method of claim 1 or 2, further comprising administering one or more other active agents to the animal.

19. The method of claim 18, wherein said one or more other active agents are independently selected from the group consisting of a chemotherapeutic agent, a radiotherapeutic agent, an anti-angiogenesis agent, a vascular targeting agent, an HIF1 inhibitor, an Hsp90 inhibitor, a tyrosine kinase inhibitor, a serine/threonine kinase inhibitor, a proteasome inhibitor, an HDAC inibitor, a caspase inducer, a CDK inhibitor, and a proapoptotic molecule.

20. The method of claim 19, wherein the chemotherapeutic agent is selected from the group consisting of abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, epirubicin, epoetin alfa, estramustine, etoposide, exemestane, filgrastim, floxuridine, fludarabine, fluorouracil, fulvestrant, gemcitabine, gemtuzumab ozogamicin, gefitinib, goserelin, hydroxyurea, ibritumomab tiuxetan, idarubicin, ifosfamide, imatinib, interferon alfa-2a, interferon alfa-2b, irinotecan, letrozole, leucovorin, levamisole, lomustine, meclorethamine, megestrol, melphalan, mercaptopurine, mesna, methotrexate, methoxsalen, methylprednisolone, mitomycin C, mitotane, mitoxantrone, nandrolone, nofetumomab, oblimersen, oprelvekin, oxaliplatin, paclitaxel, pamidronate, pegademase, pegaspargase, pegfilgrastim, pemetrexed, pentostatin, pipobroman, plicamycin, polifeprosan, porfimer, procarbazine, quinacrine, rasburicase, rituximab, sargramostim, streptozocin, talc, tamoxifen, tarceva, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

21. The method of claim 19, wherein said anti-angiogenesis agent is selected from the group consisting of bevacizumab, angiostatin, endostatin, batimastat, captopril, cartilage derived inhibitor, genistein, interleukin 12, lavendustin, medroxypregesterone acetate, recombinant human platelet factor 4, tecogalan, thrombospondin, TNP-470, anti-VEGF monoclonal antibody, soluble VEGF-receptor chimaeric protein, anti-VEGF receptor antibodies, anti-PDGF receptors, inhibitors of integrins, tyrosine kinase inhibitors, serine/threonine kinase inhibitors, antisense oligonucleotides, antisense oligodexoynucleotides, siRNAs, anti-VEGF aptamers and pigment epithelium derived factor.

22. The method of claim 18, wherein said compound is administered prior to the administration of said active agents.

23. The method of claim 18, wherein said compound is administered concurrently with the administration of said active agents.

24. The method of claim 18, wherein the administration of said compound is continued beyond the administration of said active agents.

25. The method of claim 18, wherein said compound is administered after the administration of said active agents.

26. The method of claim 18, wherein the method is repeated at least once.

* * * * *